United States Patent
Wang et al.

(10) Patent No.: US 12,344,855 B2
(45) Date of Patent: Jul. 1, 2025

(54) SYSTEMS FOR CELL CONTROL

(71) Applicant: Cellino Biotech, Inc., Cambridge, MA (US)

(72) Inventors: Stan Wang, Cambridge, MA (US); Suvi Aivio, Cambridge, MA (US); Matthias Wagner, Cambridge, MA (US); Catherine Pilsmaker, Cambridge, MA (US); Marinna Madrid, Cambridge, MA (US)

(73) Assignee: Cellino Biotech, Inc., Cambridge, MA (US)

( * ) Notice: Subject to any disclaimer, the term of this patent is extended or adjusted under 35 U.S.C. 154(b) by 1018 days.

(21) Appl. No.: 17/291,591

(22) PCT Filed: Nov. 5, 2019

(86) PCT No.: PCT/US2019/059874
§ 371 (c)(1),
(2) Date: May 5, 2021

(87) PCT Pub. No.: WO2020/097083
PCT Pub. Date: May 14, 2020

(65) Prior Publication Data
US 2021/0403942 A1 Dec. 30, 2021

Related U.S. Application Data

(60) Provisional application No. 62/928,076, filed on Oct. 30, 2019, provisional application No. 62/928,081, filed on Oct. 30, 2019, provisional application No. 62/928,078, filed on Oct. 30, 2019, provisional application No. 62/841,944, filed on May 2, 2019, provisional application No. 62/756,520, filed on Nov. 6, 2018.

(51) Int. Cl.
| | |
|---|---|
| *C12N 15/85* | (2006.01) |
| *C12N 5/00* | (2006.01) |
| *C12N 5/074* | (2010.01) |
| *C12N 5/079* | (2010.01) |
| *C12N 9/22* | (2006.01) |
| *C12N 13/00* | (2006.01) |
| *C12N 15/11* | (2006.01) |
| *C12N 15/87* | (2006.01) |
| *C12N 15/90* | (2006.01) |
| *G01N 15/1433* | (2024.01) |
| *G01N 15/1434* | (2024.01) |
| *G03F 7/00* | (2006.01) |
| *G03F 7/20* | (2006.01) |
| *G01N 15/10* | (2006.01) |

(52) U.S. Cl.
CPC .......... *C12N 15/85* (2013.01); *C12N 5/0068* (2013.01); *C12N 5/0621* (2013.01); *C12N 5/0696* (2013.01); *C12N 9/22* (2013.01); *C12N 13/00* (2013.01); *C12N 15/11* (2013.01); *C12N 15/87* (2013.01); *C12N 15/907* (2013.01); *G01N 15/1433* (2024.01); *G01N 15/1434* (2013.01); *G03F 7/2006* (2013.01); *G03F 7/70025* (2013.01); *G03F 7/7055* (2013.01); *C12N 2310/20* (2017.05); *C12N 2506/08* (2013.01); *C12N 2506/45* (2013.01); *C12N 2800/80* (2013.01); *G01N 2015/1006* (2013.01)

(58) Field of Classification Search
None
See application file for complete search history.

(56) References Cited

U.S. PATENT DOCUMENTS

| | | | |
|---|---|---|---|
| 4,897,355 | A | 1/1990 | Eppstein et al. |
| 4,946,787 | A | 8/1990 | Eppstein et al. |
| 5,049,386 | A | 9/1991 | Eppstein et al. |
| 5,900,374 | A | 5/1999 | Otto-Nagels |
| 6,096,532 | A | 8/2000 | Armstrong et al. |
| 6,153,400 | A | 11/2000 | Matsumura et al. |
| 6,673,008 | B1 | 1/2004 | Thompson et al. |
| 7,754,148 | B2 | 7/2010 | Yu et al. |
| 8,492,140 | B2 | 7/2013 | Smith et al. |
| 8,546,142 | B2 | 10/2013 | Martin et al. |

(Continued)

FOREIGN PATENT DOCUMENTS

| | | |
|---|---|---|
| CN | 105492888 B | 8/2018 |
| CN | 113421221 A | 9/2021 |

(Continued)

OTHER PUBLICATIONS

Balboa et al., Conditionally stabilized dCas9 activator for controlling gene expression in human cell reprogramming and differentiation. Stem Cell Reports 5: 448-459 (2015).

(Continued)

*Primary Examiner* — Teresa E Knight
(74) *Attorney, Agent, or Firm* — Wilson Sonsini Goodrich & Rosati

(57) ABSTRACT

The disclosure relates to growing cells, directing cells to grow into specified cell types, genetically and physically manipulating cells, and addressing one or more individual cells within a mixed cell population. Aspects of the disclosure relate to vectors useful to induce developmental changes in cells, in which those vectors have a temporal component. Vectors of the disclosure encode a controllable, temporal series of events. Once the vectors are delivered into target cells, a series of discrete and different genetic events may be induced. The disclosed methods generally provide for the temporal encoding of multiplex genetic effectors in vector format for cell state transitions.

34 Claims, 28 Drawing Sheets

(56) References Cited

U.S. PATENT DOCUMENTS

| | | |
|---|---|---|
| 9,181,529 B2 | 11/2015 | Kattman et al. |
| 9,499,780 B2 | 11/2016 | Smith et al. |
| 9,783,768 B2 | 10/2017 | Larcher et al. |
| 10,078,075 B2 | 9/2018 | Wikswo et al. |
| 10,829,729 B2 | 11/2020 | Mazur et al. |
| 10,876,086 B2 | 12/2020 | Suzuki et al. |
| 11,028,358 B2 | 6/2021 | Kelso et al. |
| 11,866,735 B2 | 1/2024 | Wagner et al. |
| 11,913,029 B2 | 2/2024 | Wagner et al. |
| 11,931,737 B2 | 3/2024 | Wagner et al. |
| 2002/0055166 A1 | 5/2002 | Cannon et al. |
| 2003/0039384 A1 | 2/2003 | Bacus |
| 2003/0040104 A1 | 2/2003 | Barbera-Guillem |
| 2003/0054335 A1 | 3/2003 | Taya et al. |
| 2003/0068814 A1 | 4/2003 | Malinge |
| 2003/0082511 A1 | 5/2003 | Brown et al. |
| 2003/0203002 A1 | 10/2003 | Murphy et al. |
| 2005/0026221 A1 | 2/2005 | Richmond et al. |
| 2005/0227940 A1 | 10/2005 | Rossi et al. |
| 2007/0163963 A1 | 7/2007 | Faustman et al. |
| 2007/0212747 A1 | 9/2007 | Browne et al. |
| 2007/0292312 A1 | 12/2007 | Bachman et al. |
| 2008/0274529 A1 | 11/2008 | Dholakia et al. |
| 2009/0017543 A1 | 1/2009 | Wilkes et al. |
| 2009/0047263 A1 | 2/2009 | Yamanaka et al. |
| 2009/0170723 A1 | 7/2009 | Hoh et al. |
| 2009/0258417 A1 | 10/2009 | Tanaka et al. |
| 2009/0286317 A1 | 11/2009 | Demmler et al. |
| 2012/0034618 A1 | 2/2012 | Terskikh et al. |
| 2012/0130287 A1 | 5/2012 | Gruber |
| 2012/0208273 A1 | 8/2012 | Tarunina et al. |
| 2012/0294836 A1 | 11/2012 | Rowley et al. |
| 2012/0315620 A1 | 12/2012 | Watakabe et al. |
| 2012/0329123 A1 | 12/2012 | Nakashima et al. |
| 2013/0102772 A1 | 4/2013 | Eshima et al. |
| 2013/0113140 A1 | 5/2013 | Gunn-Moore et al. |
| 2013/0169969 A1 | 7/2013 | Popescu et al. |
| 2013/0337492 A1 | 12/2013 | Axelrod et al. |
| 2014/0004507 A1 | 1/2014 | Malic et al. |
| 2014/0030805 A1 | 1/2014 | Kasuto et al. |
| 2015/0107995 A1 | 4/2015 | Sista et al. |
| 2015/0191744 A1 | 7/2015 | Wolfe et al. |
| 2016/0177244 A1 | 6/2016 | Conway et al. |
| 2016/0177273 A1 | 6/2016 | Gong et al. |
| 2016/0195523 A1 | 7/2016 | Chatterjee et al. |
| 2016/0201089 A1 | 7/2016 | Gersbach et al. |
| 2016/0237392 A1 | 8/2016 | Lee |
| 2016/0355797 A1 | 12/2016 | Konermann et al. |
| 2016/0367702 A1 | 12/2016 | Hoge et al. |
| 2017/0009252 A1 | 1/2017 | Baylink et al. |
| 2017/0014824 A1 | 1/2017 | Boyd et al. |
| 2017/0029864 A1 | 2/2017 | Straus |
| 2017/0037351 A1 | 2/2017 | Shimase et al. |
| 2017/0204407 A1 | 7/2017 | Gilbert et al. |
| 2018/0072975 A1 | 3/2018 | Aviles et al. |
| 2018/0087021 A1 | 3/2018 | Blanchard |
| 2018/0120294 A1 | 5/2018 | Collins |
| 2018/0282682 A1 | 10/2018 | Pebay et al. |
| 2018/0321128 A1 | 11/2018 | Harriman et al. |
| 2019/0009274 A1 | 1/2019 | Novak et al. |
| 2019/0071695 A1 | 3/2019 | Wagner et al. |
| 2019/0169572 A1 | 6/2019 | Shi et al. |
| 2019/0352589 A1 | 11/2019 | Jing et al. |
| 2019/0359924 A1 | 11/2019 | Kerns et al. |
| 2020/0087607 A1 | 3/2020 | Magnant |
| 2020/0131465 A1 | 4/2020 | Floto et al. |
| 2020/0141961 A1 | 5/2020 | Ahlfors |
| 2020/0200781 A1 | 6/2020 | Smith et al. |
| 2020/0208095 A1 | 7/2020 | Oram et al. |
| 2020/0318053 A1 | 10/2020 | Kojima et al. |
| 2021/0123008 A1 | 4/2021 | Trainor et al. |
| 2021/0130774 A1 | 5/2021 | Sances et al. |
| 2021/0253991 A1 | 8/2021 | Kelso et al. |
| 2021/0254049 A1 | 8/2021 | Wang et al. |
| 2021/0261899 A1 | 8/2021 | Blanchard |
| 2021/0283606 A1 | 9/2021 | Thakkar et al. |
| 2021/0317399 A1 | 10/2021 | Nazareth et al. |
| 2021/0403942 A1 | 12/2021 | Wang et al. |
| 2022/0106549 A1 | 4/2022 | Magnant |
| 2022/0107488 A1 | 4/2022 | Berns et al. |
| 2022/0226814 A1 | 7/2022 | Iida et al. |
| 2022/0276463 A1 | 9/2022 | Hunt et al. |
| 2022/0282201 A1 | 9/2022 | Wagner et al. |
| 2022/0282202 A1 | 9/2022 | Wagner et al. |
| 2022/0282203 A1 | 9/2022 | Wagner et al. |
| 2022/0282223 A1 | 9/2022 | Wagner et al. |
| 2022/0284574 A1 | 9/2022 | Wagner et al. |
| 2023/0095664 A1 | 3/2023 | Wagner et al. |
| 2023/0235295 A1 | 7/2023 | Wagner et al. |
| 2023/0265394 A1 | 8/2023 | Wagner et al. |
| 2023/0332111 A1 | 10/2023 | Wagner et al. |
| 2024/0191204 A1 | 6/2024 | Wagner et al. |
| 2024/0253032 A1 | 8/2024 | Wagner et al. |

FOREIGN PATENT DOCUMENTS

| | | |
|---|---|---|
| EP | 3556841 A1 | 10/2019 |
| JP | 2013179916 A | 9/2013 |
| KR | 20070012514 A | 1/2007 |
| WO | WO-02086107 A2 | 10/2002 |
| WO | WO-03012082 A2 | 2/2003 |
| WO | WO-2007052716 A1 | 5/2007 |
| WO | WO-2009152529 A2 | 12/2009 |
| WO | WO-2011107599 A1 | 9/2011 |
| WO | WO-2011132584 A1 | 10/2011 |
| WO | WO-2014093718 A1 | 6/2014 |
| WO | WO-2015089351 A1 | 6/2015 |
| WO | WO-2016011070 A2 | 1/2016 |
| WO | WO-2016011080 A2 | 1/2016 |
| WO | WO-2016114438 A1 | 7/2016 |
| WO | WO-2016127069 A1 | 8/2016 |
| WO | WO-2016205680 A1 | 12/2016 |
| WO | WO-2017023974 A1 | 2/2017 |
| WO | WO-2017062838 A1 | 4/2017 |
| WO | WO-2017079682 A1 | 5/2017 |
| WO | WO-2018101004 A1 | 6/2018 |
| WO | WO-2018167399 A1 | 9/2018 |
| WO | WO-2018193446 A1 | 10/2018 |
| WO | WO-2018197183 A1 | 11/2018 |
| WO | WO-2019177856 A2 | 9/2019 |
| WO | WO-2019204750 A9 | 12/2019 |
| WO | WO-2019241885 A1 | 12/2019 |
| WO | WO-2020033871 A1 | 2/2020 |
| WO | WO-2020097083 A1 | 5/2020 |
| WO | WO-2021150631 A1 | 7/2021 |
| WO | WO-2022096315 A1 | 5/2022 |
| WO | WO-2022192157 A1 | 9/2022 |
| WO | WO-2023055543 A1 | 4/2023 |

OTHER PUBLICATIONS

Braun et al., Rapid and reversible epigenome editing by endogenous chromatin regulators. Nat Comm 8(1): 560 (2017).

Cahan et al., CellNet: Network Biology Applied to Stem Cell Engineering. Cell 158(4):903-915 (2014).

Cavelti-Weder et al.: Direct Reprogramming for Pancreatic Beta-Cells Using Key Developmental Genes. Curr Pathobiol Rep. 3(1):57-65 (2015).

Chakraborty et al., A CRISPR/Cas9-Based System for Reprogramming Cell Lineage Specification. Stem Cell Reports 3(6): 940-947 (2014).

Chang et al.: Polycistronic lentiviral vector for "hit and run" reprogramming of adult skin fibroblasts to induced pluripotent stem cells. Stem Cells 27(5):1042-1049 (2009).

Chavez et al., Highly efficient Cas9-mediated transcriptional programming. Nature Methods 12(4): 326-328 (2015).

Cheng et al., Multiplexed activation of endogenous genes by CRISPR-on, an RNA-guided transcriptional activator system. Cell Research 23(10): 1163-1171 (2013).

Copeland et al.: Application of TALES, CRISPR/Cas and sRNAs as trans-acting regulators in prokaryotes. Curr Opin Biotechnol 29:46-54 (2014).

(56) References Cited

OTHER PUBLICATIONS

Dominguez et al., Beyond editing: repurposing CRISPR-Cas9 for precision genome regulation and interrogation. Nat Rev Mol Cell Biol 17: 5-15 (2015).
Efremova et al.: Prevention of the degeneration of human dopaminergic neurons in an astrocyte co-culture system allowing endogenous drug metabolism. Br J Pharmacol. 172(16):4119-4132 (2015).
Ferre-D'Amare et al: Crystal structure of a hepatitis delta virus ribozyme. Nature 395(6702):567-574 (1998).
Ferry et al.: Rational design of inducible CRISPR guide RNAs for de novo assembly of transcriptional programs. Nat Commun. 8:14633 doi:10.1038/ncomms14633 [1-10] (2017).
Frietze et al.: Transcription factor effector domains. Sub-cell Biochemistry 52:261-277 (2011).
Gamble et al.: Improved islet recovery and efficacy through co-culture and co-transplantation of islets with human adipose-derived mesenchymal stem cells. PLoS One 13(11):e0206449 doi:10.1371/journal.pone.0206449 [1-17] (2018).
Genga et al., Controlling transcription in human pluripotent stem cell using CRISPR-effectors. Methods 101: 36-42 (2016).
German et al.: Retinal pigment epithelial cells promote spatial reorganization and differentiation of retina photoreceptors. J Neurosci Res. 86(16):3503-3514 (2008).
Gilbert et al., CRISPR-Mediated modular RNA-guided regulation of transcription in Eukaryotes. Cell 154(2): 442-451 (2013).
Gilbert et al., Genome-Scale CRISPR-Mediated Control of Gene Repression and Activation. Cell 159(3): 647-661 (2014).
Gossen et al. Tight control of gene expression in mammalian cells by tetracycline-responsive promoters. PNAS USA 89.12 (1992): 5547-5551.
Gossen et al. Transcriptional activation by tetracyclines in mammalian cells. Science 268(5218):1766-1769 (1995).
Herberg et al.: Computational modelling of embryonic stem-cell fate control. Development 142(13):2250-2260 (2015).
Hilton et al., Epigenome editing by a CRISPR-Cas9-based acetyltransferase activates genes from promoters and enhancers. Nat Biotech 33(5): 510-517 (2015).
Horlbeck et al., Compact and highly active next-generation libraries for CRISPR-mediated gene repression and activation. eLIfe 5: 914 (2016).
Jang et al.: Dynamics of embryonic stem cell differentiation inferred from single-cell transcriptomics show a series of transitions through discrete cell states. Elife 6:e20487 doi:10.7554/eLife.20487 [1-28] (2017).
Jeon et al.: Insulin-like growth factor binding protein-6 released from human mesenchymal stem cells confers neuronal protection through IGF-1R-mediated signaling. Int J Mol Med. 40(6):1860-1868 (2017).
Jin et al.: Enhanced differentiation of human pluripotent stem cells into cardiomyocytes by bacteria-mediated transcription factors delivery. PLoS One 13(3):e0194895. doi:10.1371/journal.pone.0194895 [1-14] (2018).
Joung et al., Genome-scale activation screen identifies a lncRNA locus regulating a gene neighborhood. Nature 548(7667): 343-346 (2017).
Joung et al., Genome-scale CRISPR-Cas9 knockout and transcriptional activation screening. Nature Protocols 12(4): 828-863 (2017).
Kearns et al., Cas9 effector-mediated regulation of transcription and differentiation in human pluripotent stem cells. Development 141(1):219-223 (2014).
Kim et al.: Direct reprogramming and biomaterials for controlling cell fate. Biomater Res. 20:39 doi:10.1186/s40824-016-0086-y [1-12] (2016).
Kim et al., Highly efficient RNA-guided bases editing in mouse embryos. Nat Biotech 35: 435-437 (2017).
Konermann et al., Genome-scale transcriptional activation by an engineered CRISPR-Cas9 complex. Nature 517(7536): 583-588 (2015).
Kukurba et al.: RNA Sequencing and Analysis. Cold Spring Harbor Protocols. 2015(11):951-969 doi:10.1101/pdb.top084970 (2015).
Larson et al., CRISPR interference (CRISPRi) for sequence-specific control of gene expression. Nature Protocols 8(11): 2180-2196 (2013).
Lavon et al.: The effect of overexpression of Pdx1 and Foxa2 on the differentiation of human embryonic stem cells into pancreatic cells. Stem Cells 24(8):1923-1930 doi:10.1634/stemcells.2005-0397 (2006).
Liao et al., In Vivo Target Gene Activation via CRISPR/Cas9-Mediated Trans-epigenetic Modulation. Cell 171(7):1495-1507 (2017).
Liu et al., CRISPR-Based chromatin remodeling of the endogenous Oct4 or Sox2 locus enables reprogramming to pluripotency. Cell Stem Cell 22: 252-261 (2018).
Luisi et al.: Expression and secretion of activin A: possible physiological and clinical implications. Luisi et al. 2001 European Journal of Endocrinology 145(3):225-236 (2001).
Lukianova-Hleb et al.: All-in-one processing of heterogeneous human cell grafts for gene and cell therapy. Mol Ther Methods Clin Dev. 3:16012 DOI:10.1038/mtm.2016.12 [1-8] (2016).
Lummertz Da Rocha et al., Reconstruction of complex single-cell trajectories using CellRouter. Nature Comm 9:892 [1-13] (2018).
Mahfouz et al. Targeted transcriptional repression using a chimeric TALE-SRDX repressor protein. Plant Mol Biol (2012) 78:311-321. Published online: Dec. 14, 2011.
Mali et al., CAS9 transcriptional activators for target specificity screening and paired nickases for cooperative genome engineering. Nat Biotech 31(9): 833-838 (2013).
Malik et al.: A review of the methods for human iPSC derivation. Methods Mol Biol. 997:23-33 (2013).
Manno et al., Molecular Diversity of Midbrain Development in Mouse, Human and Stem Cells. Cell 167(2):566-580 (2016).
Mircetic et al., Purified Cas9 fusion proteins for advanced genome manipulation. Small Methods 1(4): 1600052 (2017).
Nissim et al.: Multiplexed and programmable regulation of gene networks with an integrated RNA and CRISPR/Cas toolkit in human cells. Molecular Cell 54(4):698-7l0 (2014).
Ohl et al.: Detachment and sonoporation of adherent HeLa-cells by shock wave-induced cavitation. Biochim Biophys Acta. 1624(1-3):131-138 (2003).
Ong et al.: Optimised metrics for CRISPR-KO screens with second-generation gRNA libraries. Sci Rep. 7(1):7384 doi:10.1038/s41598-017-07827-z [1-10] (2017).
PCT/US2018/048349 International Search Report and Written Opinion dated Oct. 29, 2018.
PCT/US2019/028352 International Search Report and Written Opinion mailed Aug. 27, 2019.
PCT/US2019/059874 International Search Report and Written Opinion dated Mar. 18, 2020.
Perez-Pinera et al.: RNA-guided gene activation by CRISPR-Cas9-based transcription factors. Nature Meth 10(10):973-976 (2013).
Qi et al. Repurposing CRISPR as an RNA-guided platform for sequence-specific control of gene expression. Cell 152:1173-1183 (2013).
Rees et al., Improving the DNA specificity and applicability of base editing through protein engineering and protein delivery. Nat Comm 8: 15790 (2017).
Saklayen et al., Intracellular delivery using nanosecond-laser excitation of large-area plasmonic substrates. ACS Nano 11: 3671-3680 (2017).
Sasaki et al.: Label-free morphology-based prediction of multiple differentiation potentials of human mesenchymal stem cells for early evaluation of intact cells. PLoS One 9(4):e93952 doi:10.1371/journal.pone.0093952 [1-14] (2014).
Shmakov et al. Discovery and Functional Characterization of Diverse Class 2 CRISPR-Cas Systems. Mol Cell 60(3):385-397 (2015).
Soldner et al. Parkinson's disease patient-derived induced pluripotent stem cells free of viral reprogramming factors. Cell 136, 964-977 (2009).
Somers et al.: Generation of transgene-free lung disease-specific human induced pluripotent stem cells using a single excisable lentiviral stem cell cassette. Stem Cells 28(10):1728-1740 (2010).
Sommer et al.: Induced pluripotent stem cell generation using a single lentiviral stem cell cassette. Stem Cells 27(3):543-549 (2009).
Stoppel et al.: Electrical and mechanical stimulation of cardiac cells and tissue constructs. Adv Drug Deliv Rev. 96:135-155 (2016).

(56) References Cited

OTHER PUBLICATIONS

Tak et al., Inducible and multiplex gene regulation using CRISPR-Cpf1-based transcription factors. Nat Meth 14(12): 1163-1166 (2017).
Tanenbaum et al., A Protein-tagging system for signal amplification in gene expression and fluorescence imaging. Cell 159(3): 635-646 (2014).
Weltner et al., Human pluripotent reprogramming with CRISPR activators. Nat Comm 9: 2643 (2018).
Wong, et al. Multiplexed Barcoded CRISPR-Cas9 Screening Enabled by CombiGEM. PNAS. Mar. 1, 2016, vol. 113, pp. 2544-2549.
Wust et al.: Controlled positioning of cells in biomaterials-approaches towards 3D tissue printing. J. Funct Biomater. 2(3):119-154 (2011).
Yi et al.: Engineering of TEV protease variants by yeast ER sequestration screening (YESS) of combinatorial libraries. Proc Natl Acad Sci USA 110(18):7229-7234 (2013).
Yoshioka et al.: Development of a mono-promoter-driven CRISPR/Cas9 system in mammalian cells. Sci Rep. 5:18341. doi:10.1038/srep18341 [1-8] (2015).
Yuan et al.: Cell membrane deformation and bioeffects produced by tandem bubble-induced jetting flow. Proc Natl Acad Sci USA 112(51):E7039-E7047 (2015).
Zandstra et al.: A ligand-receptor signaling threshold model of stem cell differentiation control: a biologically conserved mechanism applicable to hematopoiesis. Blood 96(4):1215-1222 (2000).
Kulik et al.: Parallelization in automated stem cell culture. 3rd CIRP Conference on BioManufacturing, Procedia CIRP 65:242-247 (2017).
EP Application No. 19882546.5 Supplemental Extended European Search Report dated Oct. 7, 2022.
U.S. Appl. No. 17/688,837 Final Office Action dated Oct. 5, 2022.
U.S. Appl. No. 17/688,857 Final Office Action dated Oct. 14, 2022.
U.S. Appl. No. 17/688,859 Final Office Action dated Sep. 27, 2022.
U.S. Appl. No. 17/688,861 Final Office Action dated Nov. 7, 2022.
Aasen et al.: Isolation and cultivation of human keratinocytes from skin or plucked hair for the generation of induced pluripotent stem cells. Nat Protoc. 2010 5(2):371-382 doi:10.1038/nprot.2009.241 (2010).
Ahmed et al.: In situ self-assembly of gold nanoparticles on hydrophilic and hydrophobic substrates for influenza virus-sensing platform. Sci Rep. 7:44495: 1-11 doi:10.1038/srep44495 (2017).
Ban et al.: Efficient generation of transgene-free human induced pluripotent stem cells (iPSCs) by temperature-sensitive Sendai virus vectors. Proc Natl Acad Sci USA 108(34):14234-14239 doi:10.1073/pnas.1103509108 (2011).
Bar-Nur et al. Epigenetic memory and preferential lineage-specific differentiation in induced pluripotent stem cells derived from human pancreatic islet Beta cells. Cell Stem Cell 9:17-23 (2011).
Chen et al.: Nanofabrication by electron beam lithography and its applications: A review. Microelectronic Engineering 135:57-72 https://doi.org/10.1016/j.mee.2015.02.042 (2015).
Drews et al.: The cytotoxic and immunogenic hurdles associated with non-viral mRNA- mediated reprogramming of human fibroblasts. Biomaterials 33(16):4059-4068 doi:10.1016/j.biomaterials.2012.02.025 (2012).
Drozd et al., Generation of Human iPSCs From Cells of Fibroblastic and Epithelial Origin by Means of the oriP/EBNA-1 Episomal Reprogramming System. Stem Cell Res Ther 6 (1): 122 (2015).
Gill et al.: Progress and prospects: the design and production of plasmid vectors. Gene Ther. 16(2):165-171 doi:10.1038/gt.2008.183 (2009).
He et al.: Single-shot aperture-scanning Fourier ptychography. Opt Express 26(22):28187-28196 doi:10.1364/OE.26.028187 (2018).
Hu et al.: Fluorescence in situ hybridization (FISH): an increasingly demanded tool for biomarker research and personalized medicine. Biomark Res. 2:3:1-13 doi: 10.1186/2050-7771-2-3 (2014).
Hudin et al.: Localized Tactile Stimulation by Time-Reversal of Flexural Waves: Case Study With a Thin Sheet of Glass. IEEE World Haptics Conference, pp. 1-6 DOI:10.1109/WHC.2013.6548386 (2013).

Jingshan et al.: Transport of Intensity phase imaging by intensity spectrum fitting of exponentially spaced defocus planes. Opt Express. 22(9):10661-10674 doi:10.1364/OE.22.010661 (2014).
Jo et al.: Quantitative Phase Imaging and Artificial Intelligence: A Review. IEEE Journal of Selected Topics in Quantum Electronics 25(1):1-14 (2019).
Kashyap et al.: Selective local lysis and sampling of live cells for nucleic acid analysis using a microfluidic probe. Sci Rep. 6:29579:1-10 doi:10.1038/srep29579 (2016).
Kim et al.: Generation of human induced pluripotent stem cells by direct delivery of reprogramming proteins. Cell Stem Cell 5;4(6):472-476 doi:10.1016/j.stem.2009.05.005 (2009).
Kim et al.: Generation of human induced pluripotent stem cells from osteoarthritis patient-derived synovial cells. Arthritis Rheum 63(10):3010-3021 doi:10.1002/art.30488 (2011).
Lee et al.:Single-shot phase retrieval via Fourier ptychographic microscopy. Optica 5(8):976-983 https://doi.org/10.1364/OPTICA.5.000976 (2018).
Li et al.: Excitable networks controlling cell migration during development and disease. Semin Cell Dev Biol. 100:133-142 doi:10.1016/j.semcdb.2019.11.001 (2020).
Loh, et al. Reprogramming of T Cells from Human Peripheral Blood. Cell Stem Cell. Jul. 2, 2010; 7(1): 15-19.
Lopatynskyi et al.: Au nanostructure arrays for plasmonic applications: annealed island films versus nanoimprint lithography. Nanoscale Res Lett. 10:99: 1-9 doi:10.1186/s11671-015-0819-1 (2015).
Mann: Rapid isolation of antigen-specific clones from hybridoma fusions. Nat Methods 4, i-ii URL:https://doi.org/10.1038/nmeth1028 (2007).
Okita et al.: A more efficient method to generate integration-free human iPS cells. Nat Methods 8(5):409-412 doi:10.1038/nmeth.1591 (2011).
Okita et al.: Generation of mouse-induced pluripotent stem cells with plasmid vectors. Nature Protocols 5(3):418-428 (2010).
PCT/US2022/019196 International Search Report and Written Opinion dated Jun. 1, 2022.
Rim et al.: Chondrogenic Differentiation from Induced Pluripotent Stem Cells Using Non-Viral Minicircle Vectors. Cells 9(3):582:1-21 doi:10.3390/cells9030582 (2020).
Sanchez-Esquivel et al.: Spectral dependence of nonlinear absorption in ordered silver metallic nanoprism arrays. Sci Rep. 7(1):5307:1-9 doi:10.1038/s41598-017-04814-2 (2017).
Segalman: Patterning with block copolymer thin films. Materials Science and Engineering R Reports 48(6):191-226 DOI:10.1016/j.mser.2004.12.003 (2005).
Skorik et al.: Xeno-Free Reprogramming of Peripheral Blood Mononuclear Erythroblasts on Laminin-521. Curr Protoc Stem Cell Biol. 52(1):e103:1-41 doi:10.1002/cpsc.103 (2020).
Stewart et al.: Intracellular Delivery by Membrane Disruption: Mechanisms, Strategies, and Concepts. Chem Rev. 118(16):7409-7531 doi:10.1021/acs.chemrev.7b00678 (2018).
Takahasi et al.: Induction of pluripotent stem cells from adult human fibroblasts by defined factors. Cell 131(5):861-872 doi:10.1016/j.cell.2007.11.019 (2007).
Thiers: Dermatology and Dermatologic Surgery. Chapter 15—Miscellaneous Topics in Clinical Dermatology, Elsevier—Health Sciences Division, pp. 302-303 (2008).
Tvarozek et al.: Plasmonic behaviour of sputtered Au nanoisland arrays. Applied Surface Science 395:241-247 DOI:10.1016/j.apsusc.2016.04.183 (2017).
U.S. Appl. No. 17/688,837 Non-Final Office Action dated May 26, 2022.
U.S. Appl. No. 17/688,854 Non-Final Office Action dated May 11, 2022.
U.S. Appl. No. 17/688,857 Non-Final Office Action dated Jun. 9, 2022.
U.S. Appl. No. 17/688,859 Non-Final Office Action dated Jun. 10, 2022.
U.S. Appl. No. 17/688,861 Non-Final Office Action dated Jun. 24, 2022.
Warren et al., Highly efficient reprogramming to pluripotency and directed differentiation of human cells with synthetic modified mRNA. Cell Stem Cell 7(5):618-630 (2010).

(56) References Cited

OTHER PUBLICATIONS

Watt et al.: Ion beam lithography and nanofabrication: A review. International Journal of Nanoscience 4(3):269-286 DOI:10.1142/S0219581X05003139 (2005).
Yoshioka et al.: Efficient generation of human iPSCs by a synthetic self-replicative RNA. Cell Stem Cell 13(2):246-254 doi:10.1016/j.stem.2013.06.001 (2013).
Zheng et al.: Concept, implementations and applications of Fourier ptychography. Nature Physics Reviews 3(3):207-223 DOI:10.1038/s42254-021-00280-y (2021).
Zhou et al.: Generation of induced pluripotent stem cells from urine. J Am Soc Nephrol. 22(7):1221-1228 doi:10.1681/ASN.2011010106 (2011).
Zhou et al.: Integration-free Methods for Generating Induced Pluripotent Stem Cells. Genomics, Proteomics & Bioinformatics 11(5):284-287 (2013).
Zhou et al.: Si surface passivation by SiOx : H films deposited by a low-frequency ICP for solar cell applications. Journal of Physics D Applied Physics 45(39):395401, pp. 1-8 DOI:10.1088/0022-3727/45/39/395401 (2012).
Zou et al.: High-resolution transport-of-intensity quantitative phase microscopy with annular illumination. arXiv:1704.04091v3 [physics.optics], pp. 1-25 doi:10.48550/ARXIV.1704.04091 (2017).
Zou et al.: High-resolution transport-of-intensity quantitative phase microscopy with annular illumination. Sci Rep. 7(1):7654, pp. 1-22 doi:10.1038/s41598-017-06837-1 (2017).
Zuo et al.: Transport of intensity equation: a tutorial. Optics and Lasers in Engineering 135(106187):1-98 URL:https://doi.org/10.1016/j.optlaseng.2020.106187 (2020).
U.S. Appl. No. 17/688,837 Non-Final Office Action dated Apr. 6, 2023.
U.S. Appl. No. 17/688,854 Non-Final Office Action dated Apr. 21, 2023.
U.S. Appl. No. 17/688,861 Non-Final Office Action dated May 11, 2023.
U.S. Appl. No. 18/061,811 Final Office Action dated Apr. 21, 2023.
Co-pending U.S. Appl. No. 18/391,002, inventors Wagner; Matthias et al., filed Dec. 20, 2023.
Co-pending U.S. Appl. No. 18/391,053, inventors Wagner; Matthias et al., filed Dec. 20, 2023.
Kogler et al.: Comparison of time-gated surface-enhanced raman spectroscopy (TG-SERS) and classical SERS based monitoring of *Escherichia coli* cultivation samples. Biotechnol Prog. 34(6):1533-1542 doi:10.1002/btpr.2665 (2018).
Meier et al.: Fast electrically assisted regeneration of on chip SERS substrates. Lab on a Chip 15:2923-2927 DOI:10.1039/C5LC00397K (2015).
PCT/US2022/042811 International Search Report and Written Opinion dated Nov. 22, 2022.
U.S. Appl. No. 17/688,854 Final Office Action dated Aug. 1, 2023.
U.S. Appl. No. 17/688,861 Final Office Action dated Oct. 12, 2023.
U.S. Appl. No. 17/930,413 Final Office Action dated May 26, 2023.
U.S. Appl. No. 17/930,413 Non-Final Office Action dated Jan. 26, 2023.
U.S. Appl. No. 17/930,413 Non-Final Office Action dated Nov. 30, 2022.
U.S. Appl. No. 17/930,413 Office Action dated Aug. 25, 2023.
U.S. Appl. No. 18/190,775 Final Office Action dated Jan. 12, 2024.
U.S. Appl. No. 18/190,775 Office Action dated Oct. 5, 2023.
U.S. Appl. No. 18/339,779 Office Action dated Mar. 13, 2024.
U.S. Appl. No. 18/061,811 Office Action dated Aug. 15, 2023.
U.S. Appl. No. 18/190,775 Office Action dated Apr. 24, 2024.
U.S. Appl. No. 18/391,002 Office Action dated Jul. 25, 2024.
U.S. Appl. No. 18/391,002 Office Action dated Oct. 31, 2024.
U.S. Appl. No. 18/061,811 Non-Final Office Action dated Jan. 12, 2023.
U.S. Appl. No. 18/391,002 Office Action dated Apr. 10, 2025.

Inducible dCas9 directly linked to first wave of 2 gRNAs + Cassette 2/+: inducible gRNAs Transcription inhibition by promoter-hairpin-loop complex

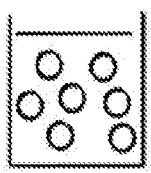
FIG. 30A
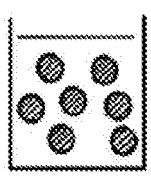
FIG. 30F
FIG. 30B
FIG. 30G
FIG. 30K
FIG. 30C
FIG. 30H
FIG. 30L
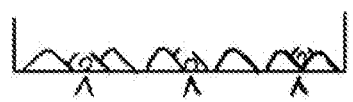
FIG. 30D
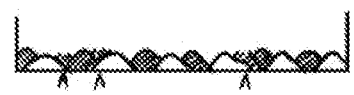
FIG. 30I
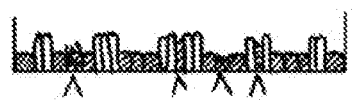
FIG. 30M
FIG. 30E
FIG. 30J
FIG. 30N
FIG. 31
FIG. 32

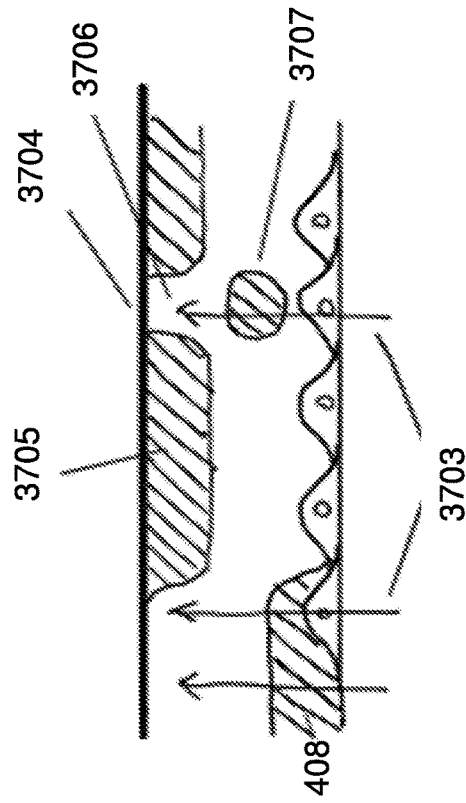
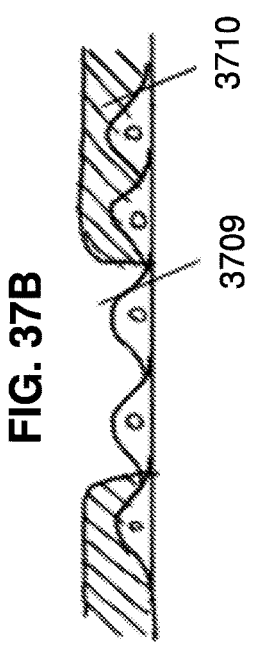
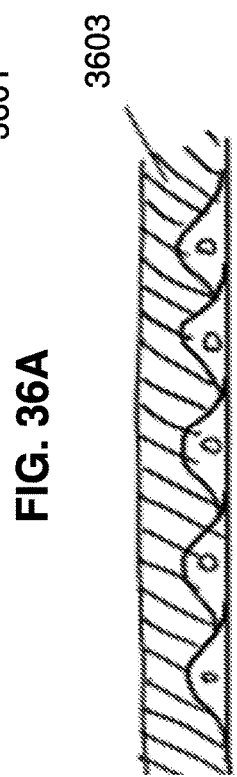
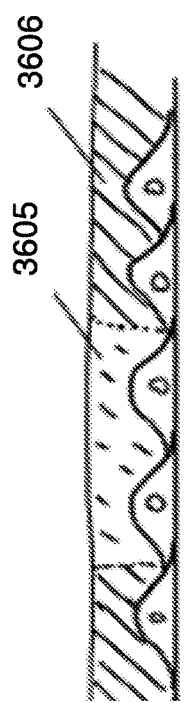

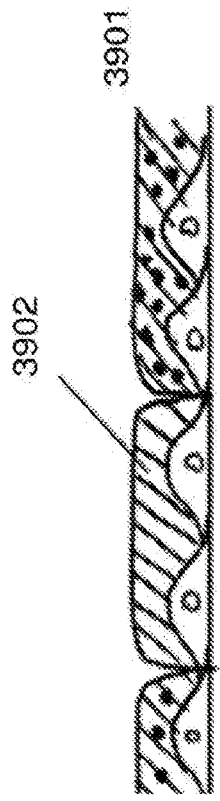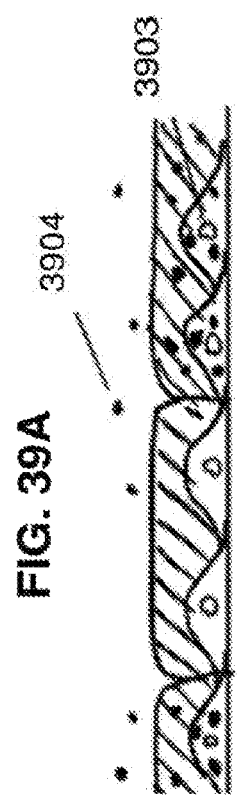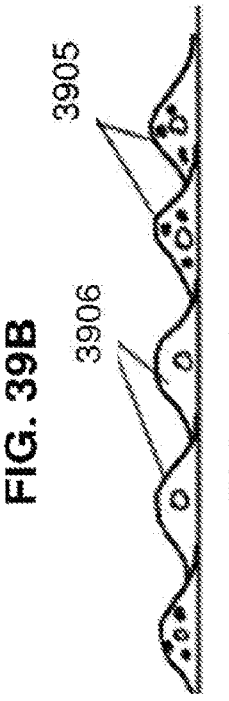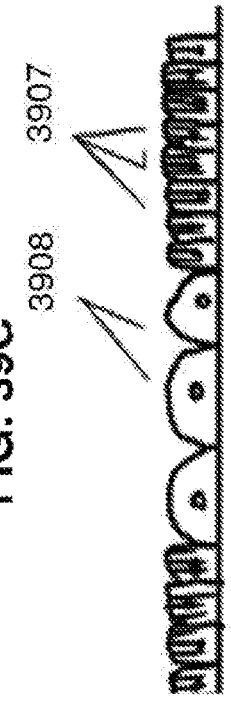
FIG. 39A  FIG. 39B  FIG. 39C  FIG. 39D
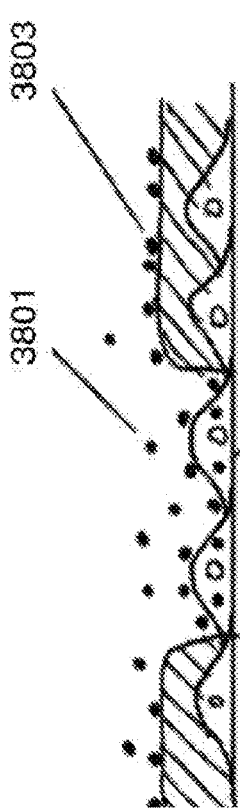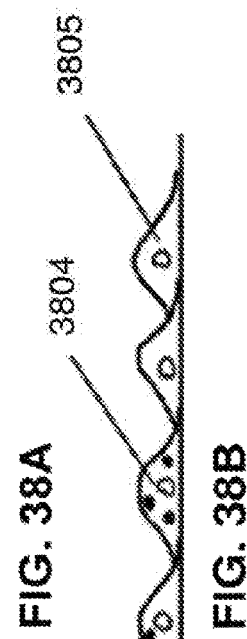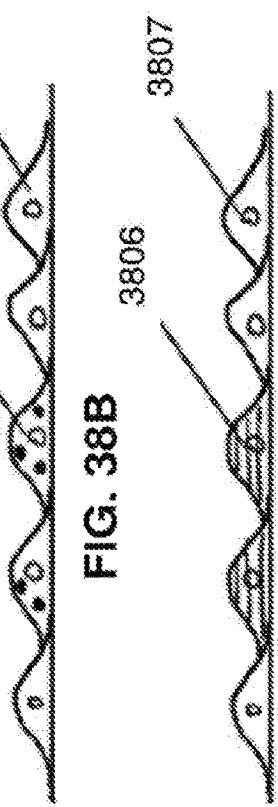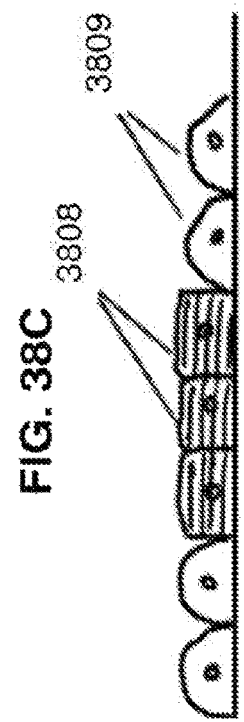
FIG. 38A  FIG. 38B  FIG. 38C  FIG. 38D

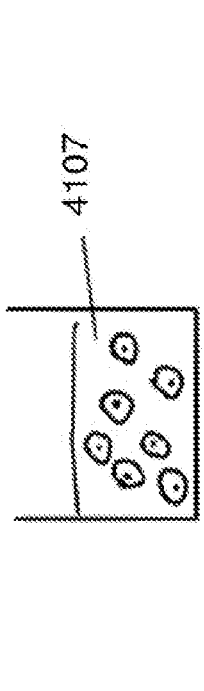
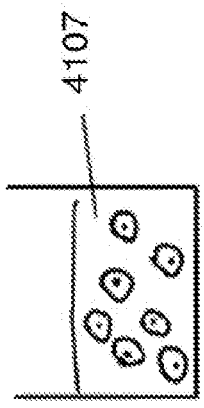
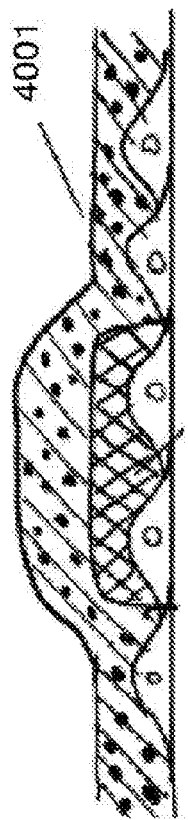
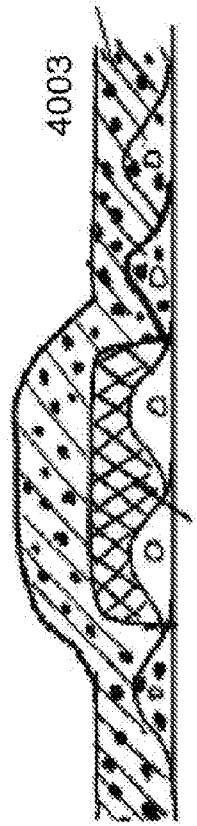
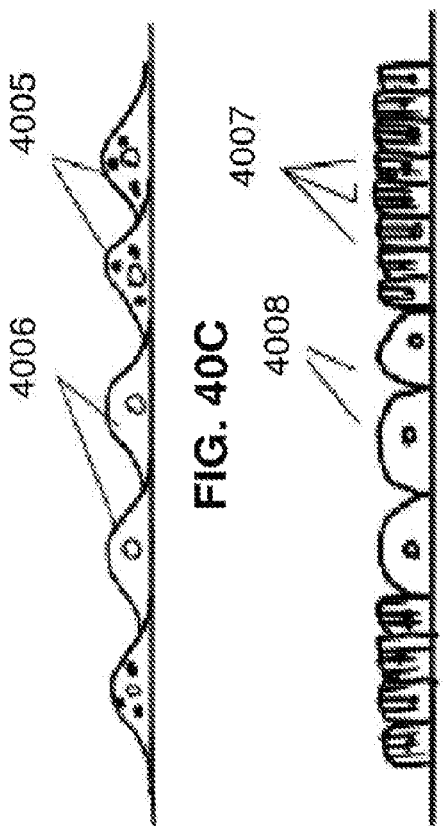

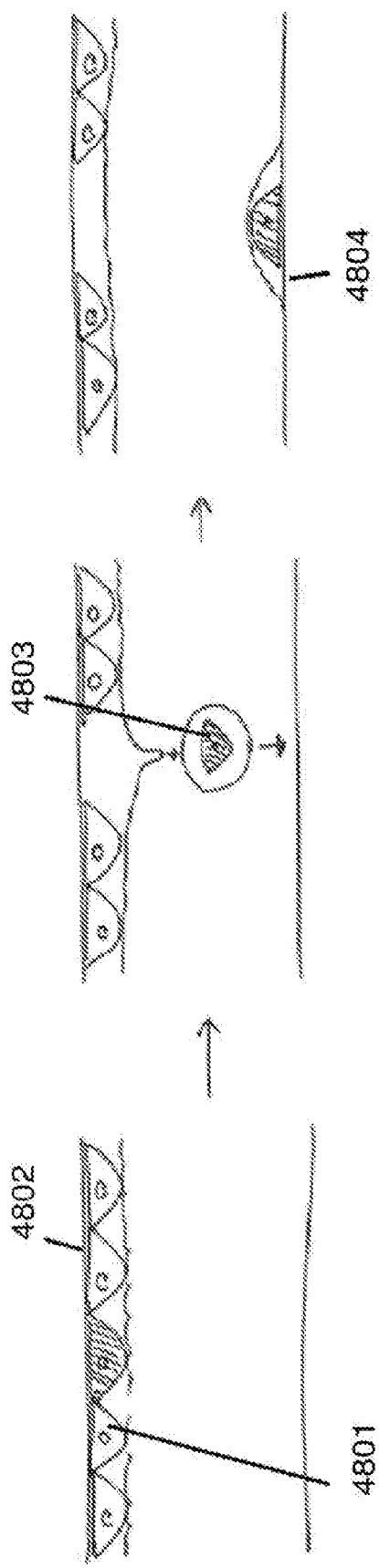
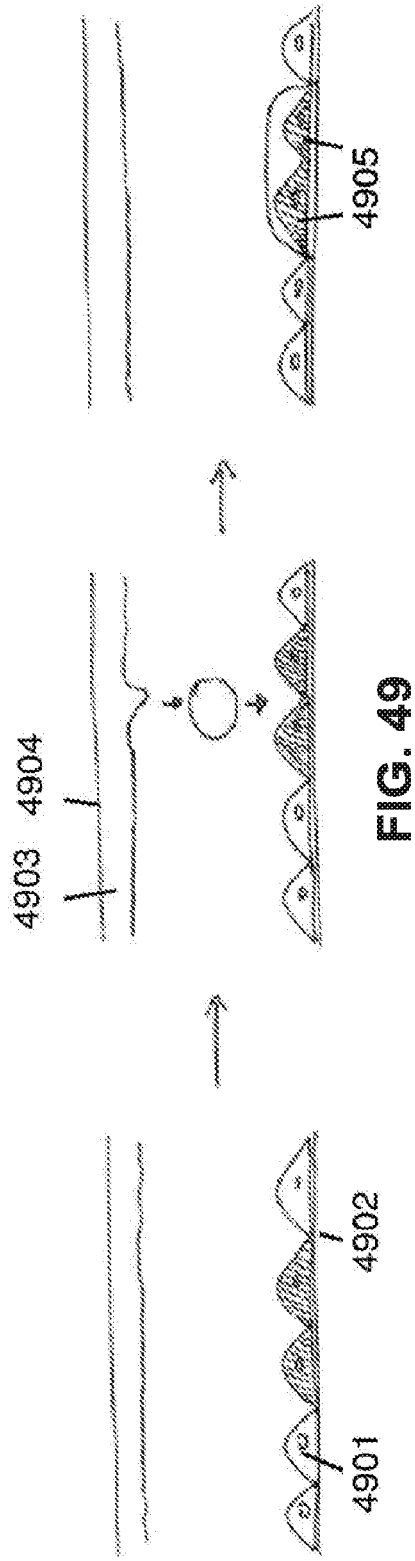

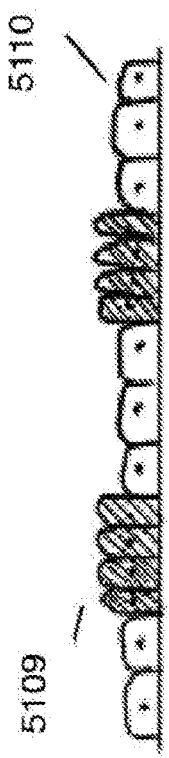
FIG. 51A
FIG. 51B
FIG. 51C
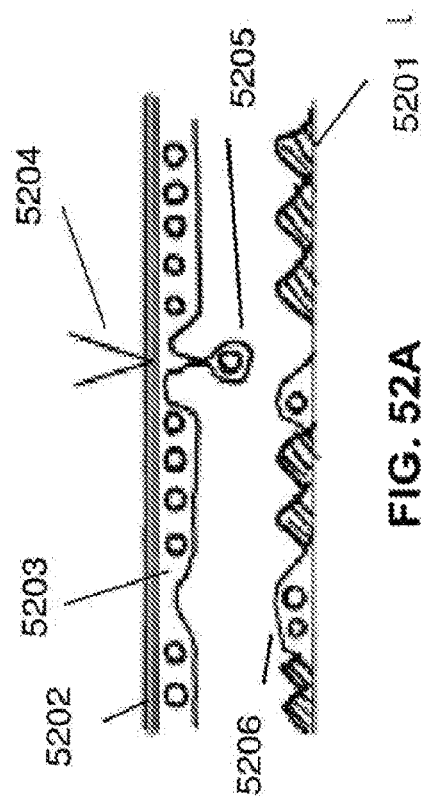
FIG. 51D
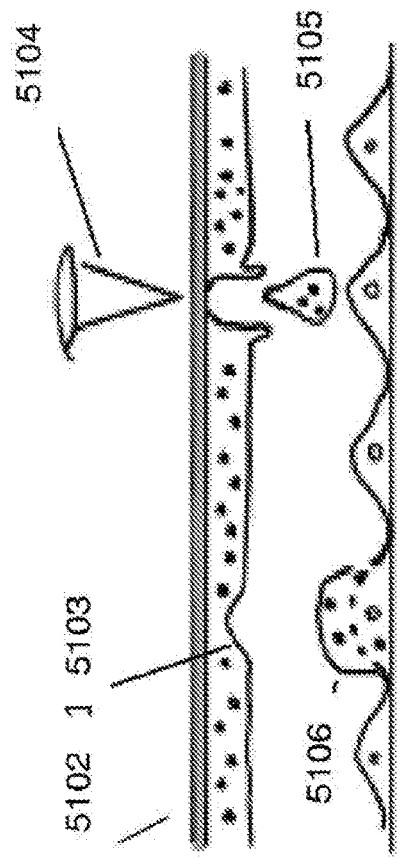
FIG. 52A
FIG. 52B
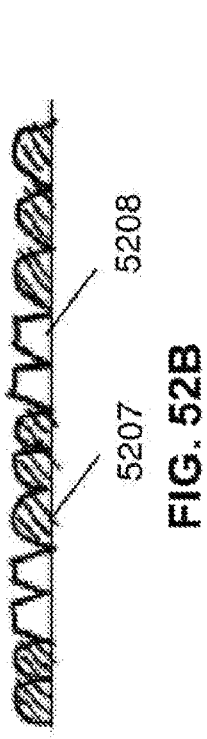

SYSTEMS FOR CELL CONTROL

CROSS-REFERENCE TO RELATED APPLICATIONS

This application is a U.S. National Phase entry of International Application No. PCT/US2019/059874, filed on Nov. 5, 2019, which claims priority to U.S. Provisional Application No. 62/756,520, filed Nov. 6, 2018; U.S. Provisional Application No. 62/928,076, filed Oct. 30, 2019; U.S. Provisional Application No. 62/928,078, filed Oct. 30, 2019; U.S. Provisional Application No. 62/928,081, filed Oct. 30, 2019; and U.S. Provisional Application No. 62/841,944, filed May 2, 2019, all incorporated by reference herein.

TECHNICAL FIELD

The disclosure relates to systems for cell control.

BACKGROUND

The cell is the basic unit of known life. Bacteria, humans, plants, and animals are all organized as genomes packaged within cells, exhibiting the ability to metabolize nutrients and copy genetic material. For medicine and biology to advance, researchers must be able to manipulate and study cellular life. Early research into cellular growth and phenotypes yielded tools that are in use to this day. For example, agar plates, nutrient broths, and aseptic techniques have a long history of use in research laboratories and medicine to study biological phenomena.

There have been some remarkable advances in research tools. For example, polyacrylamide gel electrophoresis, fluorescent proteins, and DNA sequencing have each been used to reveal volumes of information about cells and their properties. However, certain paradigmatic constraints persist in biology and medicine. For example, by-and-large, cells are understood to be something to be grown and studied in large volumes of culture. Genetic manipulation typically proceeds in step-wise fashion. A gene may first be cloned into a plasmid, which can then be transfected into cells by electroporation or lipofection. Recent discoveries that clustered, regularly interspersed short palindromic repeats (CRISPR) in bacteria were associated with certain proteins revealed a CRISPR-Associated (Cas) endonuclease that operates as an RNA-guided DNA endonuclease. Mutated version of Cas endonuclease (dCas) work as RNA-guided DNA proteins that can be complexed with guide RNA to bind to DNA segments that are complementary to a corresponding section of the guide RNA. Molecular discoveries such as Cas endonuclease and dCas promise to be valuable in revealing much more information from living cells.

SUMMARY

The disclosure provides methods and systems for growing cells, directing cells to grow into specified cell types, genetically and physically manipulating cells, and addressing one or more individual cells within a mixed cell population. Aspects of the disclosure relate to vectors useful to induce developmental changes in cells, in which those vectors have a temporal component. Vectors of the disclosure encode a controllable, temporal series of events. Once the vectors are delivered into target cells, a series of discrete and different genetic events may be induced. The disclosed methods generally provide for the temporal encoding of multiplex genetic effectors in vector format for cell state transitions.

Related aspects of the disclosure use fluorescent reporters, imaging, and image-guided laser ablation to culture mixed populations of cells and selectively remove subpopulations of certain cells. Such methods allow cells to be grown in mixed, heterogeneous populations, which may be beneficial where one cell type secretes material essential to growth of another cell type. Image-guided laser ablation allows the first "helper cell" type to be selectively removed once the culture is mature. Such techniques generally provide systems and methods for heterogeneous cell culture control.

Other related aspects of the disclosure relate to a processing system that uses imaging and lasers to spatially address individual cells and selections of cells in mixed populations. The optical processing is useful to deliver cargos such as the temporal vectors as well as to selectively monitor or remove such cells. Such systems generally provide optical cell processors and related methods.

Further related aspects of the disclosure relate to cell manipulation techniques rooted in photolithography concepts. Photolithography approaches are used to create spatial masks to protect or ablate sets of cells or to build up controlled layers of different cell types and biological materials. Such approaches generally provide photolithographic systems for cell culture control and measurement.

The disclosure also includes laser-based methods to selectively transfer cargo into individual cells, onto individual cells, or to selectively transfer individual cells onto a target surface ("bioprinting"). Material of interest is dispersed in a film over a planar donor substrate, which is disposed facing a receiving substrate. A laser scans the donor substrate, energizing the film resulting in the material being transferred forward onto the receiving substrate. Computer imaging and control provides for precise spatial modulation with respect to both the donor and receiving substrates. Such systems and methods generally provide for cell manipulation using laser-induced forward transfer.

Aspects of the disclosure provide a vector for triggering differentiation of a desired cell state. The vector includes at least one cassette that includes at least one inducible, cell-type specific or constitutively active promoter, and a segment encoding at least one gene modulating complex. The vector may also encode fluorescent reporters that, when expressed, fluoresce to show cells that have received and are expressing the vector. In one embodiment the constitutively active promoter is expressed continuously, the upon addition of a drug or enzyme the gene modulating complex is expressed, leading to differentiation. In one embodiment, the cell-type specific and inducible promoters are only expressed in the presence of an inducing agent or once the cell is at the right differentiation stage and wherein expression of the cassette results in differentiation of a cell into which the vector is introduced into a desired cell state. The inducing agent may be a small molecule; a nucleotide; and a peptide aptamer. The promoter is selected from the group consisting of RNA polymerase II and III promoters. The vector preferably includes a plurality of cassettes under control of a common inducible promoter. Preferably, the vector comprises a plurality of said cassettes, each under control of a different inducible promoter. Each inducible promoter may be induced by delivery of one of tetracycline, doxycycline, lactose, rapamycin, and RU486.

In some embodiments, the gene modulating complex comprises a Cas protein. Preferably, the vector is present in a cell such as a differentiated cell or an un-differentiated cell such as an induced pluripotent stem cell (iPSC).

In certain embodiments, the vector provides a temporal sequence of effects on the cell by means of a first coding sequence and a second coding sequence each coding for protein that modulates transcription. Any number of coding sequences (one, two, three, four, five, more . . . ) may be included and each may be expressed at different times. Each protein may be a CRISPR activator or inhibitor (CRISPRa/i) complex; a TALE transcriptional activator or inhibitor (TALEa/i) complex; a zinc finger activator or inhibitor (ZFa/i) complex; or a transcription factor. Each protein that modulates transcription may effect one or more genes in a genome of the cell. For example, the genes, once expressed, may direct the cell to differentiate to a specific cell type or direct the cell to de-differentiate into a stem cell. The temporal sequence may be achieved by delivery of two different agents, at different times. Each agent may be selected from the group consisting of tetracycline, doxycycline, lactose, rapamycin, and RU486.

In some embodiments, the cell is a fibroblast. The vector responds to an agent to express a protein that upregulates expression of one or more of Oct4, Klf4, Sox2, and c-Myc thereby de-differentiating the fibroblast into a stem cell. Optionally, a second agent is later delivered to cause the vector to express a second protein that upregulates a second set of transcription factors. For example the second set of transcription factors may include one or more of Pdx1, Ngn3, and Mafa and differentiate the stem cell into a beta cell.

Other aspects of the disclosure provide a method for differentiating a cell to a specific state. The method includes delivering a vector to a cell. The vector includes one or more expression cassettes, each cassette comprising at least one segment encoding a binding protein, and at least one inducible promoter for activating or inhibiting expression of the at least one binding protein. The method further includes triggering differentiation of the cell to a desired cell state by inducing expression of the binding protein, whereby the binding protein activates or inactivates expression of at least one transcription factor in the cell.

In some embodiments, the binding protein comprises dCas and the vector further encodes at least one guide ribonucleic acid (gRNA) that guides the dCas to a regulatory sequence of the transcription factor. The cell may be included in a culture on a surface of a substrate. The method may include using laser removal to remove cells from the surface. Optionally, laser removal uses a laser operable to scan over the surface, under control of an analysis system linked to an imaging system that images the surface, wherein at least some organisms in the culture include fluorescent reporters.

In certain embodiments, the culture comprises a heterogeneous cell comprising at least a first cell type and a second cell type, wherein at least members of the first cell type are driven by the vector. Laser removal (e.g., removal achieved through pulsed laser cavitation) may be used to define a ratio of the first cell type to the second cell type within the culture. Pulsed laser cavitation may be achieved through the use of an absorbing element forming part of the substrate. The absorbing element may be an absorbing surface on the substrate. The absorbing element may include a nanoparticle mixed into the cell media; or a dye mixed into the cell media.

The method may include optically patterning the first cell type and the second cell type onto the surface. Optically patterning the cells may include laser-induced forward transfer of cells onto the substrate. In some embodiments, optically patterning the cells includes formation of a temporary hydrogel mask formed over a cell culture for the purpose of controlling delivery of the ieVector in a specific pattern. Delivery may be achieved by lipofection in areas not covered by the mask; electroporation in the areas not covered by the mask; or viral delivery in the areas not covered by the mask.

The method may include delivering the vector to the cell by optical means such as pulsed laser cavitation where the cavitation temporarily porates the target cell membranes for the purpose of vector delivery. The pulsed laser cavitation may achieved through the use of an absorbing element in the vicinity of the target cells. In LIFT embodiments, the optical means is by LIFT of material onto the substrate to deliver the vector. LIFT may be used to porate the target cell membranes for the purpose of vector delivery or to eject a hydrogel loaded with the vector in a patterned manner onto cell culture for selective delivery. The vector may be delivered in a pattern by the optical means, the pattern controlled by a computing system, based on an image of the receiving cell culture, the method further comprising selective laser removal to remove vector-less cells or adjust a ratio of cell types.

Other aspects of the disclosure provide a system for heterogeneous cell culture control. The system includes a growth vessel; a first population of target cells adherent to a surface of the vessel in a spatial distribution; a second population of helper cells adherent to the surface; and an optical subsystem operable to identify and perform selective removal of individual helper cells.

Preferably, the optical subsystem includes an imaging system that takes an image of the spatial distribution; a computing system that receives the image from the imaging system; and laser under control of the computer system to perform the selective removal. The laser may include a pulsed laser targeting system operated by the computing system over time to dynamically manage distribution and patterning over the course of a tissue culture protocol.

In some embodiments, the helper cells provide chemical signals that promote differentiation, proliferation, or migration of the target cells. Alternatively, the helper cells provide optical signals to the target cells. In certain embodiments, the target cells are beta-cells and helper cells include mesenchymal stem cell that act as inflammation-reducing and pro-angiogenic agents. In other embodiments, the helper cells have image characteristics that are sufficiently distinct in a label-free imaging mode for the helper cells to be identified, managed, or removed without specific fluorescent labelling. The imaging mode may be brightfield, phase, differential interference contrast, or darkfield.

Aspects of the disclosure provide a photolithographic method for spatially patterning cells or materials in an adherent culture. Photolithographic methods include distributing a hydrogel over a culture surface; optically cross-linking portions of the hydrogel; removing un-treated hydrogel to leave a patterned mask over the surface; and distributing cells or materials over the surface according to the mask. The patterned mask may include radical chain photopolymerized poly(ethylene glycol) hydrogel functionalized with norbornene groups, degradable metalloproteinase peptide (MPP) linkers, and photoinitiator Irgacure 2959.

Optionally, the removing step comprises washing the hydrogel with cell media to create the patterned mask. The method may include removing the mask, e.g., by chemical degradation using a collagenase. In certain embodiments, the hydrogel comprises PEG-norbornene, MMP degradable peptide; and Irgacure 2959 photoinitiator in phosphate buffered saline or cell media solution. The mask may be formed on top of an adherent cell culture and used to protect a select subset of cells while unmasked cells are removed.

In certain embodiments, the mask is formed on top of a cell culture to cover cells that are not of interest and to allow for collection of un-masked cells. The hydrogel may include polyethylene glycol diacrylate (PEGDA) and photoinitiator Irgacure 2959, and wherein the optical cross-linking uses 365 nm light. In any embodiments, one or more of the cells may include a vector that encodes a temporal sequence of transcription regulation.

Other aspects of the disclosure provide a system for laser-induced forward transfer (LIFT) system. The system includes a donor surface; a receiving surface opposed to the donor surface; a laser scanning subsystem positioned to emit coherent light towards the donor surface; and an imaging subsystem positioned to receive light from the surfaces. The system preferably includes a controller system operable to receive an image of cells from the imaging subsystem and operate the laser scanning subsystem to use the coherent light to spatially address the donor surface in a pattern corresponding to the cells in the image. In bioprinting embodiments, the controller system detects fluorescence in in the image from cells expressing a vector with a fluorescent reporter and operates the laser scanning subsystem to spatially pattern the coherent light to thereby transfer the cells that contain the vector onto the receiving surface.

In certain embodiments, the donor surface is biocompatible and suitable for cell culture. The system may include a monolayer of adherent cells cultured on the receiving surface. The donor surface may be coated with an aqueous layer containing a cargo. In some embodiments, the donor surface comprises a material that responds to laser stimulation by transferring energy into the aqueous layer to thereby eject the cargo in a spatially-controllable manner. In certain embodiments, the donor surface is sufficiently transparent that cells on the surface can be imaged from the opposite side. Preferably, the donor surface comprises a material that absorbs laser light and transfer the energy to the aqueous layer. Operation of the system may perform (1) intracellular delivery of cargoes into cells via temporary stressing of the cell membrane, (2) ejection of selected cells onto a surface, or (3) ejection of biocompatible materials onto targeted cells. In some embodiments, the donor substrate includes: a surface that is sufficiently transmissive in the visible range to enable imaging, yet can also absorb laser light at a given wavelength and transfer it to the aqueous layer for the purpose of forming droplets. The receiving substrate may present a surface, positioned a distance d opposite the donor substrate for the purpose of receiving ejected materials. Preferably, the laser scanning subsystem includes a laser source and optical system for focusing and aligning the laser source onto the donor substrate or material coating the donor substrate.

BRIEF DESCRIPTION OF THE DRAWINGS

FIG. 27 shows an example embodiment of the present system
FIG. 30A shows a first cell type prepared for plating.
FIG. 30B shows the first cell type plated onto the cell culture surface.
FIG. 30C shows the first set of cells settles on the vessel.
FIG. 30D shows the removal process.
FIG. 30E shows an idealized post-removal cell distribution.
FIG. 30F shows a second cell type prepared in suspension.
FIG. 30G shows that the second cell type settles randomly into the culture vessel.
FIG. 30H shows that the cells then adhere to the surface.
FIG. 30I shows laser cell removal.
FIG. 30J shows a distribution resulting from laser cell removal.
FIG. 30K shows how cells proliferate and differentiate.
FIG. 30L shows the process of removal.
FIG. 30M shows further differentiation of cells.

FIG. 30N shows the final tissue.

FIG. 31 shows support cells in a transwell.

FIG. 32 shows helper cells in the well.

FIG. 36 shows patterned deposition of photo-cleavable polymers onto adherent cells.

FIG. 37A shows monolayer of cells that that will be masked by laser-induced forward transfer (LIFT) of hydrogel.

FIG. 37B shows the deposition of the hydrogel mask.

FIG. 37C shows the resulting mask.

FIG. 38A shows a cell culture with mask.

FIG. 38B shows masked cells not having cargo.

FIG. 38C shows that the interaction results in a differential effect on cells by mask.

FIG. 38D shows resultant cell differentiation.

FIG. 39A shows two masks of hydrogel.

FIG. 39B shows entry of the cargo.

FIG. 39C shows the cells after removal or degradation of hydrogels.

FIG. 39D shows an example final tissue.

FIG. 40A shows a second temporary hydrogel.

FIG. 40B shows that the cargo is delivered over a release time into the cells.

FIG. 40C shows a differential effect on the cells.

FIG. 40D shows resultant differential cell differentiation.

FIG. 41A shows selective application of a hydrogel mask.

FIG. 41B shows that unmasked cells are removed from the cell culture.

FIG. 41C shows result of removal of cells from the culture.

FIG. 41D shows collection of cells.

FIG. 48 shows cells cultured on the donor substrate for bioprinting.

FIG. 49 shows cells on the receiving substrate.

FIG. 51A shows a starting adherent cell culture.

FIG. 51B shows a pulsed laser illumination system used to eject liquid.

FIG. 51C shows the target cells after delivery.

FIG. 51D shows the diverse tissue with first cell type and second cell type.

FIG. 52A shows LIFT ejection to directly pattern vector-laden cells.

FIG. 52B shows the vector-patterned cells.

DETAILED DESCRIPTION

Figure 1:
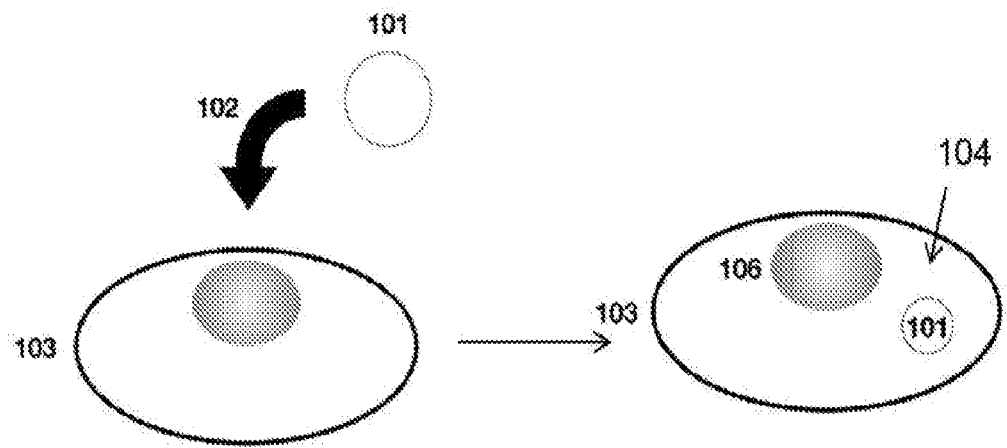
FIG. 1 shows vector.

The following disclosure describes and exemplifies (i) temporal encoding of multiplex genetic effectors in vector format for cell state transitions; (ii) systems and methods for heterogeneous cell culture control; (iii) optical cell processors; (iv) photolithographic systems for cell culture control and measurement; and (v) cell manipulation using laser-induced forward transfer.

I. Temporal Encoding of Multiplex Genetic Effectors in Vector Format for Cell State Transitions Aspects of the disclosure relate to creating a single-cell patterned cell monolayer by combining image-guided laser cell removal and cargo delivery tool (Optical Cell Processor, OCP) with genetic effectors in vector format for directing cell fate specification and/or tracking.

Methods and compositions of matter of how these cell fate programs can be encoded into a single vector to recapitulate desired differentiation trajectories towards a target cell state from a starting cell state upon temporally-specified induction are described. Various methods and systems for the discovery of the programs that mediate cell state transitions are described in: Directed cell fate specification via screening CRISPR/Cas genetic modulators; U.S. Provisional No. 62/660,577, filed Apr. 20, 2018; Directed cell fate specification and targeted maturation; U.S. Provisional No. 62/739,027, filed Sep. 28, 2018; Directed cell fate specification of cells with designer features; U.S. Provisional No. 62/754,605, filed Nov. 2, 2018; and System for generation of cell differentiation programs; U.S. Provisional No. 62/756,141, filed Nov. 6, 2018, all incorporated by reference.

Subsequent encoding of such cell programs into an inducible vector format enables transferability of the program and scalable production of its resulting cell product regardless of the means used to derive the program.

Methods of the disclosure are useful for transgene and synthetic gene activator/inhibitor-dependent lineage specification, as well as for the stepwise temporal control of multiplexed factors across two or more steps for the purposes of mediating cell state transitions utilizing a single vector. The disclosure provides tools useful to modify such adherent cultures at a single-cell level to create a patterned monolayer or to purify the culture from non-delivered or otherwise undesired cells.

Overexpression of a single transgene, myoblast determination protein 1 (MyoD), is capable of transdifferentiating fibroblasts to myoblasts. It is possible to simultaneously overexpress multiple factors to mediate cell fate transitions, including the use of only four factors—Oct4, Klf4, Sox2, c-Myc—to reprogram fibroblasts into induced pluripotent stem cells (iPSCs). It is also possible to achieve such cell programming effects in an inducible manner from a single vector construct, whether for the generation of iPSCs or other cell types from stem cells using transgenes or even synthetic gene activators. Though in these methods, transgene or synthetic activator/inhibitor-dependent cell fate transitions can be mediated from single or multiple constitutive promoters—or a single inducible promoter—across one or more vectors, none provide a means for imparting additional temporal specificity beyond a single step.

In order to achieve two-step temporal control over cell specification using genetic effectors, separate vectors may be introduced into human pluripotent stem cells (hPSCs):

one encoding a conditionally destabilized CRISPR activator (CRISPRa) complex, one constitutively expressing guide RNAs (gRNAs), and another carrying a drug-inducible transgene. In the presence of the appropriate lineage specifying media, cells carrying those constructs are first exposed to trimethoprim (TMP) day 3 to 9 of differentiation, which induces expression of a dCas9 activator with multimeric VP16 activation domains fused to a dihydrofolate reductase (DHFR)-derived destabilization domain (DD). The stabilized CRISPRa complex activates PDX1 and NKX6.1 expression using the constitutively expressed gRNAs. The cells are then exposed to doxycycline day 7 to 9 of differentiation to induce the expression of MAFA under the control of a TetON promoter. Together, that stepwise and overlapping genetic effector approach accelerates the differentiation of hPSCs into pancreatic progenitors when used in conjunction with lineage-specifying media.

However, that approach is limited by an inability to: (1) temporally induce activation of different CRISPRa targets as only the expression of the dCas9 activator complex can be controlled, (2) express multiple transgenes under different inducible promoters, and (3) integrate all genetic effector functions into a single vector construct.

The disclosure provides methods and compositions of two methods: (1) cell fate programs encoded into a single vector to recapitulate stepwise cell state transitions towards a target cell state from a starting cell state upon temporally specified induction of genetic effectors; and (2) cargo delivery and cell culture patterning with OCP of a culture manipulated with cell fate or other vector, based on fluorescently tagged or morphologically distinguishable subpopulations of cells.

These vectors and tags can be delivered to the cells at a single-cell resolution with laser described within this patent, or they can be delivered by methods previously described by others (lipofection, electroporation, nucleofection, viral infection). Regardless of the method of delivery, the vector-modified cell culture can be further tailored by using the OCP described in this innovation to remove cells at single cell level to pattern desired cell types within the same culture.

Temporal vectors for cell fate programming are described.

FIG. 1 shows a single vector 101 carrying one or more cassettes encoding genetic effectors can be introduced by any delivery means 102 into the starting cell type 103. In one embodiment, the vector 101 exists within the cell 103 as an episome 104, an episomal vector 101 apart from genomic DNA 106. The vector 101 may optionally include an origin of replication.

Figure 2:
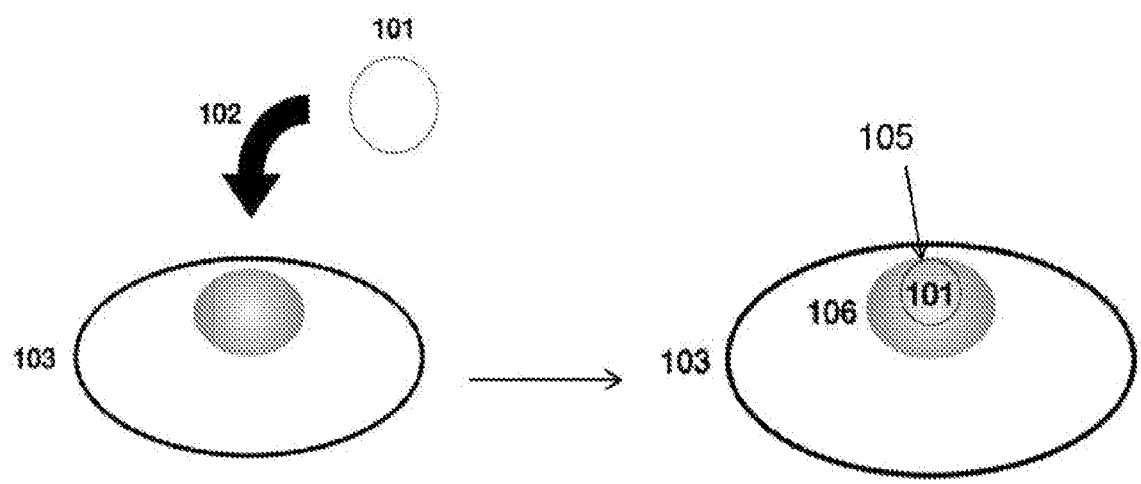
FIG. 2 depicts an integrated vector.

FIG. 2 depicts an integrated embodiment in which the vector 101 or corresponding cassette elements are integrated into genomic DNA 106 within the cell 103 as an integrated segment 105 of DNA in the genome of the cell 103. Integration methods include the use of viral vectors, transposable elements (e.g. PiggyBac), or targeted integration into a safe harbor locus, such as AAVS1 or CCR5, using genome editing techniques.

Figure 3:
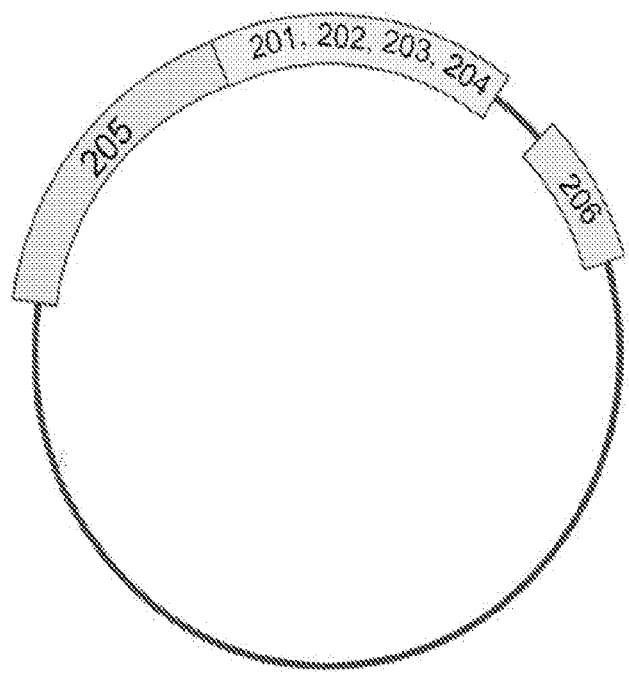
FIG. 3 shows separate cassettes.

FIG. 3 shows separate cassettes on the vector that can be composed of a variety of genetic effectors. These genetic effectors include CRISPR activator and inhibitor (CRISPRa/i) complexes 201, TALE transcriptional activator and inhibitor (TALEa/i) complexes 202, zinc finger activator and inhibitor (ZFa/i) complexes 203, and transcription factors 204. Any combination of those elements may be present and encoded on a vector 101 of the disclosure. Each of those effectors can be individually expressed from a single inducible promoter 205 except for CRISPRa/i, which preferably uses separate expression of the dCas9-activator/inhibitor under its promoter and a separate guide RNA (gRNA) cassette segment 206 that encodes one or more gRNA with dedicated promoter.

Any combination of CRISPR-dCas9, TALE, and zinc-fingers may be used in transcriptional activation and inhibition.

In addition to CRISPR-dCas9, transcription activator-like effectors (TALEs) and zinc-fingers comprise a powerful class of DNA-binding transcriptional regulators. They can be combined with various effector domains such as nucleases, transcriptional activators and repressors, recombinases, transposases, transcription factors (TFs) and DNA histone methyl and acetyltransferases, and be targeted to almost any DNA sequence. For example, TALEs can be used as transcriptional activators by using various TALE-TF's fused with the synthetic VP64 effector to fine tune the level of endogenous gene expression to mimic biological conditions. See Perez-Pinera, 2013, RNA-guided gene activation by CRISPR-Cas9-based transcription factors, Nature Meth 10(10):973-976, incorporated by reference. A catalytically inactive Cas endonuclease (e.g., dCas9) may be linked to a Kruppel associated box (KRAB), to provide an RNA-guided transcription repressor.

Similarly to dCas9-KRAB, TALEs can be fused with KRAB domain (or mSin Interaction Domain, or SRDX domain), to create a transcriptional repression complex targeting a promoter of a desired gene. See Mahfouz, 2012, Targeted transcriptional repression using a chimeric TALE-SRDX repressor protein, Plant Mol Biol 78(3):311-321, incorporated by reference.

Zinc fingers (ZNF) are DNA-binding domains with an ability to recognize and bind any DNA sequence of the human genome. Zinc fingers provide a versatile tool for various genome engineering applications. Individual ZNF domains recognize a 3 bp sequence of DNA, and a ZFN complex can be created with multiple ZNF-containing "modules" that together recognize and bind up to 18 bp of DNA. For gene knockout studies, a ZFN complex is fused with a Fok1-nuclease domain that—once dimerized with another ZNF-Fok1 domain designed for the complementary DNA strand—will cleave the DNA leading to disrupted expression. When the Fok1-domain is replaced by a transcriptional activator or repressor domain (VP64, KRAB, respectively), ZNF's can be used to control gene expression, in a way similar to Crispr-dCas9 and TALENs. See Gossen, 1992, Tight control of gene expression in mammalian cells by tetracycline-responsive promoters PNAS 89(12):5547-5551, incorporated by reference. Interestingly, ZNF's are intrinsically cell permeable, and can be used to deliver proteins into mammalian cells as effectively as with common transfection reagents.

Moreover, CRISPR-Cas9, TALEN, and ZNF technologies can also be used to target transposable elements, such as PiggyBac (PB) and Sleeping Beauty (SB), to specific locations like genomic safe harbors, as opposed to random integration into the genome that might lead to insertional mutagenesis and disruption of gene expression.

Any of those Cas, TALE, or ZNF regulators may be placed in a vector downstream of an RNA polymerase promoter such that, under various conditions as described below, an RNA polymerase such as RNA pol II will transcribe the Cas, TALE, or ZNF regulator, inducing the regulation effect exhibited by that regulator.

Systems and methods of the disclosure provide inducible RNA polymerase II promoters.

For gene engineering and overexpression, the most commonly used inducible systems rely on single DNA sequencerecognizing repressor proteins, such as the bacterial regulatory proteins TetR's or LacI. In the Tet-OFF system, the presence of doxycycline 301 inactivates the gene expression system. The Tet-Off system makes use of the tetracycline transactivator (tTA) protein, which is created by fusing one protein, TetR (tetracycline repressor), found in *Escherichia coli* bacteria, with the activation domain of another protein, VP16, found in the Herpes Simplex Virus. The resulting tTA protein is able to bind to DNA at specific TetO operator sequences. In most Tet-Off systems, several repeats of such TetO sequences are placed upstream of a minimal promoter such as the CMV promoter. The entirety of several TetO sequences with a minimal promoter is called a tetracycline response element (TRE) 302, because it responds to binding of the tetracycline transactivator protein tTA by increased expression of the gene or genes downstream of its promoter. In a Tet-Off system, expression of TRE-controlled genes can be repressed by tetracycline and its derivatives. They bind tTA and render it incapable of binding to TRE sequences, thereby preventing transactivation of TRE-controlled genes.

In contrast, the Tet-ON system uses tetracycline to activate the expression of its target gene. See Gossen, 1995, Transcriptional activation by tetracyclines in mammalian cells, Science 268(5218):1766-1769, incorporated by reference. The Tet-ON system uses a "referse Tet repressor" (rTetR), which relies on the presence of tetracycline to induce transcription. Another transactivator rtTA (reverse tetracycline-controlled transactivator) was created by fusing rTetR with VP16. The tetracycline on system is also known as the rtTA-dependent system. Doxycycline is a derivative of tetracycline with high affinity for tTA and rtTA.

Traditional TetR and LacI systems are powerful tools to regulate gene expression in animals and bacteria, respectively, but due to their requirement for specific DNA target sequences, their use in manipulating gene circuits and gene activation and inhibition cascades are limited. To overcome this, Copeland et al. (2016) designed a system for canonical gene repression and induction with customizable DNA-sequence specificity of TALEN (310)s in *E. coli*. Copeland, 2014, Application of TALEs, CRISPR/Cas and sRNAs as trans-acting regulators in prokaryotes, Curr Op Biotechnol 29:46-54, incorporated by reference.

Figure 4:
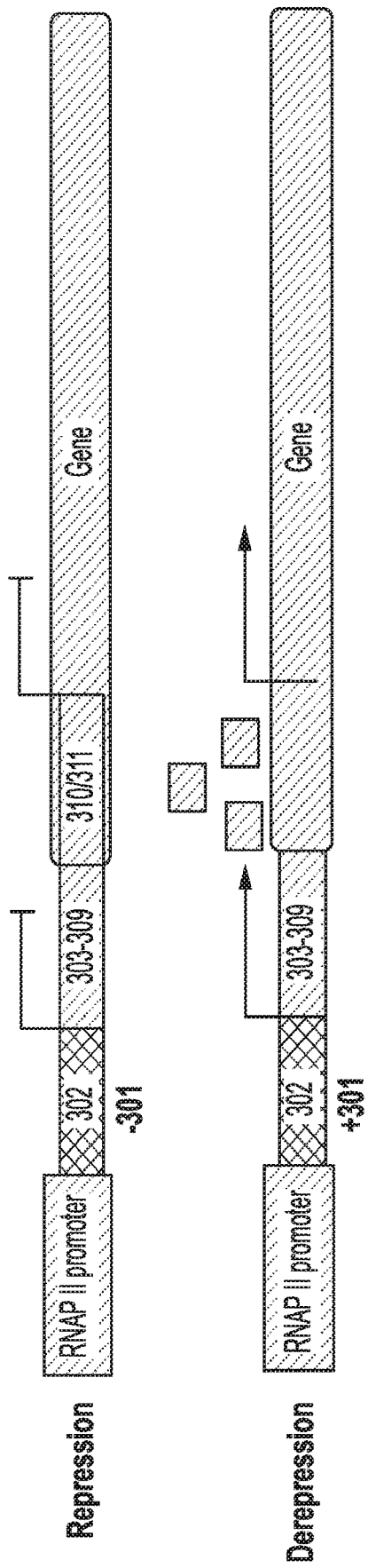
FIG. 4 shows a vector encoding TALE fused with a TEV-protease recognition domain.

FIG. 4 shows a vector that includes a segment 310 encoding a modified TALE fused with a TEV-protease recognition domain. The vector also includes a tobacco etch virus (TEV) protease sequence 303, a tetracycline response element (TRE) 302, and an RNA pol promoter (the vector works similarly if a segment 311 encoding ZNF designed to bind to specific DNA target is included). When the TALE is expressed, the TALE binds to its intended target in the genome of the cell and represses expression of a gene. The top row of shows that state, in which TALE is repressing expression of the Gene.

When doxycycline 301 is introduced, TEV protease sequence 303 is expressed as TEV protease. The TEV protease cleaves the TALE, thereby de-repressing expression. Thus, the bottom row shows that once a TetR-regulated Tobacco Etch Virus (TEV)-protease 303 expression is induced by adding doxycycline 301, the TALE is post-translationally degraded and its target gene expression resumes. Thus, using such a TetR system, doxycycline triggers expression of one or more genes, or—more specifically—triggers transcription of one or more segments of DNA.

In a Lac1 system, elements of a lac operon are included. The segments of DNA to be controlled are under control of the operator (LacO), the binding site for the repressor. The Lac1 gene is included and encodes a repressor protein that binds to the LacO, and blocks binding of polymerase, which prevents the segments of DNA from being transcribed. When lactose is introduced, the repressor gets un-bound from the LacO site, and the DNA segments are transcribed.

Additionally or alternatively, rapamycin 312 may be added to activate expression of a gene. In a rapamycin system, a promoter drive expression of two fusion transcription factors: one transcription factor consisting of three copies of the FKBP protein fused to a ZFHD1 DNA binding domain; a second transcription factor consisting of a FRAP protein with a p65 activation domain. Rapamycin enables dimerization of the transcription factors, with enable binding and activation, driving expression of the gene. Similarly, systems based on the ecdysone receptor (EcR) may be used that use ponasterone A (PonA) as an activator.

The ecdysone receptor (EcR) is a member of the retinoid-X-receptor (RXR) family of nuclear receptors and is composed of three domains: an N-terminal activation domain (AD), a central DNA-binding domain (DBD), and a C-terminal ligand-binding and dimerization domain (LBD). In insect cells, EcR and the nuclear receptor ultraspiracle (USP) form a promoterbound heterodimer, which regulates transcription. In the absence of ecdysone, the receptor heterodimer binds to corepressors and tightly represses transcription. When ecdysone binds to the EcR LBD, the corepressors are released, coactivators are recruited to the complex, and transcriptional activation is enabled. In mammalian cells harboring the EcR gene, EcR heterodimerizes with RXR, the mammalian homologue of USP. The EcR-RXR heterodimer binds to multiple copies of the ecdysone-responsive element (EcRE), and in the absence of Ponasterone A (ponA), represses transcription of an expression cassette. When rapamycin binds to the receptor, the receptor complex activates transcription of a reporter gene or a gene of interest.

Another expression control system that may be used is the RU486 system. The RU486 system relies on the drug RU486 to activate a chimeric transcription factor that drives transgene expression. A chimeric regulator protein is constitutively produced, consisting of the DNA-binding domain of the yeast transcription factor Gal4 (Gal4 DBD), a truncated progesterone ligand-binding domain (PRLBD), and a VP16 activation domain. In the presence of RU486, the regulator protein is activated, enabling binding to the target construct consisting of 17×4Gal4 DNA-binding sites and a minimal promoter (such as TATA) upstream of the transgene.

An expression vector may include separate genes (or segments of DNA to be transcribed), each under separate control of a separate inducible or repressible expression system. A first segment may be activated by exposure to tetracycline or doxycycline, while second, third, and fourth segments may separately be under control of induction by the introduction of lactose, rapamycin, rapamycin.

The segments that are under control can be transcription activators and/or inactivators that promote or repress transcription of other genes. The other genes that are expressed or replaced may be provided separately in the vector or another vector but in preferred embodiments, are in the nuclear genome of the cells that are being cultured and controlled in systems and methods of the disclosure.

Those genome sequences that are expressed and repressed may be those that direct the cell to differentiate to a specific cell type or ones that direct the cell to de-differentiate into a form of stem cells.

A number of pathways may be used to reprogram cells from one type to another type. For example, Oct4, Klf4, Sox2, c-Myc—to reprogram fibroblasts into induced pluripotent stem cells (iPSCs). Differential regulation of Oct-4 and SOX2 levels have been shown to precede germ layer fate selection. Increased levels of Oct4 and decreased levels of Sox2 promote a mesendodermal fate, with Oct4 actively suppressing genes associated with a neural ectodermal fate. Similarly, Increased levels of Sox2 and decreased levels of Oct4 promote differentiation towards a neural ectodermal fate, with Sox2 inhibiting differentiation towards a mesendodermal fate. Also, myoblast determination protein 1 (MyoD), is capable of transdifferentiating fibroblasts to myoblasts. In another example, Induced oligodendrocyte precursor cells (iOPCs) were generated from mouse and rat fibroblast using transcription factors Sox10, Olig2, Zfp536. Functional midbrain dopaminergic induced neuronal progenitors (iDPs) could be reprogrammed from mouse embryonic fibroblast or adult tail-tip fibroblast using 4 Yamanaka factors, Shh, and FGF8. The three gene combination of Ascl1, Brn2 and Mytl1. The genes were sufficient to reprogram mouse embryonic dermal and postnatal tail-tip fibroblast into induced neurons. Induced motor neurons (iMNs) have been made with Ascl, Brn2, Mytl1, Lhx3, Hb9, Isl1, and Ngn2. In another example, ectopic expression of Ascl1, Nurr1, Lmx1a could change mouse prenatal and adult tail-tip fibroblast to induced dopaminergic neurons. It has also been shown that three developmental cardiac transcription factors, Gata4, Mef2c, and Tbx5 may be used to make cardiomyocytes. One group induced cardiomyocytes (hiCMs) from human fetal heart and neonatal skin fibroblast by using Gata4, Mef2c, Tbx5, Essrg, and Mesp1. In another example, hiCMs have been made from human neonatal foreskin and adult cardiac, dermal fibroblast with Gata4, Hand2, Tbx5, myocardin, miR-1, and miR-133. In another example, the factors Hnf4a, Foxa1, Foxa2, or Foxa3 can reprogram mouse fibroblast into hepatocytes. Human induced hepatocytes (hiHeps) have been made from human fetal limb and adult dermal fibroblast with expression of Foxa3, Hnf1a, and Hnf4a. Also, the transcription factor Pdx1 has been used to direct liver cells toward insulin-producing cells. Using a polycistronic construct with Pdx1, Ngn3, and Mafa factors, changes toward a beta-cell lineage have been shown in the pancreatic exocrine cell line AR42j-B13. Generally, see Kim, 2016, Direct reprogramming and biomaterials for controlling cell fate, Biomater Res 20:39 and Cavelti-Weder, 2015, Direct reprogramming for pancreatic beta-cells using key developmental genes, Curr Pathobiol Rep 3(1):57-65, both incorporated by reference. These references and examples show that cells of a specific type may be made by expression or introduction of appropriate sets of transcription factors.

The temporal vectors can respond to tetracycline, doxycycline, lactose, rapamycin, rapamycin, or RU486 to express CRISPRa/i systems (or activation/inactivation systems based on TALE or ZNF) to trigger expression or repression of genomic transcription factors. By deliver the tetracycline, doxycycline, lactose, rapamycin, rapamycin, or RU486 at different time point, a temporal sequence may be established. In one example, a vector is delivered to fibroblasts. The vector response to doxycycline to express CRISPRa to upregulate Oct4, Klf4, Sox2, c-Myc, de-differentiating the cells into stem cells. Later, lactose, for example, is delivered causing the vector to express CRISPRa to upregulate Pdx1, Ngn3, and Mafa to differentiate the stem cells into beta cells. That is but one illustrative example; those of skill in the art will appreciate that the temporal vectors can encode any arbitrary number of different transformation pathways that proceed along different biological steps over time.

Figure 5:
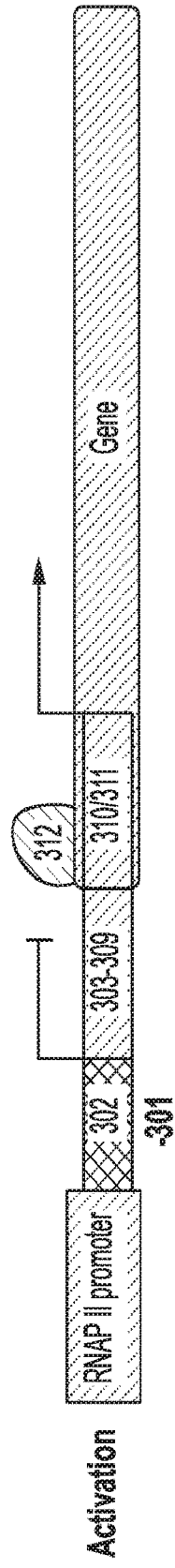
FIG. 5 shows an embodiment with a Tet-ON system.

FIG. 5 shows an embodiment in which a Tet-ON system and a set of specific proteases 303-309 combined with TALEN-VPR 312 are used to temporally transiently activate expression of a gene.

Figure 6:
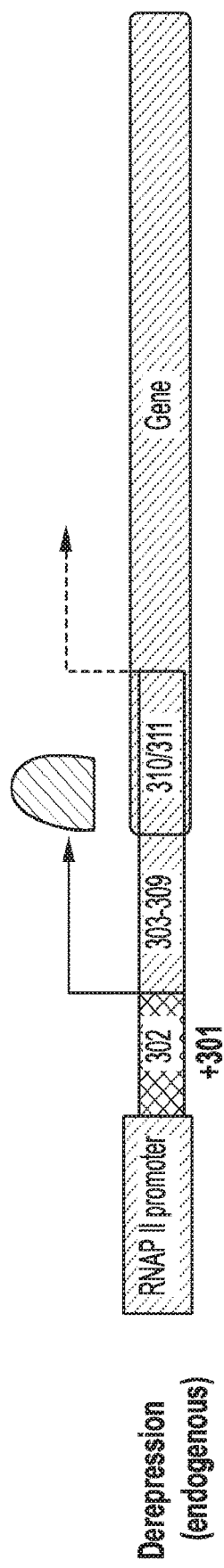
FIG. 6 shows de-repression embodiment.

FIG. 6 shows an embodiment in which a Tet-ON system and a set of specific proteases 303-309 combined with TALEN-VPR 312 are used to temporally transiently derepress.

Figure 7:
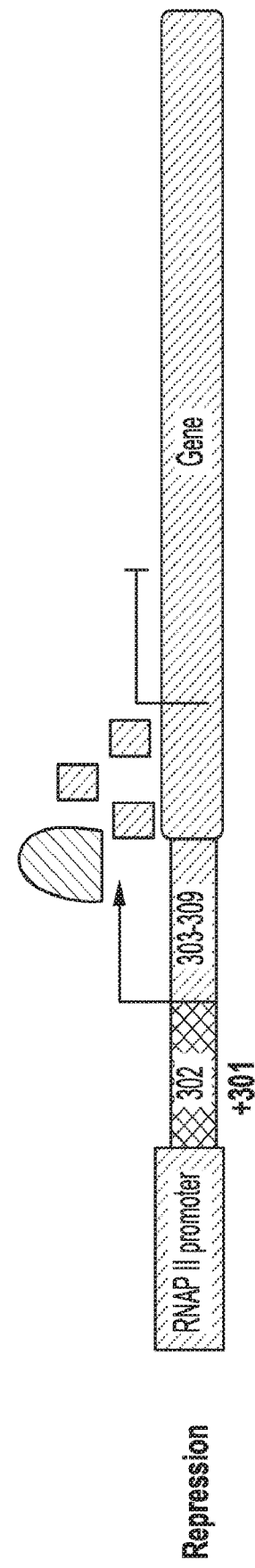
FIG. 7 shows a repression embodiment with a Tet-ON system.

FIG. 7 shows an embodiment in which a Tet-ON system and a set of specific proteases 303-309 combined with TALEN-VPR 312 are used to temporally transiently repress.

Figure 8:
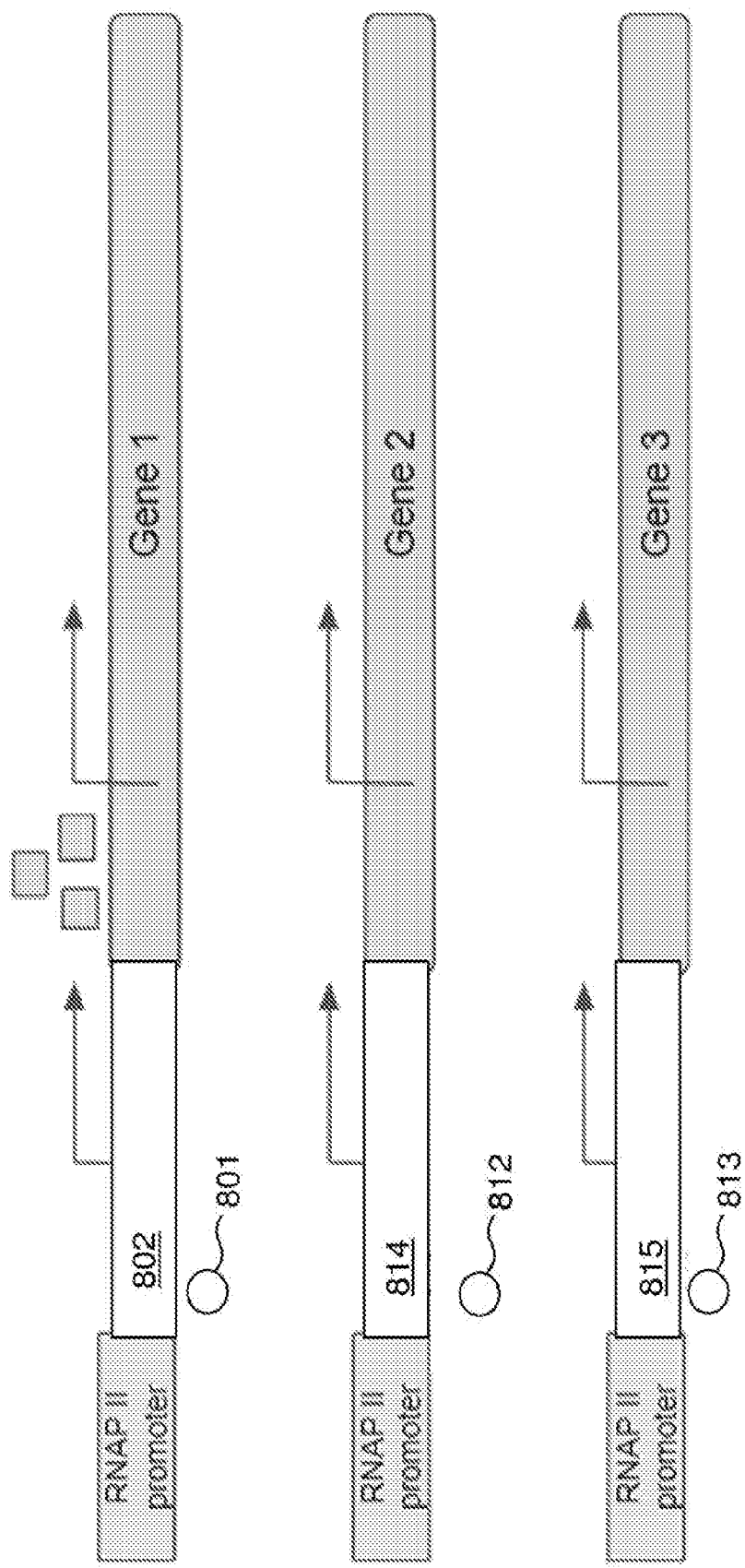
FIG. 8 shows multiplexed use of the temporal vectors.

FIG. 8 shows multiplexed use of the temporal vectors. The vectors include components that provide for temporal control. To temporally control multiple activation cascades in an inducible manner, the doxycyclin-responsive TetR system 802 is used in cone component of the vector. Other components include a rapamycin response system 814 and an ecdysone response system 815. The addition of doxyciclin 801 induces expression of Gene 1 (which may be a set of genes or transcription activator/inactivator specific for one or more nuclear genes). The addition of rapamycin 812 triggers expression of Gene 2. The introduction of PonA leads to expression of Gene 3.

For an additional layer of controllability TEV-proteases can be genetically engineered to recognize and cleave various target sequences. See Yi, 2013, Engineering of TEV protease variants by yeast ER sequestration screening (YESS) of combinatorial libraries, PNAS 110(18):7229-7234, incorporated by reference.

By using a Tet-ON system and a set of specific proteases and combined with TALEN-VPR, the segments shown may be included in a vector that may be used to temporally transiently repress and activate gene transcription in a multiplexed manner driven by a single plasmid in a mammalian system.

Similar to the TALEN-approach, zinc Finger Domains 311 designed to bind specific DNA sequence can be used to replace TALEN. A short fluorescent tag sequence under a constitutively active promoter can also be added before the RNAP II promoter in order to detect the delivery of the vector into the cells with OCP.

Figure 9:
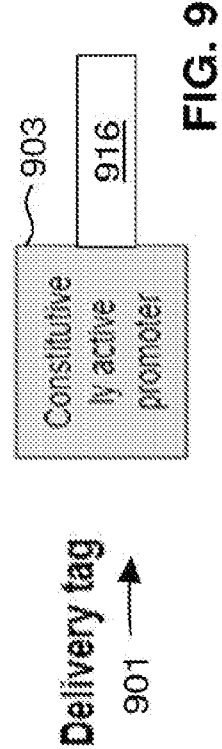
FIG. 9 shows a delivery tag.

FIG. 9 shows a delivery tag 901 that includes a short fluorescent tag sequence 916 under a constitutively active promoter 903. Lack of fluorescence in the cells indicates that the vectors has not been delivered into the cell, allowing for easy detection removal by the OCP Preferred embodiments include inducible gRNA expression from RNAP II promoters.

Vector backbones not only have size limits but can be difficult to clone or assemble as their sizes increase.

The disclosure provides various embodiments of a stepwise cell state induction system using a single vector leveraging the CRISPRa/i system. Such embodiments may be used to bypass the cargo capacity issue of vectors. The depicted embodiments generally comprise a cassette expressing the dCas9-activator 413 from a constitutive or drug inducible 404-406 promoter with additional cassettes expressing one or more gRNAs 409-412 under separate inducible promoters. A short fluorescent tag sequence may be added into the vector after constitutively active promoter in order to detect the delivery of the vector into the cells with OCP. Lack of fluorescence in the cells indicates that the vectors has not been delivered into the cell, allowing for easy detection removal by the OCP.

Post-transcriptional modifications of RNA molecules are regulated by the RNA-polymerase driving transcription. Most of the reports to date describe the use of U6 and H1 promoters to drive the RNA Polymerase III (RNAP III)-mediated transcription of gRNAs. However, there are limited number of RNAP III's and they are mostly constitutively active, making conditional, temporal, and tissue-specific regulation of gRNA expression challenging with CRISPR-Cas9 systems. See Orioli, 2012, RNA polymerase III transcription control elements: Themes and variations, Gene, incorporated by reference.

Unfortunately, the well-characterized and commercially available RNAP II promoters cannot be directly used to drive gRNA expression due to heavy post-transcriptional processing rendering them non-functional and to their export from the nucleus to the cytosol. To deliver gRNAs (409) together with dCas9 construct, a bi-promoter plasmid may be used.

Using RNA Pol II to transcribe gRNAs, when successful, has various benefits such as coupled gRNA and protein transcription from the same vector.

Figure 10:
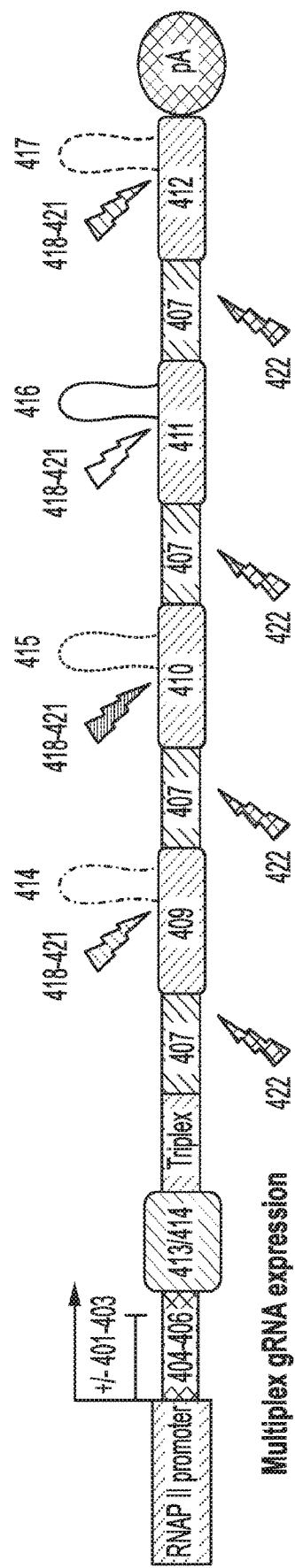
FIG. 10 shows 3'RNA triple helices ("triplex"), introns, and ribozymes.

FIG. 10 shows embodiments in which 3'RNA triple helices ("triplex"), introns, and ribozymes 407 are used together with CRISPR-Cas9 system to create up to four multiplexed, temporally controlled gRNAs by CMV-driven RNA Pol II in a single transcript. The vector includes inducible spacer blocking hairpins 414, 415, 416, 417 useful to rapidly inhibit gRNA function). See Ferry, 2017, Rational design of inducible CRISPR guide RNAs for de novo assembly of transcriptional programs, Nature Comm 8:14633, incorporated by reference. These inhibitory hairpin loops can be cleaved off by specific RNA endonucleases (418-421) or DNA oligonucleotides providing means to highly specific parallel activation of multiple genes.

In order to enable multiplexed temporal induction of these constructs, 1-5 of the aforementioned cassettes can be placed on a single vector.

Using RNAP II also allowed simultaneous expression of gRNAs 409-412 and proteins 413, 414 from the same RNA-transcript, adding an extra regulatory element to further enhance gene control. One method for expressing gRNA-mRNA from the same construct requires an RNAP II promoter—such as CMV or EF1a—to drive gRNA sequence(s) flanked by recognition sites (407) for endonuclease Csy4 (422). When Csy4 is endogenously expressed, Csy4 cleaves its recognitions sites, a functional gRNA molecule (409, 410, 411, 412) is released, and the poly-A-tail (pA) from the following mRNA is removed. Since the loss of poly-A-tail renders transcripts liable to degradation, an additional mRNA stabilizing triple-helix structure can be added onto the construct to ensure translation of the protein (413/414) mRNA. See Nissim, 2014, Multiplexed and Programmable Regulation of Gene Networks with an Integrated RNA and CRISPR/Cas Toolkit in Human Cells, Molecular Cell 54(4):698-710, incorporated by reference.

To make this system tissue or cell type specific, Csy4 expression can be linked to endogenous cell-type specific promoters.

Another method for creating functional gRNA's from RNAP II promoters is to employ self-cleaving ribozymes, such as hammerhead (HH) sequence 408 and Hepatitis delta virus HDV 422 ribozymes on the 5' and 3' end of the gRNAs 409, 410, respectively. See Ferré-D'Amaré, 1998, Crystal structure of a hepatitis delta virus ribozyme, Nature 395 (6702):567-574, incorporated by reference.

Figure 11:
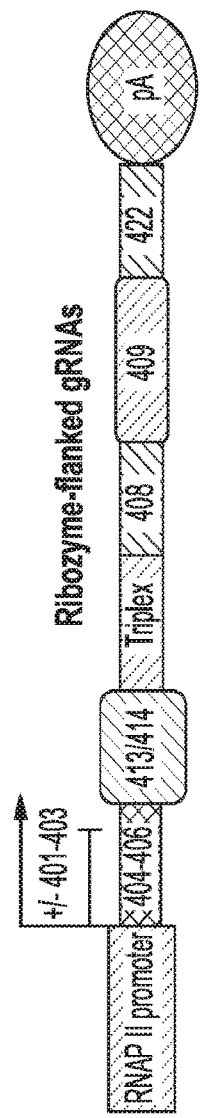
FIG. 11 shows gRNA sequences flanked by ribozyme sequences.

FIG. 11 shows gRNA sequences 409 flanked by ribozyme sequences 407, 422.

Although this offers an additional, potentially tissue-specific gRNA cleavage mechanism, it does not provide temporal control since ribozymes are constitutively active once translated.

By combining the Csy4 422 and triplex approaches, RNAP II can be used to transcribe gRNAs (409-412) in order to create a cascade of transcriptional activation. In addition to creating gRNAs, the aforementioned methods can be used also for controlled transcription of shRNAs and miRNA's, creating an even more complete matrix of tools for gene control (Nissim 2014). These genomic tools can also be combined with inducible, cell type specific RNAP II promoters 404-406 that can activate (e.g. dCas9-VPR, 413+423), inhibit (e.g. dCas9-KRAB, 413+424), or mutate (Cas9) target genes via multiplexed expression of gRNAs, shRNAs (409-412), and miRNAs (409-412) in a temporal and tissue-specific manner. For example, in Liu et al. (2014), cell-type specific promoters were used together with CRISPR-Cas9 technology to demonstrate that the combination of a cancer cell-specific promoter driving Cas9 and bladder-cell specific gRNAs can be used to specifically induce apoptosis in bladder cancer cells (Liu et al., 2014).

Figure 12:
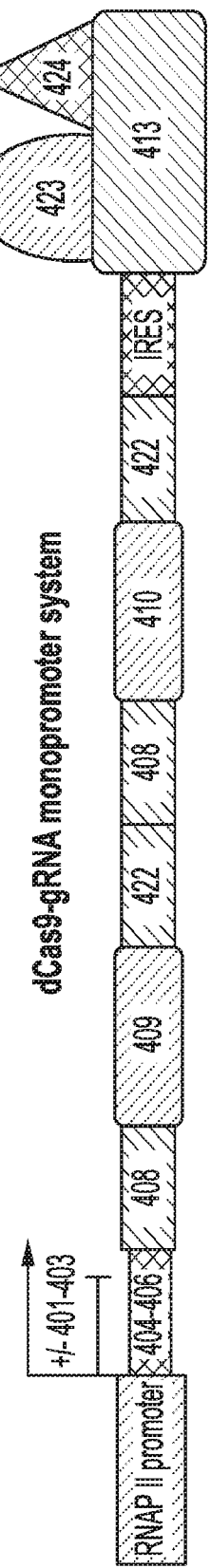
FIG. 12 shows a "mono-promoter" approach.

FIG. 12 shows a "mono-promoter" approach in which Cas9 mRNA and ribozyme-site flanked gRNAs are encoded from the same plasmid.

It has been shown that such a "mono-promoter" approach is possible where Cas9 mRNA and ribozyme-site flanked gRNAs are encoded from the same plasmid, reducing the delivery load to the cell. See Yoshioka, 2015, Development of a mono-promoter-driven CRISPR/Cas9 system in mammalian cells, Scientific Reports 5:18341 and Zhang, 2017, CRISPR/Cas9 Genome-Editing System in Human Stem Cells: Current Status and Future Prospects, Molecular Therapy—Nucleic Acids, both incorporated by reference.

A similar approach can be used to deliver any gRNA-mRNA vector to the cell, the main limiting factor being the size of cargo.

Figure 13:
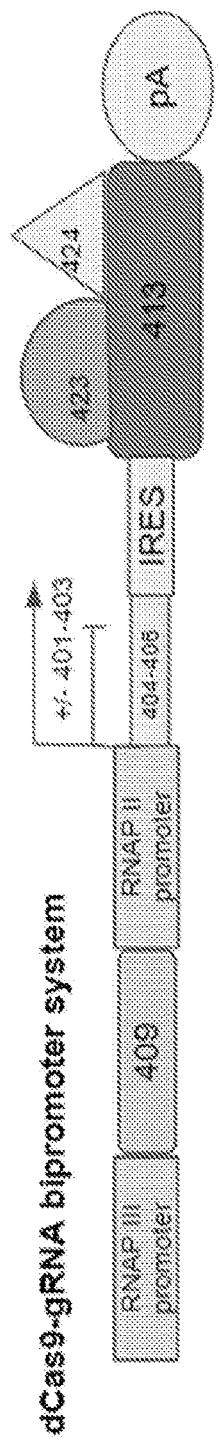
FIG. 13 shows a dCas9-gRNA bipromoter system.

FIG. 13 shows a dCas9-gRNA bipromoter system in which Cas9 mRNA 413 can be expressed inducibly and in a tissue-specific manner to either activate 413+423 or repress 413+424 the target gene expression.

The disclosure provides embodiments in which Cassette 1 on the vector directly links the expression of the dCas9 complex with its associated gRNAs.

Figure 14:
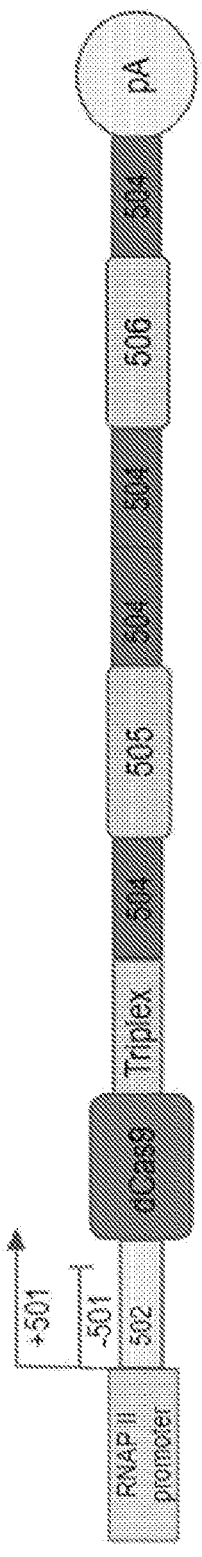
FIG. 14 shows an example in which a small molecule induces expression.

FIG. 14 shows an example in which the presence of a small molecule (501) induces expression of a single transcript from an RNAP II promoter (502). This transcript contains the dCas9 complex linked via triplex to two gRNAs (505-506) separated by ribozymes (504) and terminated by pA. Upon successful transcription by the cell, the RNA transcript will self-cleave to yield the mRNA encoding the dCas9 complex and two physically separated, ready-to-function gRNAs (505, 506). A fluorescent tag may be added into the vector after constitutively active promoter to indicate the successful delivery of the vector into the cells. This allows the image-based laser tool to remove cells that do not have the cargo.

Figure 15:
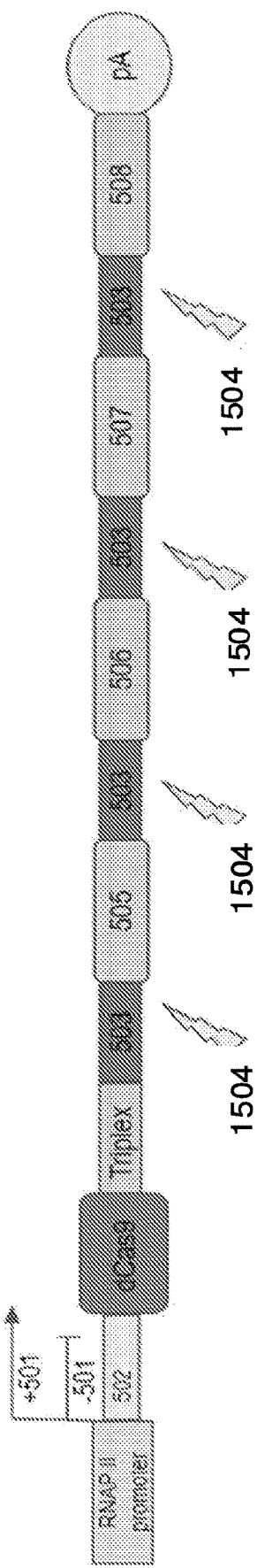
FIG. 15 shows another example of induction.

FIG. 15 shows another example in which the presence of a small molecule (501) induces expression of a single transcript from an RNAP II promoter (502). This transcript contains the dCas9 complex linked via triplex to four gRNAs (505-508) separated by Csy4 recognition sites (503) and terminated by pA. When this cassette is successfully transcribed in a cell that expresses the Csy4 protein (1504), its recognition sites (503) are cleaved, yielding the mRNA encoding the dCas9 complex and four physically separated, ready-to-function gRNAs (505, 506, 507, 508). A fluorescent tag may be added into the vector after constitutively active promoter to indicate the successful delivery of the vector into the cells. This allows the image-based laser tool to remove cells that do not have the cargo.

In this embodiment, Cassettes 2-5 on the vector contain additional separately inducible gRNA(s) (described below) but not the dCas9 complex. These additional cassettes are expressed in different temporal sequences with distinct inducers after induction of Cassette 1.

In another embodiment, Cassette 1 contains only the inducible dCas9 complex alone. Cassettes 2-5 on the same vector contain separately inducible gRNA(s) (described below) but not the dCas9 complex. This allows the expression of Cassettes 2-5 (gRNAs) in any temporal sequence under distinct inducers, provided Cassette 1 (dCas9 complex) is simultaneously induced for the expressed gRNAs to be functionalized.

Embodiments provide for inducible gRNA expression from RNA polymerase III promoters.

In order to facilitate direct induction of gRNAs from RNAP III promoters, hairpin loops with cognate aptamers can be used to regulate a promoter sequence.

Figure 16:
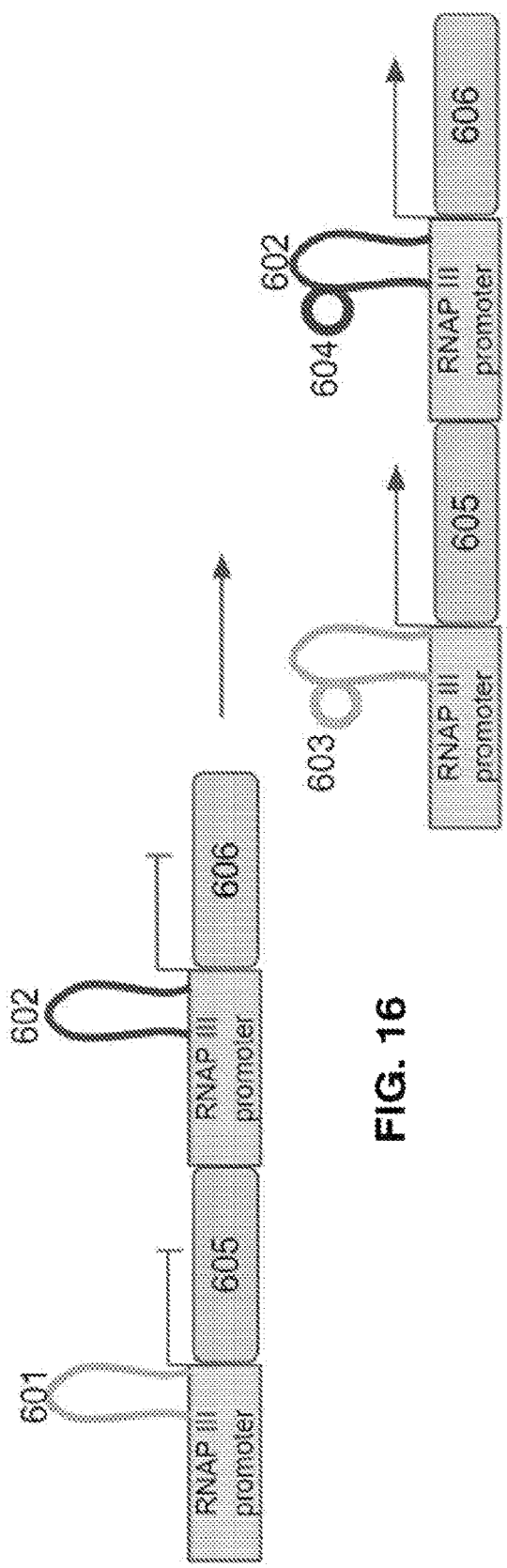
FIG. 16 shows a hairpin loop embodiment.

FIG. 16 shows an embodiment in which a hairpin loop (601-602) is inserted into the promoter that prevents binding of RNAP III and resulting gRNA (605-606) transcription. To induce this promoter system, cognate cell-permeable aptamers or small molecules (603-604) that bind to and stabilize the hairpin loop are delivered, allowing RNAP III binding and transcription of gRNA (605) to proceed.

Figure 17:
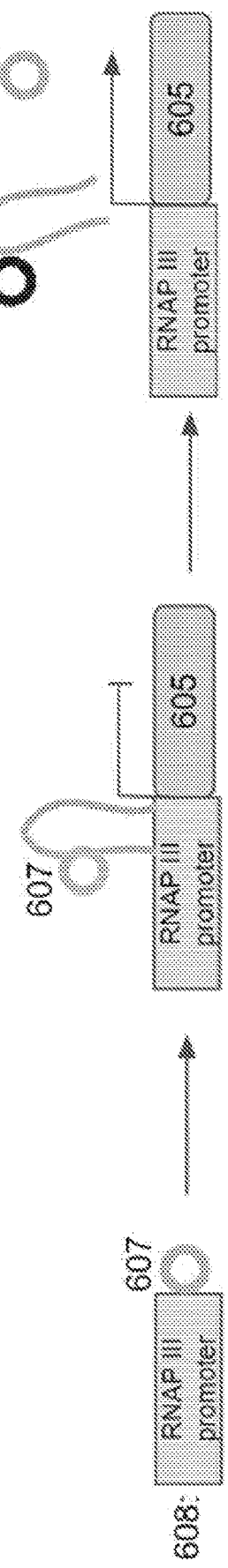
FIG. 17 shows an aptamer embodiment.

FIG. 17 shows an embodiment in which a separate cassette (608) on the vector constitutively expresses an aptamer (607) that binds to the promoter for a gRNA (605) to induce hairpin loop formation, preventing RNAP III binding and transcription. To induce this promoter system, a small molecule (609) that has a higher binding affinity for the aptamer (607) is introduced, complexing and displacing the aptamer from the promoter, thereby resolving the hairpin loop, allowing RNAP III to bind and transcription of gRNA (605) to proceed. In this way, a different promoter-aptamer-small molecule combination is utilized for each separately inducible gRNA or set of gRNAs linked via abovementioned modalities.

Examples of the Use of Vectors and OCP for Cell Fate Programming: hiPC's and Cardiomyocytes HiPSC derivation: Human induced pluripotent stem cells (hiPSC's) harbor an unlimited tissue generation potential. These cells are commonly derived from somatic cells acquired from muscle biopsies, blood cells or cells in the urine. Originally, hiPSCs were generated by exogenous expression of transcription factors OCT4, SOX2, KLF4 and c-MYC from retroviral vectors, thus resulting in genome integration. To circumvent the risks of genome integration, several nonintegrating methods are now being used to induce pluripotency in mammalian cells, including non-integrating episomal vectors, delivery of RNA and proteins, and use of small molecule compounds. See Chang, 2009, Polycistronic lentiviral vector for "hit and run" reprogramming of adult skin fibroblasts to induced pluripotent stem cells, Stem Cells 27(5):1042-1049; Sommer, 2009, Induced Pluripotent Stem Cell Generation Using a Single Lentiviral Stem Cell Cassette, Stem Cells 27(3):543-549; Soldner, 2009, Parkinson's disease patient-derived induced pluripotent stem cells free of viral reprogramming factors, Cell 136(5):964-977; and Somers, 2010, Generation of transgene-free lung disease-specific human induced pluripotent stem cells using a single excisable lentiviral stem cell cassette, Stem Cells 28(10):1728-1740, all incorporated by reference.

Despite the number of methods available for hiPSC-derivation, their efficiency to convert somatic cells to hiPSC's is very low, varying between 0.0003-0.1% depending on the approach. See Malik, 2013, A review of the methods for human iPSC derivation, Meth Mol biol 997:23-33, incorporated by reference.

These methods also rely on assessment of cell morphology by technicians and manual picking of the desired hiPSC-like colonies, both prone to lead to human error and lack of reproducibility. The use of fluorescently tagged reprogramming vectors together with the image-based laser described in this innovation allows us to remove cells that did not receive the vector based on the lack of fluorescence within the first 72 h of vector delivery. During the next 20-35 days, which is when the cells are being reprogrammed, we can use live-cell staining of cell surface antigens for pluripotency factors to further remove cells that despite the successful delivery of the vector are not undergoing successful reprogramming. Our laser-based cell removal allows for purification of the culture without the use of harsh dissociation enzymes and cell sorting, and due to the laser's subcellular resolution, we can detect and select cells in a denser culture than the current protocols allow, resulting in increased viability and efficiency of the overall reprogramming. In addition, we can use the image-based laser cell removal to create clonal hiPSC-lines without having to rely on the limiting dilution steps that render sensitive hiPSC's prone to secondary mutations to favor for single-cell survival by monitoring the proliferation of various clones in the same well and once the single-cell-derived colonies reach a size sufficient to support survival, by removing the rest of the colonies.

Cardiac Myocyte Differentiation

Despite major advances in cardiovascular medicine, heart disease remains a leading cause of death worldwide. The adult mammalian heart has only a limited capacity for regeneration and, consequently, the cardiomyocytes (CMs) that are lost to ischemic injury are typically replaced by fibrotic scar tissue. To date, the only viable option for patients with the end-stage heart disease is whole heart transplantation. However, the shortage of donor hearts makes this approach unavailable for most of patients. The development of new and effective techniques for regenerating injured myocardium, or for correcting the fundamental molecular defects that lead to disease onset and progression, would thus have important therapeutic implications.

Combined approach with temporally activatable transcription factor vectors and image-guided laser based delivery and removal can be very beneficial for the majority of current differentiation protocols, where induced transcription factor activation has been shown to increase differentiation and where the end product with current methods is not of 100% purity. In cardiac differentiation it has been shown that increasing the number of cardiac myocytes from 20% to 50%, the expression of 5 TF's on day 8 of the differentiation protocol is needed. See Jin, 2018, Enhanced differentiation of human pluripotent stem cells into cardiomyocytes by bacteria-mediated transcription factors delivery, PLoS ONE 13(3):e0194895, incorporated by reference.

This can be achieved with various methods, including using vectors (e.g., as shown) (with simultaneous expression of CRISP-Cas9-VPR from a previously delivered vector or RNP). However, even with this forced differentiation, only 50% of the cells become beating cardiomyocytes. See Oh, 2019, Directed differentiation of pluripotent stem cells by transcription factors. Molecules and Cells 2439, incorporated by reference.

The other 50% of the culture consists of contaminant cell types, that need to be removed prior to transplantation into animals or human patients. With current methods, this is done by dissociating cultures into single cells for cell sorting, leading to complete loss of cell-cell contact crucial for the electrical coherence and function of the tissue. As a consequence, these cells have a very low rate of cell engraftment upon transplantation. Engineered heart tissues (EHTs), designed to morphologically and functionally resemble native myocardium, could provide unique advantages for enhancing cell engraftment compared with the direct myocardial injection of cell suspension. In fact, animal studies indicate that the engraftment rate can be substantially higher when the cells are administered as an EHT compared with the cell injection or infusion. By using OCP, myocardial cultures can be purified while in an attached monolayer from contaminant cell types based on the specific morphological features of the cell type, or based on a transient fluorescent labeling of the culture by cell-type specific reporter vector. By avoiding single-cell dissociation, the contractability of the myocardial culture is preserved, allowing for a transplantation or analysis of the tissue in its functional state, and free of contaminant cell types.

The disclosure includes description of the fluorescent-tagged vectors for cell culture patterning.

Co-culturing differentiating hiPSCs with other cell types has been shown to be beneficial for several cell types, such as astrocytes and dopaminergic neurons, cardiac myocytes and endothelial cells, and photoreceptors and retinal pigment epithelial cells. In these cases, OCP can be used to deliberately create and maintain optimal coculture environment for the target cell differentiation. For example, differentiating dopaminergic cells from hiPSCs has been shown to benefit from coculturing them in a 10% astrocyte coculture. At the end of the differentiation protocol, these supporting "helper" cells, astrocytes in the case of dopaminergic neuronal cultures, can be removed by the OCP, leaving a pure culture of target cell type on the dish. The OCP can distinguish these helper and target cell based on their different morphological features, or a cell-type specific fluorescent reporter can be added into the cells. In the case of adding the reporter to the helper cells, it can be either constitutively active reporter integrated into the genome or transiently expressed episomal cell-type-specific reporter. Also the target cells can be fluorescently tagged in similar fashion. However, it is best to avoid integrating tags in the target cells especially if the cells are aimed for clinics where any additional DNA-integration event can cause biological and FDA regulatory issues.

In the case of a coculture system where the end product consists of various cell types, the OCP can be used to pattern these cells to create the optimal environment e.g., to mimic the biological tissue. In the case of neuronal retina, rod and cone photoreceptors form a monolayer of cells in the back of the eye. In vivo, these cells exist in a specific pattern and ratio to each other, which has been impossible to recapitulate in vitro. With OCP, by delivering differing gene modulators into neighboring cells and controlling the cell density and identity by removing incorrectly differentiating or misplaced cells, creation of such patterned monolayer of cells is possible, providing for studies and transplantation into patients with damaged photoreceptors.

An OCP may be combined with cascade vectors and used to differentiate a patterned rod and cone coculture that mimics the in vivo tissue.

Figure 18:
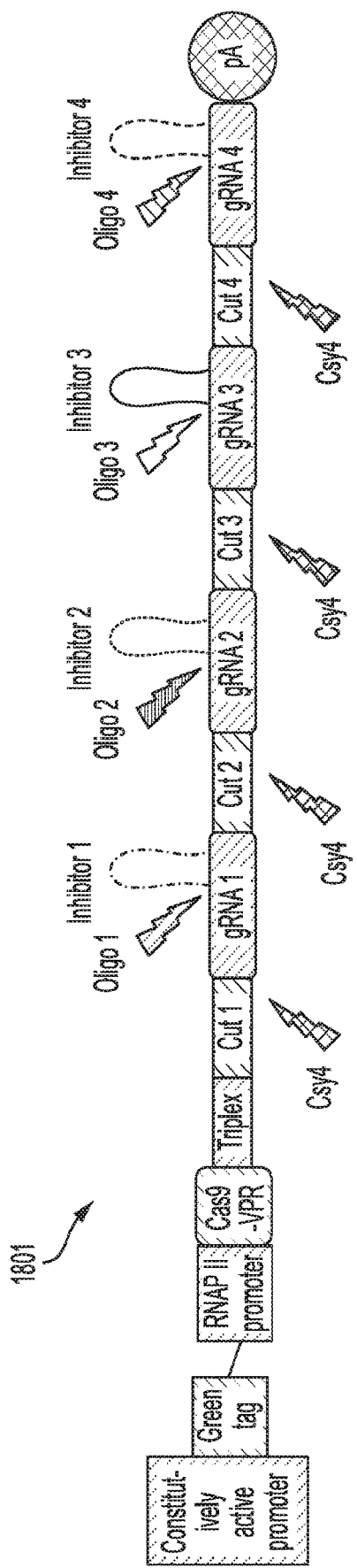
FIG. 18 shows a vector for rod differentiation.

FIG. 18 shows a vector 1801 for rod differentiation.

Figure 19:
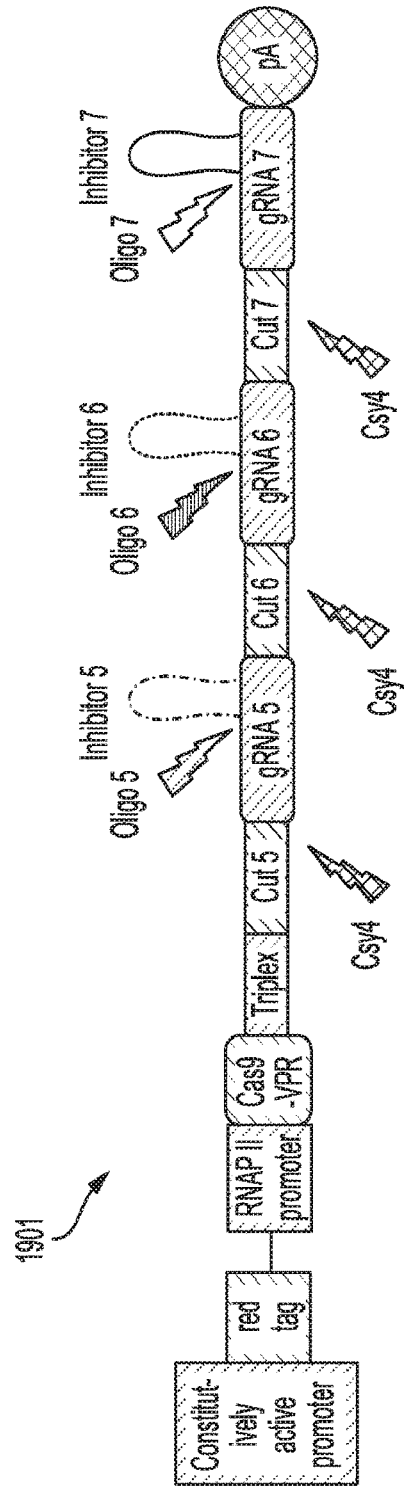
FIG. 19 shows a vector for cone differentiation.

FIG. 19 shows a vector 1901 for cone differentiation. The vectors 1801, 1901 contain gRNA's to activate and guide rod and cone differentiation, respectively. By adding a constitutively active promoter driven green tag and red tag to each vector the OCP can differentiate the cells that were delivered each vector.

Figure 20:
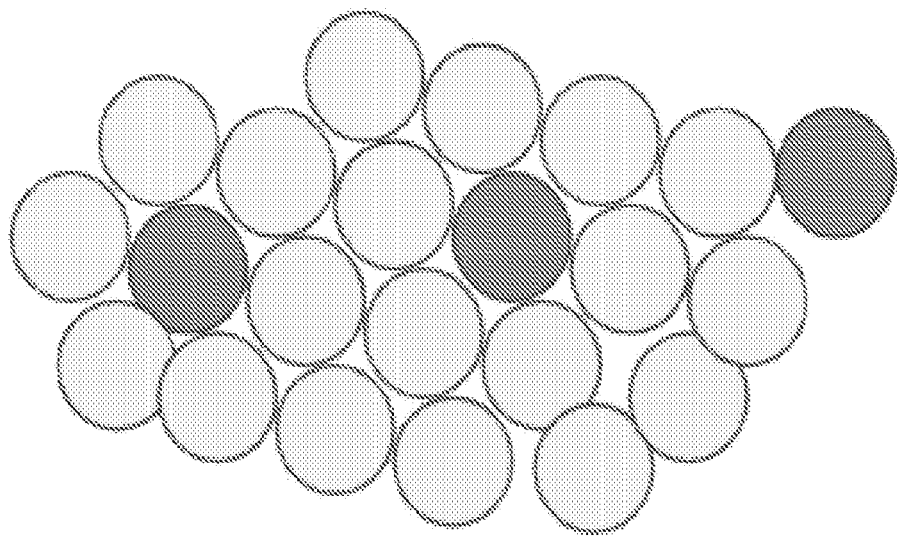
FIG. 20 shows delivery of vectors.

FIG. 20 shows delivery of vectors 1801 to rod precursors (dark circles) and vector 1901 to cone precursors (light circles) by the optical cell processor (OCP). The OCP is operated to perform fluorescent imaging driven laser removal of cells to obtain a desired ratio. After delivery of the vectors, the OCP will remove undesired cells to create the optimal 90-10% rod-done ratio of the culture.

Figure 21:
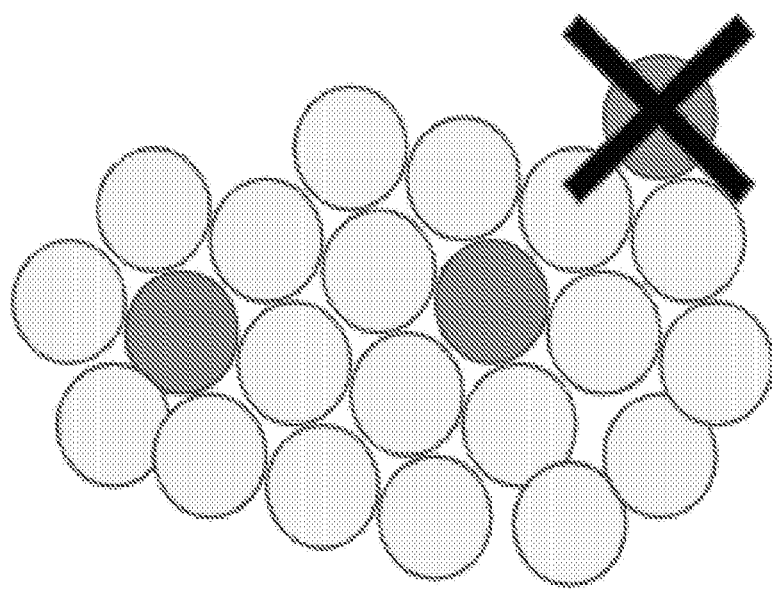
FIG. 21 illustrates operation of the OCP to remove an individual cell.

FIG. 21 illustrates operation of the OCP to remove an individual cell.

When the desired pattern is created, addition of Csy4 enzyme in the cell culture medium will result in cleavage of the cut-sites in the vector transcripts, releasing each gRNA+ inhibitor complex.

Figure 22:
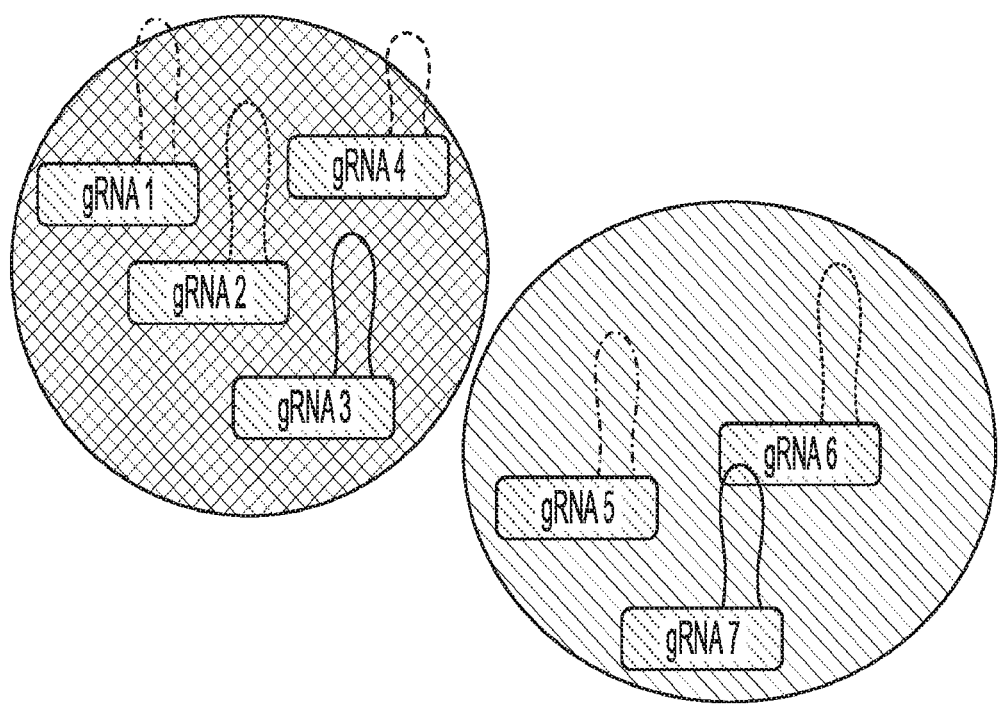
FIG. 22 shows cleavage and release of the inhibitors.

FIG. 22 shows cleavage and release of the inhibitors. Addition of the Csy4 protein cleaves each gRNA/inhibitor complex.

Figure 23:
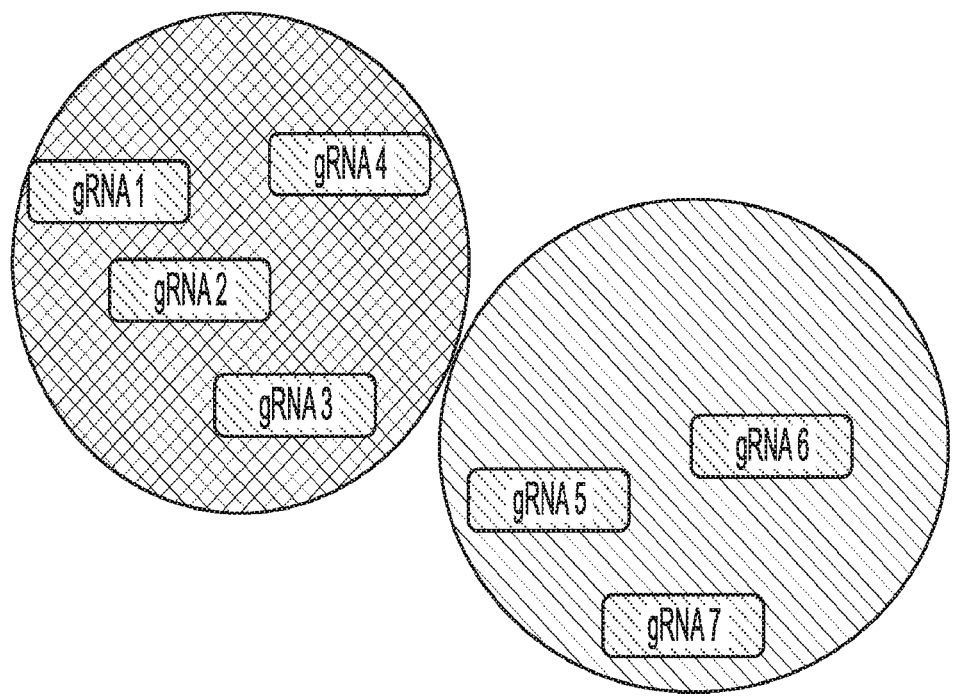
FIG. 23 shows delivery of inhibitor-specific DNA oligos.

FIG. 23 shows delivery of inhibitor-specific DNA oligos. Delivering inhibitor-specific oligos into the cells by OCP turns on transcription of the gRNA target genes in temporal manner for differentiation.

Activation of each gRNA target transcription factor occurs by delivering an inhibitor-specific DNA oligo into the cells by OCP. The timing of each activation step depends on the individual differentiation timeline of each cell type. Differentiation and maturation of each cell type is monitored with the OCP and any contaminant cell derivatives can be removed based on their differing features from the desired cell type.

In some embodiments, delivery of genetic effectors in vector format is accomplished using laser-based cell poration. Preferably, adherent cells are cultured on a biocompatible surface.

Figure 24:
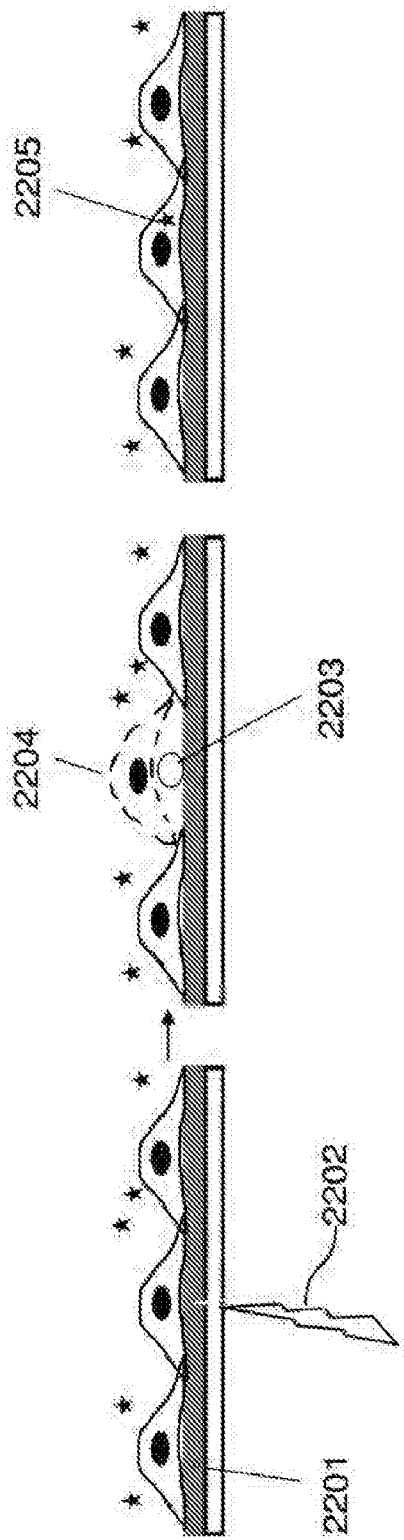
FIG. 24 shows a laser beam focused on an absorptive material.

FIG. 24 shows a laser beam 2202 focused on an absorptive material 2201 in close contact with a cell membrane. In the case of focusing on the absorptive material, the absorptive material 2201 efficiently absorbs the laser light 2202 energy, mediating a series of energy transfers that results in a rapid increase in temperature in the surrounding liquid. This rapid temperature increase results in the formation of a bubble 2203, followed by the formation of a pressure wave. This pressure wave generates sufficient shear stress to temporarily porate the cell membrane 2204, enabling the membrane-impermeable vectors 2205 to diffuse into the cell.

Figure 25:
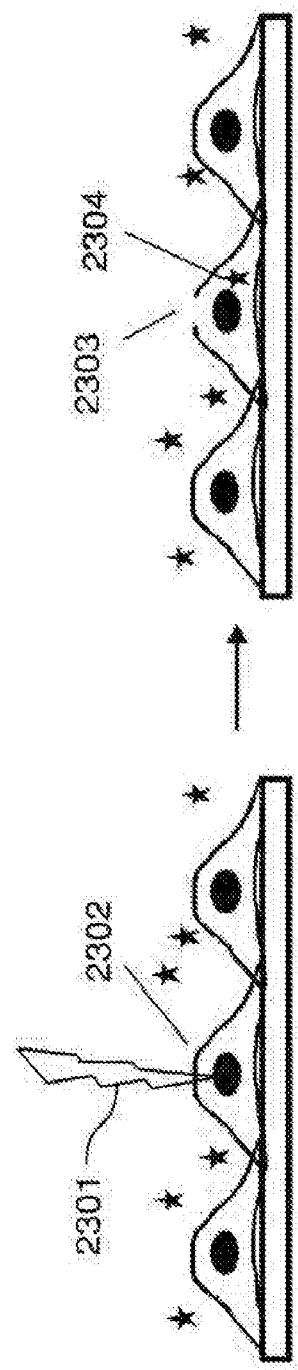
FIG. 25 shows a laser beam focused onto the cell membrane.

FIG. 25 shows a laser beam focused onto the cell membrane itself. Here, a laser beam 2301 is tightly focused onto the cell membrane 2302, resulting in the formation of a temporary pore 2303 through which the vector 2304 can diffuse into the cell. In this absorber-less case, the cell poration may be mediated by direct breaking of chemical bonds, the formation of a plasma-mediated bubble, thermal effects, or a combination thereof.

In some embodiments, the laser system enabling this intracellular delivery technique is used in conjunction with imaging and image analysis subsystems. The imaging and image analysis subsystems serve to image and classify the cells. This information can then be used to determine which cells are to receive various cargoes. The imaging and image analysis subsystems may also be used to verify which cells have been successfully delivered to, for example by imaging the expression of fluorescent reporters that are encoded within the vectors. Cells that are expressing an undesired phenotype (for example, cells that have not been successfully delivered to), can also be removed by the same mechanism used to porate the cells for delivery. For instance, cell poration may be achieved at a given laser fluence, whereas cell removal/killing may be achieved at a slightly higher laser fluence.

Figure 26:
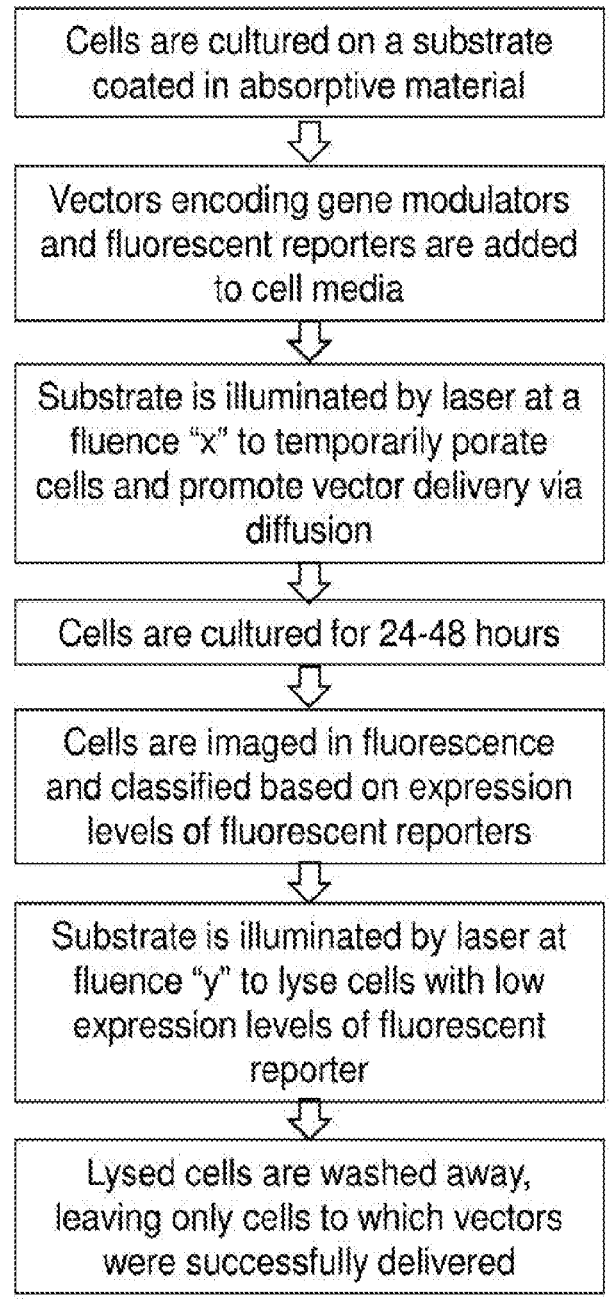
FIG. 26 diagrams an example workflow.

FIG. 26 diagrams an example workflow. Cells are cultured on a substrate coated in absorptive material. Vectors encoding gene modulators and fluorescent reporters are added to cell media. Substrate is illuminated by laser at a fluence "x" to temporarily porate cells and promote vector delivery via diffusion. Cells are cultured for 24-48 hours. Cells are imaged in fluorescence and classified based on expression levels of fluorescent reporters. Substrate is illuminated by laser at fluence "y" to lyse cells with low expression levels of fluorescent reporter. Finally, lysed cells are washed away, leaving only cells to which vectors were successfully delivered.

Laser System Configurations

The laser source used to mediate cell poration may be continuous wave but is preferably pulsed (to minimize thermal damage to cells and intracellular delivery cargo). In some embodiments, the pulse widths may range from 10 to 100 fs, 0.1 to 1 ps, 1 to 10 ps, 10 to 100 ps, 0.1 to 1 ns, 1 to 10 ns, 10 to 100 ns, 0.1 to 1 µs, or 1 to 10 µs. In certain embodiments, the laser system and wavelength used may be a 532 nm Nd:YAG, 1064 nm Nd:YAG, 650-1100 nm Ti:Sapphire, 980 nm diode, 351-528 nm Argon, 193 nm ArF, 248 nm KrF, 308 nm XeCl, 353 nm XeF, 390-435 nm stilbene, 460-515 nm coumarin, 570-640 nm rhodamine, 510 nm copper vapor, 578 nm copper vapor, 627 nm gold vapor, 1320 nm Nd:YAG, 694 nm ruby, 2940 nm Er:YAG, 2100 nm Ho:YAG, or 700-820 chromium-doped chrysoberyl (alexandrite) laser. The laser source may be frequency doubled or tripled to achieve a desired wavelength. The source may be a Q-switched laser. The laser source may be a fiber laser.

Depending on whether an absorbing material 2201 is used, the type and dimensions of the absorbing material (if used), and the laser characteristics, the fluence (energy/unit area) used may be within 1 to 10 mJ/cm^2, 10 to 100 mJ/cm^2, 0.1 to 1 J/cm^2, 1 to 10 J/cm^2, 10 to 100 J/cm^2, or 100 to 1000 J/cm^2. The exact fluence used will also depend on the application (cell poration vs cell removal/killing) and the distance between the absorber (if used) and the cells.

In some embodiments, the diameter of the laser beam spot may be in the range of 1 to 10 µm, 10 to 100 µm, or >100 µm. The diameter of the laser beam spot may depend on the chosen absorber, and the maximum power output of the laser source.

Configurations with Absorbers to Mediate Energy Transfer

The absorber used to mediate the energy transfer may comprise: (1) a patterned absorbing surface on which cells are cultured; (2) a non-patterned absorbing surface on which cells are cultured; (3) absorbing particles that are added to the cells/aqueous cell media; and/or (4) absorbing molecules that are added to the cells/aqueous cell media.

To transfer the optical energy from the laser light to mechanical energy via the formation of a bubble, the material used must have >0% absorption at the given laser wavelength. Depending on the application, the desired absorption may be >20%, >40%>60%, or >80%.

Absorbing Surfaces

If an absorbing surface is to be used to convert laser light energy to mechanical energy via the formation of a bubble, the surface must be designed to be both at least partially absorptive at the given laser wavelength and partially transmissive in the wavelength range used for imaging (400 to 700 nm).

The surface may be composed of a transparent material (e.g. glass, polystyrene, etc.) topped with a thin continuous non-patterned layer of absorbing material, a thin continuous patterned layer of absorbing material, and/or an array of absorbing structures.

The transparent material (glass, polystyrene, etc) may have a thickness on the order of 0.1 to 1 mm, or 1 to 10 mm, which would enable transmission of the imaging wavelengths. Depending on the application, the desired transmission may be >20%, >40%>60%, or >80%.

The absorbing surface may simply be an un-patterned continuous thin film of absorbing material that is deposited onto the transparent surface of the substrate. The thin film may have a thickness in the range of 1 to 10 nm, 10 to 100 nm, or 0.1 to 1 µm. The absorbing material may be a biocompatible metal or metal alloy such as Ti, Au, Ag, or TiN. In certain embodiments, the absorbing substrate may be composed of 0.3 mm of glass topped with a 20-nm thin film of Ti, or a 50-nm thin film of Au. The absorbing surface may also be composed of two metallic layers, with the metal layer between the transparent surface and second metal serving as an adhesive, such as 2 nm of Cr or Ti topped with 10 nm of Au. In some embodiments, other non-metallic absorbing materials could be used such as amorphous silicon, carbon black, indium tin oxide, or photoabsorbent polymer. The absorbing material may be deposited onto the transparent surface by sputtering, thermal evaporation, or electron-beam deposition.

In other embodiments, the absorbing material may be a patterned surface atop the transparent surface, as opposed to an un-patterned continuous thin film. The transparent surface could be covered in an array of absorbing structures, such as pyramids, spheres, discs, squares, rods, cavities, crescents, or pillars. The structures may have dimensions on the order of 1 to 10 nm, 10 to 100 nm, 0.1 to 1 µm, or 1 to 10 µm. The absorbing structures may be joined together by a continuous thin film of absorbing material (e.g. Ti, Au, TiN, Ag, carbon black, indium tin oxide, photoabsorbent polymer etc.) or may be independent structures spaced apart on a transparent substrate. In an example embodiment, the absorbing substrate could be composed of a 0.3 mm glass substrate topped with an array of 60-nm diameter 15-nm thick Au discs. Another example embodiment could be the negative of such an array—a 0.3 mm glass substrate topped with a continuous 15-nm thin film of Au, punctuated with an array of 60-nm diameter holes.

In certain embodiments, the bottom of the absorbing substrate (the non-cell facing side), may be coated with an anti-reflection coating to reduce reflection to <5% for a given laser wavelength. For instance, in certain embodiments, multiple layers of quarter-wave thick MgF2 coatings may be applied to the bottom of the substrate via physical vapor deposition, to achieve a reflectivity to below 1% at the chosen laser wavelength.

Absorbing Particles and Molecules Added to the Cells/Aqueous Cell Media

In other embodiments, the absorbers may not be attached to the transparent surface, but may be added to the cells or cell media. For instance, absorbing structures such as nanospheres, microspheres, nanorods, nanostars, or nanotriangles could be mixed in with the cell media and allowed to settle onto the cell membranes. The structures may have dimensions on the order of 1 to 10 nm, 10 to 100 nm, 0.1 to 1 µm, or 1 to 10 µm. These structures could be composed of any material designed to absorb at the given laser wavelength, such as metals or metal alloys (Ti, Au, Ag, TiN, etc.), carbon black, or photoabsorbent polymers. In certain embodiments, 20-nm diameter Au nanospheres may be added to cells cultured in a standard tissue culture-treated well plate. In another embodiment, 60-nm aggregates of carbon black could be added to cells cultured in a standard tissue culture-treated petri dish. The absorbing structures may also be composed of more than one material. In an example embodiment, the absorbing structures may be composed of 50-nm diameter Ag nanospheres coated in a 5-nm thick Au shell. In other embodiments, the absorbing materials may be photoabsorbent molecules added to the cell media, such as phenol red, allura red, or melanin. In an example embodiment, the cell culture surface may be coated in a hydrogel loaded with the vectors for intracellular delivery and with melanin designed to absorb at the given laser wavelength.

Example Embodiment without Absorbers

In an example embodiment, an 800-nm Ti:Sapphire laser with 100-femtosecond pulses may be tightly focused onto the membranes of induced pluripotent stem cells (iPSCs) cultured on a standard tissue culture-treated 96-well plate. Laser illumination results in the formation of temporary pores on the membranes of the iPSCs, enabling membrane-impermeable cargo in the surrounding cell media to diffuse into the cells before the pores close.

Example Uses and Embodiments

The invention described here could be used to guide stem cell differentiation and remove unwanted cells, resulting in a phenotypically-pure cell population. For instance, a surface could be composed of a 0.3-mm thick glass substrate coated on one side with a 20-nm thin layer of thermally evaporated Ti. On the other side, a quarter-wave thick layer of MgF2 is deposited via physical vapor deposition to minimize reflections. Induced pluripotent stem cells (iPSCs) are cultured in a monolayer on the Ti-coated side of the substrate. Episomal vectors encoding gene modulators and fluorescent reporters are added to the cell media. A 532-nm Nd:YAG laser with 7-ns pulses is focused onto the Ti surface (which absorbs >50% of the incoming 532-nm light), resulting in the formation of bubbles that porate the cell membranes, enabling the delivery of the membrane-impermeable episomal vectors. The gene modulators encoded in the episomal vectors initiate changes in cell fate. The cell population is imaged through the substrate (which transmits approximately 25-30% of light in the 400 to 700 nm wavelength range), and cells that have not received the desired gene modulators are identified by lack of expression of the fluorescent reporter and targeted for removal. The laser is focused onto the Ti surface beneath these cells (at a higher laser fluence than the fluence used for intracellular delivery), forming large bubbles that lift the targeted cells from the surface.

II. Systems and Methods for Heterogeneous Cell Culture Control

Related aspects of the disclosure use fluorescent reporters, imaging, and image-guided laser ablation to culture mixed populations of cells and selectively remove subpopulations of certain cells. Such methods allow cells to be grown in mixed, heterogeneous populations, which may be beneficial where one cell type secretes material essential to growth of another cell type. Image-guided laser ablation allows the first "helper cell" type to be selectively removed once the culture is mature. Such techniques generally provide systems and methods for heterogeneous cell culture control.

The disclosure provides methods for how collective behavior of cell culture may be manipulated and optimized by targeting single cells with gene expression-altering cargo, cell removal or by tagging cells with fluorescent molecules. Embodiments include delivering cargo at single-cell resolution to alter gene-expression to manipulate cell behavior.

The human body consists of over 200 tissue types and interactions between the cells in these tissues are crucial for cell type specification and function starting from embryonic stem cell differentiation during fetal development throughout our lives in the form of adult stem cells capable of repairing tissue damage. In one embodiment the invention provides methods and compositions of matter of how cell fate programs can be manipulated and niche conditions optimized towards a target cell state by changing gene expression at a single cell resolution in culture. Delivery and monitoring of the cargo and cell removal in this invention is done by image-guided laser-system. Such systems are described in: U.S. Provisional 62/756,141 (System for Generation of Cell Differentiation Programs); U.S. Provisional 62/841,946 (System for Directing Cell Culture); and International patent application PCT/US19/45969 (System for Image-Driven Cell Manufacturing), all incorporated by reference.

Some embodiments use deliverable fluorescent tags to optimize cell culture conditions. Fluorescent labeling based on molecules, (proteins, lipids, sugars etc.), pH-changes or DNA or RNA is a widely used method to identify cells. These methods allow the visualization of specific proteins in both fixed and live cell images. However, despite offering a single-cell resolution for live-cell imaging and identifying cells, the tools to modify cells based on this information has been lacking. This invention describes a laser-based tool to detect and modify cells at single-cell level based on the fluorescent reporters introduced into the cells, creating a controlled cell monolayer system.

Fluorescent reporters used with this invention can be of various kinds. In co-culture systems where several cell types are present, commercially available live-cell fluorescent dyes that bind cell-surface receptors can be used to detect different populations of cells. Image-based laser can then be used to remove unwanted populations to purify culture of these cells. Another method to introduce fluorescent reporters transiently to identify subpopulations in culture is to transfect cells with plasmids carrying a fluorescent reporter under cell/tissue-type specific promoter. Delivery of such plasmids can also be done by electroporation or with the invention described in this patent. These delivery methods allow for a window of approximately 48 hours to identify different cell types in the culture and when combined with the image-based laser, modify culture. Living cells can be also tagged transiently with pH-sensitive dyes emitting fluorescence only when exposed to intracellular compartments with specific pH, such as lysosomes or phagosomes, allowing for visualization of specific cell types. Fluorescent ion-sensitive live-cell markers are yet another group of tags that can be used to identify cells. For example, Calcium-sensitive cell-permeable indicators can be used to visualize calcium flow across cardiac and muscle cell membranes to identify cells able to contract. Similar method can be used to detect neuronal activity in cultured cells. When combined with the image-guided laser described in this invention, these methods can be used to tailor cell culture environment for downstream applications requiring e.g. high purity of single cell type, specific patterning of co-cultured cells or temporal support of "helper cells" of additional cell type.

If long-term fluorescent visualization is required, the abovementioned plasmids and indicators can be introduced into the cells by lentiviruses or transposase systems like PiggyBac or Sleeping Beauty. These systems are able to incorporate tags permanently into the genome and emit continuous fluorescence upon activation of the desired promoter/intracellular condition. Having the presence of such genome-altering components due to possible off-target effects can be detrimental for cells used in cell therapies. Thus the removal of such helper cells in the culture prior to transplantation is of high importance and can be done at high purity with the invention without disturbing the cell-cell interactions required by other available methods that rely on cell sorting to gain pure population of target cells.

The examples below describe ways in which the image-based laser can be used to temporarily manipulate co-culture conditions consisting of the desired cell type and the so called "helper cells" at various stages. Laser is used to remove these so called "helper" cells when their support to the culture is no longer needed and instead their presence could lead to undesired consequences from skewed results (drug/tox screens) to life-threatening complications (tumors, graft versus host disease (GgHD) upon transplantation). The helper cells described here can be of animal or human origin, primary or immortalized cell lines. Their desired helper function can also be a result of genetic alterations, such as overexpression of a gene involved in secreting desired molecules, or based on the cells inherent characteristics.

In vitro studies often use purified ECM proteins for cell culture coatings, however, these may not represent the molecular complexity and heterogeneity of the optimal ECM for the cells. To overcome this, in one embodiment fluorescently tagged helper cells like fibroblasts and/or epithelial cells are cultured on a plate and secrete extracellular matrix to cover the cell culture plate in its native, non-purified and most optimal form for cell adhesion and function. After ECM deposition by the fluorescently tagged or morphologically distinguishable helper cells, an image-guided laser can be used to remove them, while leaving the secreted ECM intact. Afterward, the desired cell type can be plated on top of the secreted matrix with optimal biological attributes for the target cells.

In one embodiment fluorescently tagged helper cells are cultured on a plate and secrete cytokines, hormones and/or growth factors required by the target cell type. When these factors are no longer needed (eg. desired differentiation stage has been achieved) Image-guided laser can be used to remove the tagged cells, leaving a pure population of target cells. Example of this type of helper cells are mouse and human embryonic fibroblast cells, that have been widely used to help accelerate hPSC differentiation towards various cell types, such as RPE's. See Hongisto, 2012, Low level of activin A secreted by fibroblast feeder cells accelerates early stage differentiation of retinal pigment epithelial cells from human pluripotent stem cells, Stem Cell Disc 2(4):176-186, incorporated by reference.

In one embodiment fluorescently tagged helper cells are cultured on a plate and act as helper cells for the target cell type at a specific stage of cell culture (Eg. differentiation) providing electrical or mechanical signals required by the other cell type. These support cells can be removed and/or their number can be controlled by image-guided laser to create the optimal conditions for the target cells. For example, for cardiomyocytes, only 1% of the cells in vivo contribute to controlling electrical conductivity and conduction rates that maintain the electrical impulses or action potentials across the tissue. Therefore in order to mimic the in vivo cardiac culture it is crucial to control the number of these pacemaker cells. See Stoppel, 2015, Electrical and mechanical stimulation of cardiac cells and tissue constructs, Adv Drug Deliv Rev 96:135-155, incorporated by reference.

The mechanical properties of cells influence their cellular and subcellular functions, including cell adhesion, migration, polarization, and differentiation, as well as organelle organization and trafficking inside the cytoplasm. The parameters used to measure mechanical properties are cell stiffness and viscosity.

In one embodiment fluorescently tagged helper cells neutralize toxic byproducts of the target cells maintaining viable cell culture conditions. Similarly, helper cells can be required for catalyzing the conversion of potentially therapeutic molecules into their active form that is taken up by the target cells, mimicking the in vivo therapeutic function and allowing for better cell culture model for pharmacokinetics and toxicology studies. See Efremova, 2015, Prevention of the degeneration of human dopaminergic neurons in an astrocyte co-culture system allowing endogenous drug metabolism, Br J Pharmacol 172(16): 4119-4132, incorporated by reference.

FIG. 27 shows an example embodiment of the present system. In this embodiment the system is employed to manage a co-culture of two or more cell types, one of which (darker) is the "target" cell type to be differentiated, and the other (lighter) is a "supporting" cell type.

Supporting cell types may include, but are not limited to cells that support the health and/or proper differentiation of the target cell and/or tissue. Those cells may be, for example, adult primary cells, genetically-enhanced cells (for the purpose of producing the cues listed below), stem cells with advance programming to differentiate into supporting cell types, or cells from other species (either genetically engineered or not).

The support cells may be chosen and/or genetically engineered to provide the stimuli listed below in response to an external signal—for example, but not limited to: optical signals, electrical signals, and chemical signaling.

The support cells may provide support and/or cues in the form of biochemical products.

Biochemical products that signal the target cell type to activate particular pathways, to promote health, proliferation, differentiation, and/or function and are transported by diffusion from the supporting cells to the target cells, either through cell media or directly from cell to cell. Various types of feeder cells, mainly fibroblasts, from animal and human origin are currently used for this purpose.

The support cells could, for example, be engineered to produce specific factors that are encapsulated, transported, and transferred to neighboring or nearby target cells. This could be done in response to an external stimulus, for example the addition of a small molecule, or a gene activator construct, in order to provide dynamic timing control of the delivery of these compounds. An interesting example of this are the cultured human olfactory neurons that release activin A in the medium upon addition of progesterone. These cells could be used in co-culture setting to secrete Activin A required by the differentiating cells towards the desired lineage at the specific time by adding progesterone into the medium. ("Expression and secretion of activin A: possible physiological and clinical implications" Luisi et al. 2001 European Journal of Endocrinology (2001) 145 225±236.).

Similarly, the widely used insulin growth factor 1 (IGF-1) secretion in co-culture system with mesenchymal cells could be used to drive differentiation of various cell types when temporally controlled. See Jeon, 2017, Insulin-like growth factor binding protein-6 released from human mesenchymal stem cells confers neuronal protection through IGF-1R-mediated signaling, Int J Mol Med 40(6):1860-1868, incorporated by reference.

An additional benefit of using a co-culture setting for timed secretion of molecules required for differentiation is, that each of the helper cell type can be potentially derived from patients own cells via initial hiPSC-derivation. This results in higher compatibility of the secreted factors to the target population and reduced risk of immunological rejection upon transplantation.

Supporting cells, or "helper cells", may provide biochemical products (i.e. proteins) that appear on the surface of the supporting cell, and signal the target cell by membrane-to-membrane interactions—thereby activating aforementioned pathways within the target cells.

The role of cell-surface molecules are especially important during hematopoietic differentiation, where receptor-ligand interactions govern the balance between self-renewal and differentiation. By providing a coculture with supporting cell population expressing the desired cell-surface ligands, the number of blood progenitors can potentially be increased and their differentiation can be controlled in temporal fashion by altering the availability of the crucial cell surface receptors of the helper cells. ("A ligand-receptor signaling threshold model of stem cell differentiation control: a biologically conserved mechanism applicable to hematopoiesis." Zandstra et al. Blood 2000 96:1215-1222.)

Biochemical products (i.e. intracellular matrix) may be emitted by the supporting cells into the surrounding medium and form a support matrix between cells, within the cell media, or on the tissue culture substrate, which in turn supports the health, proliferation, differentiation of the target cells or tissue.

One example for such an approach during co-culture differentiation is a system where a subpopulation of hepatocytes were modified genetically to overexpress a protein responsible for ECM secretion, leading to an increased hepatocyte differentiation in the non-modified hepatocyte population. By adding a fluorescent tag to the protein, our system could remove these gene-modified cells from the culture once the target cells are ready for further applications, such as transplantation, ensuring that no gene-modified cells are introduced into the transplant recipient. Hepatocytes are known to be very sensitive to dissociation and handling, and with current methods the pre-purification step would require harsh cell sorting methods, leading to compromised number and quality of transplantable cells. Hepatocyte culture protocols would benefit greatly from being able to remove non-desired cells while maintaining the target cells in adherent culture prior to downstream applications. ("LIM homeobox 2 promotes interaction between human iPS-derived hepatic progenitors and iPS-derived hepatic stellate-like cells." Miyoshi et al. 2019 Scientific Reports volume 9, Article number: 2072)

Supporting cells, or "helper cells", may provide important mechanical properties or cues.

Supporting cells have mechanical properties that impart signals to nearby target cells, causing them to proliferate, differentiate, and/or orient/polarize in a desirable manner. As an example, co-culturing retinal neural progenitors on the apical surface of the retinal pigment epithelium (RPE) cells has been shown to enhance their differentiation towards polarized photoreceptors. However, the tools to remove any incorrectly polarized helper RPE-cells currently do not exist, leading to suboptimal differentiation efficiency of the photoreceptors. ("Retinal Pigment Epithelial Cells Promote Spatial Reorganization and Differentiation of Retina Photoreceptors." German et al. 2008 J Neurosci Res. 2008 December; 86(16): 3503-3514.)

Supporting cells form—or are managed to form by the present invention—structures that specifically guide the proliferation, orientation, and/or polarization of the target cells and/or tissue. For example, the support cells may be patterned in "rows" along an axis, and cause the target cells to orient along this axis.

Supporting cells provide motion (such as muscle contractions) that stimulate or signal the targets cells appropriately to ensure proper differentiation, proliferation, orientation, etc.

Electrical cues: supporting cells produce electrical cues to ensure proper differentiation, orientation, polarization and function of the target cells and tissue; for example when growing neuronal cultures or tissues.

To expand upon the example of support cells providing stimuli in response to an external cue, an embodiment of the present invention could use neuronal or other cells that have been genetically modified to respond to optical signals of a particular wavelength, and produce one or more electrical impulses in response. In the present invention, such support cells, arranged within target cells (that are being differentiated and patterned into the target tissue) may be illuminated with said optical pulses in order to create regular electrical impulses across the cell/tissue culture. Such optical pulses could be varied spatially and/or temporally to optimize the differentiation, polarization, synapse formation, etc. of the target cell/tissue culture.

Cells that serve as an external indicator of the health, quality, function, phenotype, level of maturity or other property of the target cells or tissue:

Health and proliferation: the support cells may be chosen and configured such that they are "pushed out" by the target cells when the target cells are properly differentiating and/or proliferating. Alternatively, they may be chosen to proliferate well when the target cells are successfully growing/differentiating. In this case, observation of the supporting cells using the imaging systems described in the present invention may be used to track the success of the target cell/tissue culture.

Supporting cells, or "helper cells", may provide optical signaling. The supporting cells may be chosen—or, in many cases, genetically engineered—to provide externally detectable optical signals in response to target cell function in response to, for example, electrical activity. Supporting cells may be engineered to respond to local electrical/electrochemical signalling/potentials by fluorescing, thereby providing a localized readout of electrical activity in the target cells, as an example above with cardiac cells.

Supporting cells, or "helper cells", may be engineered to produce optical signals in response to local biochemical conditions indicative of target cell or tissue state.

Supporting cells may be engineered to produce optical signals in response to local mechanical conditions indicative of target cell or tissue state.

One or more support cell types may be used in a particular target cell or tissue culture. For example, multiple support cells types could be used to provide different cues throughout the target cell culture, potentially in response to external cues (optical pulses, small molecule signals, etc). In addition one or more "signaling" support cells may be used to assess the state of the target cell or tissue culture.

In systems and methods for heterogeneous cell culture control, supporting cells may be managed over the course of the cell/tissue culture to provide their respective functions.

Supporting cells may be managed over the course of the cell/tissue culture to provide their respective functions.

In many (but not all) cases, the supporting cells are removed at some point in the process, in order to allow the target cell types to fully proliferate, to allow for accurate downstream analysis of the target cells or tissue, and to prepare the cells or tissue for transplant into a patient.

In some cases, the supporting cells may remain in the tissue for transplant. For example, in animal studies, it may be beneficial to have supporting cells remain in the tissue to: externally stimulate the transplanted tissue through the mechanisms described above; or to externally monitor the success of the transplanted target cells/tissue through the mechanisms described above. An example of such co-transplantation is the beta-cell islet-mesenchymal stem cell co-culture, where the latter act as an inflammation-reducing and pro-angiogenic agent upon transplantation. ("Improved islet recovery and efficacy through co-culture and co-transplantation of islets with human adipose-derived mesenchymal stem cells. Gamble et al. 2018. PLoS ONE 13(11): e0206449. https://doi.org/10.1371/journal.pone.0206449).

Supporting cells may have image characteristics that are sufficiently distinct in label-free imaging modalities (such as brightfield, phase, differential interference contrast, darkfield, etc) when processed by the computing system described in the present invention, that they may be identified, managed and removed without specific fluorescent labelling. This type of label-free morphological analysis has already been used to predict differentiation potential of mesenchymal stem cells. ("Label-Free Morphology-Based Prediction of Multiple Differentiation Potentials of Human Mesenchymal Stem Cells for Early Evaluation of Intact Cells." Sasaki et al. 2014 PLoS One. 2014; 9(4): e93952.) However, in many cases it will be desirable to genetically engineer the support cells to express fluorescent proteins, so that they may be easily identified, located, and laser-managed within the target cell or tissue culture. This is in addition to the cell/tissue condition-responsive fluorescent signals described above.

Embodiment of the present disclosure provide a system for managing support cells together with target cells.

Figure 27A:
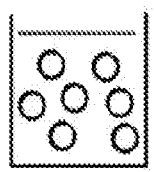
FIG. 27A shows supporting cells in suspension.

FIG. 27A shows supporting cells in suspension, prior to seeding in the culture vessel. In actuality there may be multiple supporting cell types, and these may be seeded into the vessel simultaneously, or sequentially with intervening patterning to manage local areal density and distribution.

Figure 27F:
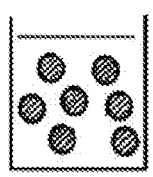
FIG. 27F shows a tube of target cells.
Figure 27B:
FIG. 27B shows the support cells as they are being seeded.

FIG. 27B shows the support cells as they are being seeded into the culture vessel. As is well known to those who have performed cell culture, the average areal density achieved by a particular volume and volume density of cells is not necessarily reflected in the ultimate distribution of cells adhering to the substrate.

Figure 27G:
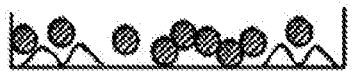
FIG. 27G shows that the target cells settle randomly.
Figure 27K:
FIG. 27K shows cell patterning.
Figure 27C:
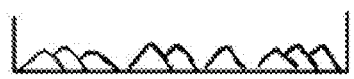
FIG. 27C shows an average areal density actually achieved.

FIG. 27C shows an average areal density actually achieved.

In the present invention, the optimal density, patterning, and organization of the supporting cells is calculated and compared to the actual distribution.

Figure 27H:
FIG. 27H shows that the target cells adhere to the cell culture vessel.
Figure 27L:
FIG. 27L shows laser removal of supporting cells.
Figure 27D:
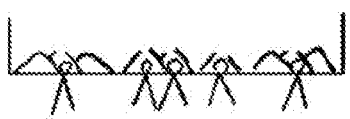
FIG. 27D shows use of a laser removal recipe.

FIG. 27D shows use of a laser removal recipe is calculated in order to remove adherent cells in a manner as to result in the best possible match to optimal conditions. In this example, a particular density of support cells, limited to a particular part of the culture substrate, is desired, as shown in the "scan result".

Figure 27I:
FIG. 27I shows actively managing the local cell density, ratios, and structure.
Figure 27M:
FIG. 27M shows removal of low functionality cells.
Figure 27E:
FIG. 27E shows the scan result, after removal of debris.
Figure 27J:
FIG. 27J shows a result.

FIG. 27E shows the scan result, after removal of debris.

FIG. 27F shows a tube of target cells that will be added to the culture plate. It should be noted that the order of operations (addition of support vs target cells, or multiple support cell types and multiple target cell types) will vary by protocol. In some cases support cells and target cells will be added to the plate/vessel simultaneously.

FIG. 27G shows that the target cells settle randomly.

FIG. 27H shows that the target cells adhere to the cell culture vessel surface or existing cells.

FIG. 27I shows use of the present methods to actively manage the local cell density, ratios, and structure. For example, cells that are not in a monolayer may be removed, in order to ensure 100% imageability of the cell/tissue culture for management in the present system. Target cells may be eliminated in certain areas to separate them from support cells, or may be removed in any area that does not contain support cells, depending on the support cell functions and the specific cell protocol.

FIG. 27K shows that in the present, highly simplified, example, target cells are patterned (by removal) so they start their proliferation from the center of the substrate, surrounded by support cells.

The imaging system, computing system, and pulsed laser targeting system in the present invention may be used to dynamically manage this distribution and patterning over the course of the tissue culture protocol. In this example, target cells start their differentiation, while simultaneously proliferating from the center outward. The support cells in this case are providing appropriate chemical cues—where the cues push appropriate differentiation, and chemical gradients could promote local proliferation and migration patterns.

FIG. 27L shows that when the target cell types have properly proliferated and differentiated to a specific stage, the system identifies and laser-removes the supporting cells. This is done at an early enough stage that the target cells move/divide into the resulting spaces in order to form a contiguous tissue (if this is a tissue product). Subsequently, and throughout the process, as has been described in other disclosures, the target cells may be in turn managed by the imaging-computing-laser system using predictive models for cell/tissue functionality—and cells or clusters that are predicted to have lower functionality are removed using the laser subsystem.

FIG. 27M shows removal of low functionality cells.

Figure 27N:
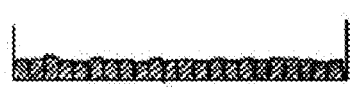
FIG. 27N shows a result.

FIG. 27N shows the result, whereby predicted to be higher-performing proliferate to fill these gaps, to ultimately form a uniform layer of highly-functional cells.

When supporting cells are only required for chemical support of the target cells, an insert (eg. Transwell) can be added into the well where a monolayer of target cells is growing.

Figure 28:
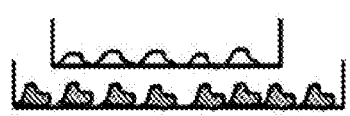
FIG. 28 shows insertion of a Transwell insert that includes helper cells.

FIG. 28 shows insertion of a Transwell insert that includes helper cells.

A homogenous population of helper cells is then added to the Transwell insert and forms a monolayer that secretes factors necessary to support target cells consisting of one or more subpopulations. In this setting the target cell culture can be further optimized by image-guided laser removal to include only the desired cells. Alternatively, the target cells can be cultured in the transwell inserts and the culture of helper cells can grow in the well and can be modified by image-guided laser as described above.

Figure 29:
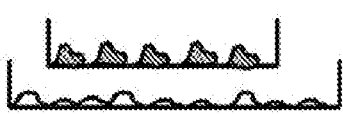
FIG. 29 shows the helper cells in the well with target cells in a Transwell.

FIG. 29 shows the helper cells in the well with target cells in a Transwell.

In certain embodiments, two target cell types are co-cultured and managed by the imaging—computing—laser system of the present invention in order to form specific tissues with heterogeneous cell types. While this example shows two types of cells, the present invention may be used to manage the growth of tissue with many cell types, some types "programmed" from the start to result in a specific cell type, and others emergent during tissue culture. In some embodiments temporal vectors are used with heterogeneous (target cell/helper cell) culture control to provide for differentiation of pluripotent cells in a spatially-specific manner in order to produce patterned functional tissue for transplant. For example the cells may be differentiated into rod and cone cell type photoreceptors for retinal therapies, where rod and cone ratios must be adjusted across the tissue sheet to match the distribution in an adult retina.

FIG. 30A shows a first cell type prepared for plating. A first set of cells has been transfected with a first type of inducible episomal vector which encodes a series of gene modulators designed to differentiate the cell into a rod photoreceptor.

FIG. 30B shows the first cell type plated onto the cell culture surface, settling randomly. The calculated cell seeding density is generally chosen to be higher than the ultimately desired density, as the system will be employed to locally adjust density to the optimum level.

FIG. 30C shows the first set of cells settles on the vessel and adheres in a random pattern. The adherent cell distribution over the surface manifests some time after seeding; the system then uses an image-based system to locate cells, calculate local cell density, and calculate an optimal cell removal strategy to match the optimal cell density across the substrate.

FIG. 30D shows the removal process. Cells from the first set of cells are removed based on the imaging subsystem, as processed by the computing subsystem, using the laser subsystem described in the present invention, where cells are lysed using a photomechanical (microbubble) effect resulting from conversion of pulsed laser energy into microbubbles; cells are removed based on factors recognized by the imaging and computing subsytems including but not limited to: overlapping cells, leading to the inability to properly image and monitor; non-optimal cell density for proper differentiation into rod photoreceptors in the early stage of differentiation; non-delivery of the ieVector as evidenced by lack of fluorescence by the delivery reporter on the vector; and non-activity of the ieVector (after chemical induction) as evidenced by the transcription reporter on the vector.

FIG. 30E shows an idealized post-removal cell distribution according to certain embodiments. It should be noted that the ideal distribution for a particular cell may not be individual cells in isolation, but rather clusters of a certain numbers of cells, or patterns of cells such as stripes, circles, etc. Throughout the process the cell media may contain small molecules to generally drive differentiation (into retinal progenitor types), while the ieVectors drive specific subtypes.

FIG. 30F shows a second cell type prepared in suspension. A second set of cells has been transfected with a second type of ieVector which encodes a series of gene modulators, in this example into cone photoreceptors. "Cell type" may refer to a cell that has is different phenotype than the first cell type, or has been pre-programmed to differentiate into a different cell type, for example through gene activation by any one of a number of mechanisms, including but not limited to the episomal vectors as described in an earlier disclosure (discussed above). In another example, the first cell type is differentiated to a certain point using small molecule or other differentiation protocols, and then the second cell type is added, which may be at an earlier point of differentiation, and the small molecule recipe changed upon adherence of this second set of cells, causing the first and second cell types to ultimately differentiate into two distinct mature cell types. This process is by no means limited to two cell types.

FIG. 30G shows that the second cell type settles randomly into the culture vessel.

FIG. 30H shows that the cells then adhere to the surface, or to the prior plated cell. Again, a certain local density, ratio of cell types, or patterns of cell types that are desirable can be achieved using imaging, computing system generation of optimal removal patterns, and laser cell removal.

FIG. 30I shows laser cell removal. Image-guided laser removal of cells optimizes the local density and type of cells; also to remove non-delivered or non-transcribing cells as described above.

FIG. 30J shows a distribution resulting from laser cell removal.

FIG. 30K shows how cells proliferate and differentiate. This may include differential rates of proliferation, and cases where cells no longer are in a monolayer. The invention uses image-based guidance and its computing subsystem to identify those cells that are no longer in a monolayer, region-specific cell ratios and densities that deviate from the optimal, etc. to identify cells for removal. For example, the ultimate tissue in this case calls for islands of one cell type within another cell type, and a variation in the size of these islands over the extent of the tissue created. The precursor cells are managed via prediction in the image computing model, and ratios adjusted by location accordingly using the laser processing. Proliferation and differentiation of cells may be based on general cell media (with small molecule factors driving differentiation generally towards retinal subtypes), induced gene modulator transcription from the ieVectors based on chemical inducers added at specific timepoints, and general cell culture conditions including cell-cell interactions and cell-substrate interactions.

FIG. 30L shows the process of removal. Removal of cells is preferably based on imaging, computing subsystem recognition, and pulsed laser removal, based on one or more of the following (not exhaustive list): Removing cells that are growing in a way where they are no longer observable by the imaging subsystem; Removing cells that are not properly differentiating, or recognized to be differentiating in a way that will result in lower than desirable mature cell function; Removing cells where density is too high; and Removing cells where ratio between cell types is non-optimal. At a later stage in tissue differentiation and formation (potentially after multiple cycles of imaging, computing of cell and tissue characteristics vs the ideal trajectory, and laser removal to correct trajectory), individual cells or groups of cells may be removed based on their predicted functional characteristics. For example those cells with lower predicted functionality may be removed, and nearby higher-function (or more correct phenotypically) cells divide and/or migrate in order to fill the resulting gap—thereby resulting in a more functional final tissue.

FIG. 30M shows further differentiation of cells, and additional imaging-computing-laser-based cell removal to remove cells that are predicted to result in non-optimally functional mature cells, based on functional prediction models stored in a storage subsystem. After re-filling of these gaps, and further differentiation/maturation, the final tissue has the desired local as well a global structure for the target organ.

FIG. 30N shows the final tissue with the desired structure for the target organ. The resulting sheet of cells shows high cell functionality, purity (absence of non-differentiated cells which could result in teratomas upon transplant), and patterning resembling adult tissue—in this case proper rode/cone ratios across the surface of the photoreceptor layer.

When supporting cells are only required for chemical support of the target cell populations, an insert (eg. Transwell) can be added into the well where a monolayer of target cells is growing.

FIG. 31 shows target cells grown in a monolayer in a well with support cells in a transwell. This monolayer can be modified in any way described. A homogenous population of helper cells is then added to the Transwell insert and forms a monolayer that secretes factors necessary to support target cells consisting of one or more subpopulations. In this setting the target cell culture can be further optimized by image-guided laser removal to include only the desired cells, as described above. Alternatively, the target cells can be cultured in the transwell inserts and the culture of helper cells can grow in the well.

FIG. 32 shows helper cells in the well, where cells may be modified by image-guided laser as described above.

Figure 33A:
FIG. 33A shows use of a laser to pattern extracellular matrix (ECM).

FIG. 33A shows use of a laser to pattern extracellular matrix (ECM) deposited on the surface of the substrate (before adding any target or helper cells).

Figure 33B:
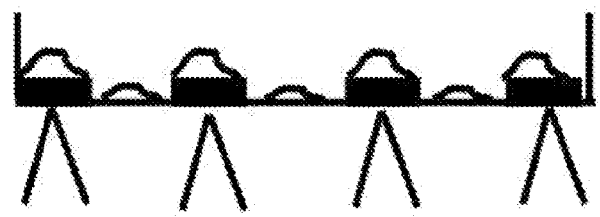
FIG. 33B shows cells added to the well.

FIG. 33B shows cells added to the well. The cells added on the well will selectively adhere to the area covered with ECM. When these cells are stimulated to differentiate into the desired direction, their progeny will be able to secrete the required matrix specific to these cells and then migrate to these areas.

Figure 33C:
FIG. 33C shows use of a laser to remove the original ECM.

FIG. 33C shows use of a laser to remove the original ECM and cells growing on it, after which the cell progeny can fill the remaining gaps as in FIG. 3c.

The desired target cell population may include of non-adherent cells that bud off the adherent target cell layer during differentiation as in the case of various types of blood and immune cell maturation. These cells can be collected for downstream applications during regular cell medium change and centrifugation, while keeping the adherent cell culture intact.

III. Optical Cell Processor

An optical cell processor may be integrated with heterogenous cell culture management and tissue engineering in conjunction with induced episomal vectors for cell state control. That integrated combination allows programming of cell state transitions using temporal vectors and then cell-level management of the process to result in the desired cell types or combination of cell types.

The combination of heterogeneous cell culture control, temporal vectors, and optical cell processors according to the present disclosure provides several feature. The present disclosure provides spatially-selective removal of cells from the vessel by optical means, for the purpose of: removing cells that did not have a vector delivered (determined by imaging fluorescent delivery reporters; removing cells that do not transcribe the ieVectors (determined by imaging fluorescent transcription reporters in the ieVector(s)); removing cells to control local cell density, including removing cells that have been delivered with varying temporal vectors in order to adjust local cell ratios or patterning (where "no delivery" is also a type); and removing cells identified to be incorrectly or sub-optimally transitioning cell states, as determined by imaging and computing subsystem comparison to established feature models.

IV Photolithographic System for Cell Culture Control and Measurement

Further related aspects of the disclosure relate to cell manipulation techniques rooted in photolithography concepts. Photolithography approaches are used to create spatial masks to protect or ablate sets of cells or to build up controlled layers of different cell types and biological materials. Such approaches generally provide photolithographic systems for cell culture control and measurement.

Many advances have been made in stem cell culture and differentiation into progenitor or mature cell types, for the purpose of building realistic tissue for drug screening or even therapeutic cell and tissue replacement therapies. One ongoing challenge is the precise control over cell culture and tissue morphology, and, where multiple cell types are desired in a single tissue sample, the ratio, distribution, and local patterning of those multiple cell types. Generally, all cells within a particular cell culture vessel are acted upon similarly by cell culture conditions, including the use of small molecule additives to the cell media that serve to drive cell differentiation.

One approach is to allow cells to form "organoids" where clusters of cells emerge and often free-float (even if the original cells were adherent on a substrate) and spontaneously differentiate into multiple cell types with organization roughly along the lines of natural tissue, but typically at a much smaller scale, and with an overall morphology drastically different from adult tissue. Organoids such as these have been formed for applications such as drug screening in "brain organoids." However, for therapeutic applications, cells that are formed in an organoid must be separated and sorted before transfer to a patient in a relevant manner—in the process structure and patterning are lost.

One emerging approach to more precisely recapitulating tissue structure, including heterogeneous tissues, is the application of 3D printing techniques to tissue engineering. While this is theoretically attractive, the current state of the art is limiting, in that most techniques offer only low resolution (not cell-level) and often suspend cells in a large volume of hydrogel matrix material, leading to structures that have very low initial cell density. As such, the initial cells supplied into the printing system must be in a state of rapid proliferation, and therefore generally pluripotent or at most in a progenitor stage. For much of the cell differentiation process, therefore, there is little or no individual control over cell fates, and as a result low control over the microstructure of the emerging tissue, with the risk that cells do not properly differentiate, causing functional deficiencies or raising the risk of teratoma formation in therapeutic applications.

Perhaps the most mature, well-understood and consistent tissue culture format—the culture of adherent cells on the surface of culture vessels such as tissue culture flasks and well plates—is seen as a poor format for building mature and heterogeneous tissue because of the lack of control over cell differentiation in a spatially-controllable manner. This format does, however, have one enormous advantage: the ability to image cell cultures and emerging tissues with high fidelity, and the potential to operate upon the culture at a single-cell level.

Photolithography-based embodiments of the disclosure provide methods for performing spatial operations upon adherent cell cultures at a single-cell level, where the operations are optically defined—enabling very high resolution (down to single-cell level) and at the same time opening the door to very high throughput processing of 2D and 2.5D (a few layers of cells) cell culture and tissue processing.

The system is based on "photolithography" where, similar to their use in the semiconductor industry, operations are performed by the use of temporary layers that are optically defined on the substrate of interest (in our case, an adherent cell culture). Unlike the semiconductor application, however, all steps in our system are biocompatible, using materials that are non-toxic, allow delivery of nutrients to underlying cells, and use exposing wavelengths that are not phototoxic to cells.

Photolithography-based embodiments of methods of the disclosure generally include: optical patterning of a biocompatible temporary hydrogel layer ("mask") onto an adherent cell culture; performing an operation upon the cell culture, with the application or non-application of the operation defined by the mask; and removing the temporary layer. operations that may be performed on the cell culture include deposition of new cells; removal of existing cells; and delivery of cargos to existing cells. Those elements may be included in a method of creating and using a spatially-defined mask over an adherent cell culture.

The optical patterning may be driven by a computing system that processes an image of the existing cell culture, determines which areas the operation should be performed on, and then provides a signal to the optical mask-patterning source to form the appropriate temporary mask upon the cell culture.

Figure 34:
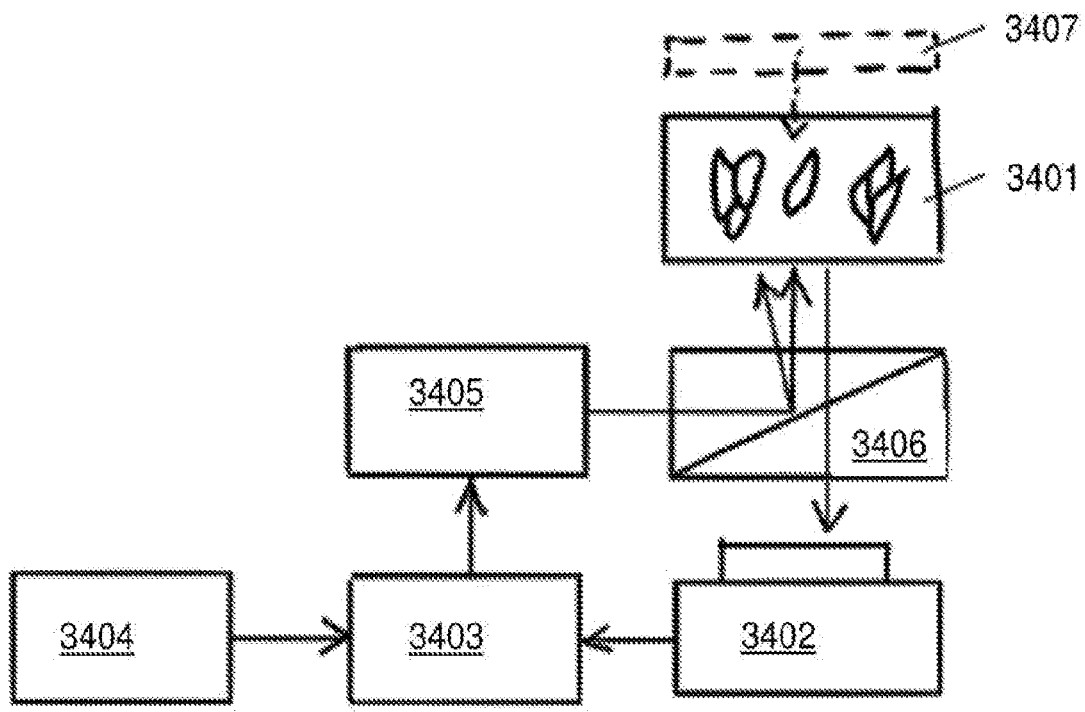
FIG. 34 shows a system for optically creating a spatially-defined mask.

FIG. 34 shows a system for optically creating a spatially-defined mask over an adherent cell culture. The depicted system (discussed in greater detail in another section below) is useful for photolithography embodiments.

Preferred embodiments of the spatially defined mask use biocompatible hydrogel materials that are photo-responsive for use as a mask. Good summaries of photo-responsive hydrogels may be found in Ruskowitz, 2018, Photoresponsive biomaterials for targeted drug delivery and 4D cell culture, Nature Reviews/Materials 3(2):1-17 and Pereira, 2015, 3D Photo-Fabrication for Tissue Engineering and Drug Delivery, Engineering 1(1):90-112, both incorporated by reference.

Ideal masking materials should fulfill the following requirements: (1) can be photo-patterned, in the presence of cells, either by (a) bulk depositing onto cells and selectively curing them with light (ie photo-curable), by (b) bulk depositing onto cells and selectively removing them with light (ie photo-cleavable), or by (c) selectively depositing them onto targeted cells using laser-induced forward transfer (LIFT) and then polymerizing (ie photoresponsive, thermoresponsive, etc); (2) allow basic cell nutrients to pass through them, so maintain cell health; (3) are temporary (typically), and can therefore be removed; and (4) and can serve as either a barrier to prevent passage of certain compounds, or as a reservoir to hold certain compounds. Examples of biocompatible materials that fulfill requirement (1) include: photo-curable polymers, such as polymers functionalized with photoreactive moieties (acrylates, methacrylates or norbornene pendant groups), Gelatin-MA, collagen-MA, hyaluronic acid-MA, chitosan-MA, alginate-MA, tropoelastin-MA, glycol chitosan, heparin, dextran, PEG-DA, PEG-norbornene, HA-norbornene, gelatin-norbornene (thio-ene chemistry). Table 1 lists Polymers with photoinitiators that absorb light and generate free radicals to initiate free radical polymerization, such as: Irgacure 2959 (1-[4-(2-hydroxyethoxy)-phenyl]-2-hydroxy-2-methyl-1-propane-1-one), LAP (lithium phenyl-2,4,6-trimethylbenzoylphosphinate), VA-086 (2,2'-azobis[2-methyl-N-(2-hydroxyethyl)propionamide])

Table 1 lists polymers with photoinitiators that absorb light and generate free radicals to initiate free radical polymerization.

TABLE 1

Polymers with photoinitiators that absorb light and generate free radicals to initiate free radical polymerization

| Photo-initiator | Absorption λ (nm) | Light Intensity | Time (sec) | Extinction Coefficient (365 nm) |
|---|---|---|---|---|
| Irgacure 2959 | 365 | 5-10 mW · cm$^{-2}$ | 15-30 | <10 M$^{-1}$cm$^{-1}$ |
| LAP | 365/405 | 10 mW · cm$^{-2}$ | 120-300 | 200/30 M$^{-1}$cm$^{-1}$ |
| VA-086 | 365 | 2 mW · cm$^{-2}$ | 300 | |

Table 2 lists polymers with photoinitiators that require a co-initiator, such as: Eosin-Y, riboflavin.

TABLE 2 lists Polymers with photoinitiators that require a co-initiator

| Photo-initiator | Absorption λ (nm) | Light Intensity | Time (sec) | Extinction Coefficient (365 nm) |
|---|---|---|---|---|
| Eosin-Y | 515 | 10 mW · cm$^{-2}$ | 240 | 100 000 M$^{-1}$cm$^{-1}$ |
| Riboflavin | 400-500 | 300 mW · cm$^{-2}$ | 120-600 | |

FIG. 35 shows patterned deposition of photo-curable polymers onto adherent cells. Table 3 lists Photo-cleavable polymers, such as: polymers functionalized with photoreactive moieties, which are very common (acrylates, methacrylates or norbornene pendant groups), such as gelatin-MA nitrobenzyl ester, PEG-courmarin azide, or PEG-nitrobenzyl/courmarin. Other photo-cleavable polymers, such as: Ru(bipyridine)2(3-pyridinaldehyde)2 (RuAldehyde), Coumarin-based esters, Ortho-Nitrobnezyl, or photocleavable protein PhoCI.

TABLE 3

Photo-cleavable polymers

| Photo-cleavable Linker | Absorption λ (nm) | Dosage (mW/cm$^2$) | Degradation time/area |
|---|---|---|---|
| RuAldehyde | 400-500 | 14 | 50 min/20 mm$^2$ |
| Coumarin-based esters | 400-450 | | |
| o-Nitrobenzyl | 305-365 | 28 | 8 min/2.5 mm$^2$ |
| PhoCl | 400 | 10 | 0-30 min |

FIG. 36 shows patterned deposition of photo-cleavable polymers onto adherent cells. Examples of biocompatible materials that fulfill requirement (2) include polymers/hydrogels that are porous to enable nutrient diffusion. This includes polymers for which the porosity can be controlled by varying crosslinking density, the concentration of monomers, crosslink time, and/or the photoinitiator concentration. In certain embodiments, the polymer may be poly(lactic-co-glycolic acid) (PLGA), a copolymer of lactic and glycolic acid. In PLGA, the monomers are linked together by ester linkages which are hydrolytically cleavable. By controlling the ratio of lactic and glycolic acid, it is possible to control properties of the hydrogel such as porosity. In other embodiments, the polymer may be a GelMA hydrogel. The porosity of GelMA hydrogel can be controlled by varying the concentration of photoinitiator. For instance, at a 0.05% concentration of Irgacure 2959 photoinitiator, the average pore size is approximately 1800 μm2; at 0.25% concentration of Irgacure 2959, the average pore size is approximately 800 μm2; and at 0.5% concentration of Irgacure 2959, the average pore size is approximately 400 μm2.

Examples of biocompatible materials that fulfill requirement (3) include those that can be removed with chemical means, time, temperature, or other means. Chemical means include enzymes. Examples of such enzymes include collagenases, hyaluronidases, trypsin, and gelatinase. Examples of enzyme-degradable hydrogels include naturally occurring polymers and polymers embedded with matrix metallopeptidase (MMPs) sensitive linkers. Hydrolytically-cleavable polymers such as PLGA degrade over time in an aqueous cell culture environment due to the inclusion of ester bonds that are cleaved in the presence of water. In certain embodiments, the ratio of monomers to cross-linkers present in PLGA could be tuned to control the degradation kinetics. Thermo-responsive polymers such as PIPAAm, Pluronic F127, and non-crosslinked gelatin. Other means include pH level, mechanical disturbances, or cell phagocytosis.

Examples of biocompatible materials that fulfill requirement (4) include those that act as a barrier to certain compounds. In some embodiments, this may be achieved by optimizing the pore size and hydrogel thickness to prevent diffusion of molecules over a certain size. In some embodiments, this may be achieved by photo-crosslinking "barrier" regions such that the "barriers" are more solid/less porous, therefore blocking chemicals by slowing diffusion kinetics. In some embodiments, diffusion kinetics may be slowed by configuring a polymer to contain many small pores. In some embodiments, a hydrogel may be crosslinked with peptides that can covalently bind proteins and molecules, therefore trapping them in the hydrogel. For instance, PEG-based thiol-norbornene hydrogels may include peptide links to bind small molecules, growth factors, and/or RNA/DNA. In certain instances, a PEG-based thiol-norbornene hydrogel may be configured to trap vectors encoding genetic effectors.

In some embodiments, hydrophilic hydrogels may be used to repel hydrophobic vectors (lipofection delivery), and/or hydrophobic pockets within the hydrogel may be used to trap hydrophobic (liposomes) molecules within the pockets. In other instances, a charged hydrogel, such as hyaluronic acid, could be used to repel negatively charged nucleic acid vectors.

FIG. 38A gives an example of a patterned masks serving as a barrier to protect cells from delivery.

Biocompatible materials that fulfill requirement (4) include those that function as a reservoir that incorporates certain compounds. In some embodiments, the polymer may be loaded with small molecules that diffuse out of the porous polymer, and into nearby cells, over time. In some embodiments, regions of the hydrogel may be loaded with molecules for delivery, and then photo-degraded in those regions to release molecules onto cells. Examples of photo-cleavable polymers that could be used for this application include polymers with PhoCl, nitrobenzyl, and coumarin cross-linkers. In some embodiments, water-degradable polymers may be used to release molecules to nearby cells over time. In certain embodiments, the temporal dynamics of the water-degradation process may be modified or sped up with photocleavable degradation.

FIG. 39 gives a first example of a patterned mask serving as a reservoir of delivery cargo for cells.

FIG. 40 gives a first example of a patterned mask serving as a reservoir of delivery cargo for cells.

Patterning of the Optically-Defined Mask

The optically-defined mask described in the present invention may be applied to the cell layer in one of three ways:

FIG. 35A through FIG. 35D shows a process by which a mask material precursor with photo-crosslinkers may be added on top of the cells and selectively illuminated in targeted regions (where there are cells that do not require intracellular delivery) with a wavelength to initiate cross-linking. The selective exposure may be achieved with a scanning laser, projection system (e.g. Texas Instruments DLP), or fixed photomask (e.g. a patterned mask that produces the desired tissue patterning). The un-cross-linked precursor would then be washed away, resulting in a cell culture in which specific cells are covered and protected by the mask, while other cells are exposed.

FIG. 36A through FIG. 36D show a process by which a mask material precursor with photo-cleavable linkers may be added on top of the cells and polymerized (this may be achieved via non-optical means). The mask may then be selectively illuminated in targeted regions (where there are cells that do require intracellular delivery) with a wavelength to initiate cleavage of bonds. The selective exposure may be achieved with a scanning laser, projection system (e.g. Texas Instruments DLP), or fixed photomask (e.g. a patterned mask that produces the desired tissue patterning). The un-cross-linked precursor would then be washed away, resulting in a cell culture in which specific cells are covered and protected by the mask, while other cells are exposed.

FIG. 37A through FIG. 37C show a process in which Laser-induced forward transfer (LIFT) may be used to deposit hydrogel material onto selected cells. A donor substrate may be covered in a (potentially liquid) form of the mask precursor material, and droplets of this may be LIFT-ejected onto select cells. The deposited mask precursor may then be polymerized (via optical means, via modulation of temperature, etc), thereby protecting the covered cells. In the case of photopolymerized masks that are LIFT-deposited, flood exposure may be used (ie selective exposure is not necessary).

For a description of the types of optical subsystems that can be used to photo-cure, photo-cleave, or LIFT-eject the mask precursor materials, see Optical Subsystems for Mask Definition.

Example Embodiments and their Applications

The optically-patterned masks described in the present invention may be used for a variety of applications, including:
(1) masking targeted cells to prevent delivery via conventional means such as viral delivery or lipofection.
(2) masking targeted cells to prevent removal of the covered/protected cells.
(3) masking targeted cells with a cargo-loaded hydrogel to provide chemical cues to the cells via diffusion of the molecular cargo.
(4) masking followed by lift-off for patterned deposition of cells.

Some example embodiments of these applications are described below.

Example Embodiment 1: Optically-Patterned Barrier Masks for Patterned Delivery

In some embodiments, an imaging subsystem may be used to obtain images of cells in a 2D culture, and determine which cells require intracellular delivery of cargo. The cell media may be removed, followed by addition of an optically-defined mask. The optically-defined mask may be applied in any of three previously described ways. After patterning the mask, a solution containing the desired delivery cargo may then be added. This cargo may include, but is not limited to: CRISPR RNPs, CRISPRa, CRISPRi, TALENS, Zn-fingers, vectors encoding genetic effectors and/or fluorescent reporters, gRNAs, plasmids, episomal vectors, photoreceptor outer-rod segments, cell nutrients, photoreceptor outer-rod segments, etc. The delivery cargo may be capable of entering the cells on its own (ie membrane-permeable), or may be membrane-impermeable and combined with a delivery modality such as (but not limited to) viral vectors, lipid complexes, peptides enabling endocytosis, or electroporation. In some instances, delivery may be achieved via mechanical means that temporarily disrupt the cell membrane, including but not limited to: laser-induced forward transfer (LIFT) ejection of cargo-loaded droplets, shear forces from liquid flow, or ultrasonic bubble-mediated poration. Next, the remaining cargo may be washed out, followed by removal of the protective mask. As previously mentioned, removal of the mask may be achieved by chemical means, over time, via change in temperature, or via other means. Such an embodiment could be used to drive cell differentiation in a spatially-patterned manner, for example by patterning delivery of vectors encoding genetic modulators.

FIG. 38 gives a first example of this.

FIG. 42 gives a second example of this.

Specific Example 1.1, Polyethylene Glycol (PEG) and Photopolymerization as a Mask In some embodiments, the chemical configuration of the hydrogel mask could be a radical chain photopolymerized poly(ethylene glycol) hydrogel functionalized with nor-bornene groups, degradable metalloproteinase peptide (MPP) linkers, and photoinitiator Irgacure 2959.

Figure 35A:
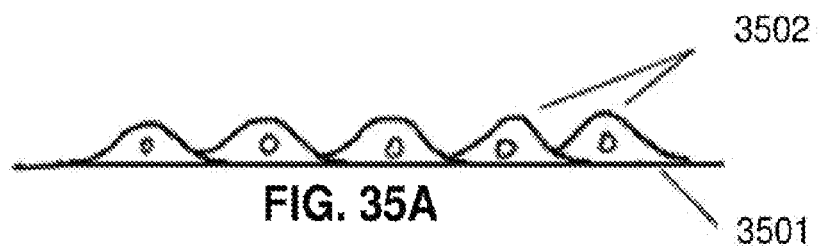
FIG. 35 shows patterned deposition of photo-curable polymers onto adherent cells.
Figure 35B:
Figure 35C:
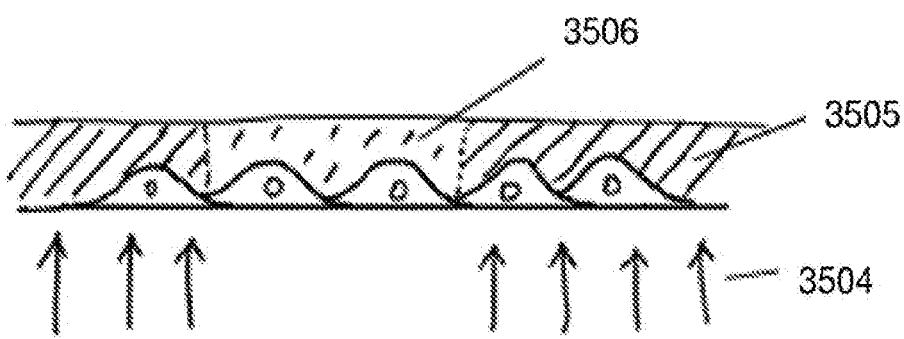
Figure 35D:

FIG. 35B and FIG. 35C shows that following photopolymerization, the non-crosslinked areas are removed via washing with cell media to create a patterned mask. After delivery to the un-masked cells, the hydrogel mask could be removed by chemical degradation using 1 U/mL of collagenase type 1 enzyme, which cleaves the MMP degradable peptides. The thin hydrogel mask is digested in 10-20 minutes at 37 degrees C. The remaining decomposed hydrogel is washed and removed with cell culture media.

In certain embodiments, this hydrogel mask solution is comprised of 10% weight by volume PEG-norbornene, MMP degradable peptide and 0.05% weight by volume Irgacure 2959 photoinitiator in phosphate buffered saline or cell media solution. This composition could be modified in a number of ways, such as:

Increasing the percent PEG-norbornene, MMP or photoinitiator concentration to increase the crosslinking density, increase the stiffness of the hydrogel, and/or decrease pore size (resulting in decreased diffusion kinetics).

Varying the volume of the mixture to adjust the thickness of the hydrogel mask. The ideal thickness will allow for fast polymerization while still maintaining diffusion of nutrients and preventing diffusion of vectors to "masked" areas. We estimate a thickness of 100-200 μm will be best. A reasonable estimate of photo-curing time and energy for a 200 μm thick hydrogel mask is 5 minutes of exposure at 365 nm with a light intensity of 5 mW/cm2. Irgacure 2959 molar absorptivity at 365 nm ε<10 M-1 cm-1.

Specific Example 1.2, Natural Polymer and Photopolymerization as a Mask

In some embodiments, the chemical configuration of the hydrogel mask may be a chemically-modified gelatin hydrogel. Methacrylate gelatin contains cell binding domains and is hydrophilic, which allows for permeability of small molecules such as cell nutrients. When mixed with a photoinitiator, the methacrylate groups allow for free-radical polymerization and covalent crosslinking.

FIG. 35B and FIG. 35C shows that following photopolymerization, the non-crosslinked areas are removed via washing with cell media to create a patterned mask. After delivery of cargos (for instance, vectors encoding gene modulators) to the unmasked cells, the hydrogel mask is removed by chemical degradation using 1-5 U/mL of collagenase type II enzyme. The thin hydrogel mask is digested in ~10-20 minutes at 37 degrees C. The remaining decomposed hydrogel could be washed and removed with cell culture media.

To create the mask, a solution of 10% GelatinMA and Irgacure 2959 is mixed in phosphate buffered saline and pipetted onto the cell layer. This composition could be modified in a number of ways, such as:

To adjust the porosity of the GelMA hydrogel the concentration of photoinitiator can be varied. For instance, at 0.05% Irgacure 2959 concentration the average pore size is ~1800 μm^2; at 0.25% Irgacure 2959 the average pore size is ~800 μm^2, at 0.5% Irgacure 2959 the average pore size is ~400 μm^2. Smaller pores may be more desirable, in certain applications, to prevent diffusion of vectors to the masked/protected cells.

To adjust the thickness of the hydrogel mask, various volumes of the mixture can be added to the cell monolayer while maintain ratios of solution components. We estimate a size of 100-200 μm will be ideal. A reasonable estimate of photo-curing time and energy for a 200 μm thick hydrogel mask is 10 minutes of exposure at 365 nm with an intensity of 8 mW/cm2.

Specific Example 1.3, Mask w/Visible Light-Mediated Crosslinking

In some embodiments, the chemical configuration of the hydrogel mask is a step-growth, visible light mediated polymerization of poly(ethylene glycol)-tetra-norbornene.

FIG. 35B and FIG. 35C shows that following photopolymerization, the non-crosslinked areas are removed via washing with cell media to create a patterned mask. After delivery of cargos to the unmasked cells, the hydrogel mask is removed via hydrolytic degradation of the ester links within the PEG macromonomers. The timescale depends on the thickness of the mask but could take hours to days.

To create the mask, a solution of 10% weight PEG-tetra-norbornene, 1 mM dithiothreitol (thiol containing cross-linker) and 0.1 mM eosin-Y photoinitiator is mixed in phosphate buffered saline is added on to the layer of cells. This composition could be modified in a number of ways, such as:

To adjust the thickness of the hydrogel mask, various volumes of the mixture can be added to the cell monolayer while maintain ratios of solution components. We estimate a size of 100-200 μm will be ideal to prevent vector diffusion onto the masked cells. A reasonable estimate of photo-curing time and energy for a 200 µm thick hydrogel mask is 4 minutes of 515 nm light with an intensity of 10 mW/cm^2.

Specific Example 1.4, PEG and Photocleavable Linkers as a Mask

In some embodiments, the chemical configuration of the hydrogel mask is a poly(ethylene glycol) (PEG) diacrylate containing photocleavable linkers. The photocleavable hydrogel is created by step-polymerization of a four-arm PEG functionalized with an acrylated, o-nitrobenzyl ether monomer and a four-arm poly(ethylene glycol) functionalized with thiol end groups. Step-polymerization is performed via a base-catalyzed, Michael addition reaction.

FIG. 36B shows that the photocleavable PEG mask precursor is placed on top of the cells and allowed to polymerize.

FIG. 36C shows that predetermined areas are irradiated and therefore degraded, and these degraded mask regions are removed via washing with phosphate buffered saline or cell media. Cargo is delivered to the resulting un-masked cells. After cargo delivery, the remaining hydrogel mask is photodegraded using the same parameters previously described and washed away with cell media.

To adjust the thickness of the hydrogel mask, various volumes of the mixture can be added to the cell monolayer while maintaining ratios of solution components. For a hydrogel of 200 µm thickness, we estimate that photodegradation would take ~10 minutes with irradiation at 365 nm and intensity of 10 mW/cm^2.

Specific Example 1.5, LIFT-Ejection of Thermoresponsive Polymers for Masking

In some embodiments, the chemical configuration of the hydrogel mask may be a poly(N-isopropylacrylamide), a temperature-responsive polymer which could be used to form a mask onto the cell surface using LIFT. At a temperature close to the polymer's lower critical solution temperature (LCST) (32 degrees C.) the polymer would be a viscous liquid that would attach to the donor substrate via surface tension and/or viscous forces. Following LIFT-ejection of the droplets onto selected regions of the cell surface, the cell culture layer would be moved to physiological relevant 37 degree C. incubator. Above the LCST, the poly(N-isopropylacrylamide) would phase transition to a gel and act as mask. Cargo may then be delivered to the unmasked cells, while the masked cells are protected from the delivery cargo. For instance, this polymer is hydrophobic and would be able to block lipofection vectors from accessing the masked cells. Following delivery, the hydrogel mask is removed by removing the cell media/delivery cargo suspension, and replacing it with cell media at room temperature (<32 degrees C.) and incubating the cell culture layer below 32 degrees C. for 10-20 minutes. The poly(N-isopropylacrylamide) will phase transition back into a liquid and be washed away and replaced with fresh media.

Specific Example 1.6, LIFT-Ejection of Natural Cross-Linked Polymers for Masking In some embodiments, natural bio-inks or polymers could be used to form a mask on the cell surface via LIFT deposition. Gelatin, hyaluronic acid, collagen, chitosan, alginate and tropoelastin are examples of natural biocompatible polymers that can be functionalized with photoreactive moieties to allow for optically-defined crosslinking after LIFT-deposition. In an example embodiment, a prepolymer solution containing gelatin methacrylate, peptide linker and photoinitiator is applied to donor substrate. The solution is then deposited onto select cells via LIFT deposition. Following deposition to the cell layer, the solution can be photocrosslinked at a specified wavelength and intensity. Cargo can then be delivered to the unmasked cells, followed by removal of the mask.

Example Embodiment 2: Optically-Patterned Masks for Selective Cell Removal/Harvesting As with the previous example embodiments, imaging and image analysis is used to determine cells of interest. In this embodiment, as in previous embodiments, the mask can be patterned and optically-defined using the methods described previously (as depicted in FIG. 35A through FIG. 37C), but the mask serves to "hold down" some cells, while the unmasked cells are removed. In some embodiments, this may be used simply for cell management (maintaining a specific cell density, keeping desirable cells/colonies while washing others away), or for selective harvesting of cells of interest (for analysis, or re-plating). In the case of selectively harvesting unmasked cells of interest, the mask may not have to be temporary, nor does it necessarily have to be conducive to cell health.

Specific Example 2.1, PEGDA and Photoinitiators for Masking

In some embodiments, a photo-initiated cross-linked hydrogel could be used to mask cells that are not of interest for downstream collection. For instance, polyethylene glycol diacrylate (PEGDA) with a biocompatible photoinitiator Irgacure 2959 could be used. Irg2959 is activated at 365 nm wavelength and allows for light-based spatial control over polymerization of the hydrogel. The crosslinking/gel formation would be performed on top of cells that we do not wish to harvest. Following gel formation, a naturally derived chemical enzyme can be added to the wells, which is used to dissociate cells of interest. This enzyme would cause the unmasked cells to be released, and harvested for downstream analysis or re-plating.

FIG. 41 shows this process. The exact enzyme used will depend on the type of cells and matrix which it is grown. In some embodiments, the enzyme used may be a collagenase specific to a certain type of collagen (I, IV etc), or a trypsin enzyme to remove the cell colonies. In one embodiment, an example protocol might be:

1. Wash cells and PEGDA hydrogel with PBS
2. Add collagenase/trypsin enzyme
3. Incubate for 5-15 minutes at 37 degrees C.
3. Add media to stop enzyme reaction and collect removed cells for next application The porosity, thickness and stability of the "masking" hydrogel would be optimized to ensure the collagenase enzyme does not diffuse through it or degrade it. PEGDA is attractive for this application because it is a synthetic polymer which will not be degraded by natural enzymes and should have minimal influence on the surrounding cells.

Example Embodiment 3: Optically-Patterned Masks Loaded with Cargo for Delivery

As with previous embodiments, imaging and image analysis is used to determine cells of interest, and the mask can be patterned and optically-defined using the methods described previously. However, in this embodiment, the hydrogel is loaded with molecules for intracellular delivery. For instance, the hydrogel may act as a nutrient reservoir and be loaded with small molecules, proteins, peptides, or oligonucleotides. In some embodiments, oligonucleotides may be covalently attached to the polymer with photocleavable linkers. In other embodiments, the hydrogel may be loaded with induced episomal vectors with inducible expression of gene modulators, for the purpose of differentiating the masked cells. The cargo loaded within the hydrogel is then delivered to the masked cells. This delivery may be accomplished by simple diffusion of the cargoes from the gel to the cells, or may be spatio-temporally released, for instance by using light to degrade photocleavable polymers at a desired rate.

Specific Example 3.1, Loaded Mask with Controllable Pore Size to Control Delivery FIG. 40A through FIG. 40D show embodiments in which a barrier mask 4002 may be used in conjunction with a cargo-loaded mask 4001 for precise spatial control over delivery.

For the barrier mask 4004, a mixture of poly(ethylene glycol) functionalized with norbornene groups, metalloproteinase degradable linker peptide, and a photoinitiator Irgacure 2959 can be added to the layer of cells. For instance, the mask solution could be comprised of 20% weight by volume PEG-norbornene, MMP degradable peptide and 0.25% weight by volume Irgacure 2959 photoinitiator in phosphate buffered saline or cell media solution. By increasing the percent PEG-norbornene, MMP or photoinitiator will increase the stiffness or the hydrogel and decrease pore size. For the 4004 blocking mask, high monomer concentration and higher crosslinking will increase stiffness and reduce swelling of the hydrogel. These properties will decrease the diffusion of delivery vectors by decreasing the water content. To adjust the thickness of the hydrogel mask, various volumes of the mixture can be added to the cell monolayer while maintain ratios of solution components. We estimate a thickness of 200-500 μm will be best. A reasonable estimate of photo-curing time and energy for a 200 μm thick hydrogel mask is 5 minutes of exposure at 365 nm with a light intensity of 10 mW/cm2. After deposition of the 4004 barrier mask and removal of the uncrosslinked precursor material for the 4004 barrier mask, the delivery mask 4001 is added.

The delivery mask 4001 is loaded with cargo 4003 for delivery. The delivery mask 4001 should have a lower crosslinking density and monomer concentration. This will decrease the stiffness, increase pore size, increase swelling and allow for faster diffusion of delivered vectors/molecules that are released. One potential chemical configuration for 4001 is a photodegradable hyaluronic/PEG hydrogel mixed with plasmid DNA, small molecules, or vectors for delivery. A prepolymer solution of 4% weight/volume hyaluronic acrylate, 4% weight/volume four-arm poly(ethylene glycol) acrylate, plasmid DNA vector, and 1% weight/volume Irgacure 2959 is added to the masked cell layer. To adjust the thickness of the hydrogel mask, various volumes of the mixture can be added to the cell monolayer while maintaining the ratios of solution components. We estimate a thickness of 200 μm will be best. A reasonable estimate of photo-curing time and energy for a 200 μm thick hydrogel mask is 5-7 minutes of exposure at 365 nm with a light intensity of 10 mW/cm^2. To quickly release the 4003 molecules/vectors in the delivery mask 4001, chemical degradation can be applied. The 4001 delivery mask is composed of hyaluronic acid monomers which can be degraded using hyaluronidase enzyme. The hyaluronidase enzyme is specific for the delivery mask 4001, but will not affect the blocking mask 4002, which will remain intact. The plasmid DNA will be released and delivered into the 4005 cells covered in the delivery mask 4001 but not to the 4006 cells covered with the blocking mask 4002.

After successful delivery and degradation of the delivery mask 4001, the blocking mask 4002 can be removed via degradation with an enzyme to degrade the MMP peptides, followed by washing with cell culture media to remove the un-crosslinked solution.

Example Embodiment 4: Optically-Patterned Masks for Patterned Deposition of Cells FIG. 43A through FIG. 43F show an embodiment in which a temporary mask is used to pattern the deposition ("seeding") of new cells onto a cell culture surface, which may or may not already contain an existing layer of cells.

Figure 43A:
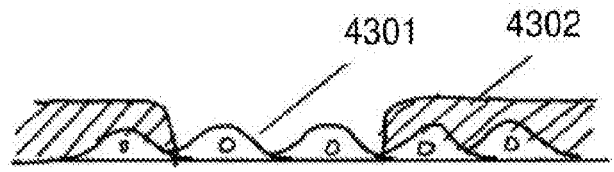
FIG. 43A shows a removal operation.
Figure 43B:
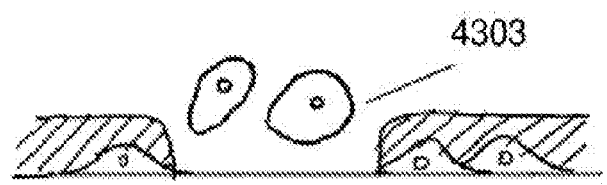
FIG. 43B shows removal of unmasked cells.
Figure 43C:
FIG. 43C shows a cleared-off mask.
Figure 43D:
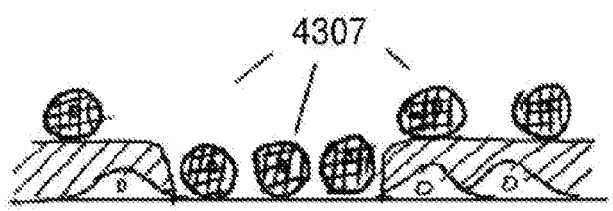
FIG. 43D shows addition of new cells.
Figure 43E:
FIG. 43E shows one step a "lift-off" mode of photolithography.
Figure 43F:
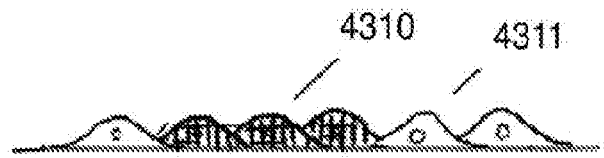
FIG. 43F shows results of the lift-off mode.

A method for patterned deposition of cells includes: applying of an optically-defined mask 4302 (the mask can be patterned and optically-defined using the methods described previously) to a substrate; seeding of new cells 4307 into the substrate (these generally fall randomly into the vessel); adhering the new cells 4307 onto the substrate, including both to areas that are exposed 4305 (open, in the hydrogel mask) and covered by hydrogel 4306; and removing the mask along with the cells that adhered to the mask. In some embodiments the hydrogel layer may be designed specifically to resist cell adherence;

FIG. 43F shows a 2D surface with multiple cell types patterned across it.

The process may be repeated multiple times in order to pattern multiple cell types across a 2D surface, or in multiple layers to form a 3D structure with precisely defined structure. The process may be driven by a computing system that images the existing cell culture, determines where cells should be added, and instructs the optical exposure system accordingly in order to form the appropriate temporary mask.

Optical Subsystems for Mask Definition

For masks that are photo-defined, either by selective curing (FIG. 35C) or selective removal (FIG. 36C), various optical subsystems may be used.

A scanned laser system may be used where a focused laser is steered (through an objective) by means of a galvanometric mirror, acousto-optic deflector, or other means; a means of optical amplitude control that is synchronized with this beam scanning; these all controlled by a computing subsystem; where the beam successively acts on the precursor hydrogel material to cure it or remove it; where the spot formed by the laser is sized to provide appropriate resolution; for example less than 100 μm, less than 25 μm, less than 10 μm, less than 5 μm. The scanned laser system may be monitoring by the imaging subsystem and computing subsystem to calibrate position and intensity in order to achieve proper patterning in a closed-loop manner.

A projection system may be used where an optical source (laser or LED) illuminates an area of the cell culture larger than the desired resolution, in combination with a photomasking system which spatially modulates the light projected onto the surface; for example, an LED source may be collimated and projected through a digital micromirror device (DMD), with a computing subsystem providing pixel-wise instructions in order to project light onto the precursor material. An imaging subsystem may provide initial information on the cell culture in order to compute the appropriate mask, and provide real-time alignment and exposure feedback in order to accurately expose the system. In some embodiments, where a fixed pattern of cells is desired or acceptable, static photomasks consisting of opaque or reflecting material on a transparent substrate may be used to project a pattern on the cell culture and hydrogel precursor.

For masks that are applied via laser-induced forward transfer (LIFT) of hydrogel onto the cell culture surface (FIG. 37B), a laser is used to eject droplets of mask precursor solution from a donor substrate towards the cell-containing surface. Examples of potential configurations for the donor substrate and laser system are given.

In some embodiments, the donor subsystem must include a material that is at least semi-absorptive at the wavelength of the laser source used to initiate LIFT. Furthermore, to enable imaging, the donor substrate may be at least partially transparent in the wavelength range used for imaging (400 to 700 nm). For instance, the donor substrate may be composed of a transparent material such as glass or polystyrene, coated in an layer of absorbing material.

The transparent material (glass, polystyrene, etc) may have a thickness on the order of 0.1 to 1 mm, or 1 to 10 mm, which would enable transmission of the imaging wavelengths. Depending on the application, the desired transmission may be >20%, >40%>60%, or >80%.

The absorbing surface may simply be an unpatterned continuous thin film of absorbing material that is deposited onto the transparent surface of the substrate. The thin film may have a thickness in the range of 1 to 10 nm, 10 to 100 nm, or 0.1 to 1 µm. The absorbing material may be a biocompatible metal or metal alloy such as Ti, Au, Ag, or TiN. In certain embodiments, the donor substrate may be composed of 0.3 mm of glass topped with a 20-nm thin film of Ti, or a 50-nm thin film of Au. The absorbing surface may also be composed of two metallic layers, with the metal layer between the transparent surface and second metal serving as an adhesive, such as 2 nm of Cr or Ti topped with 10 nm of Au. In some embodiments, other non-metallic absorbing materials could be used such as amorphous silicon, carbon black, indium tin oxide, or photoabsorbent polymer. The absorbing material may be deposited onto the transparent surface by sputtering, thermal evaporation, or electron-beam deposition.

In other embodiments, the absorbing material may be a patterned surface atop the transparent surface, as opposed to an unpatterned continuous thin film. The transparent surface could be covered in an array of absorbing structures, such as pyramids, spheres, discs, squares, rods, cavities, crescents, or pillars. The structures may have dimensions on the order of 1 to 10 nm, 10 to 100 nm, 0.1 to 1 µm, or 1 to 10 µm. The absorbing structures may be joined together by a continuous thin film of absorbing material (e.g. Ti, Au, TiN, Ag, carbon black, indium tin oxide, photoabsorbent polymer etc.) or may be independent structures spaced apart on a transparent substrate. In an example embodiment, the donor substrate could be composed of a 0.3 mm glass substrate topped with an array of 60-nm diameter 15-nm thick Au discs. Another example embodiment could be the negative of such an array—a 0.3 mm glass substrate topped with a continuous 15-nm thin film of Au, punctuated with an array of 60-nm diameter holes.

In certain embodiments, the opposite side of the donor substrate (the side not covered in absorbing material/structures), may be coated with an anti-reflection coating, to reduce reflection to <5% for a given laser wavelength. For instance, in certain embodiments, multiple layers of quarter-wave thick MgF2 coatings may be applied to the non-absorbing side of the donor substrate via physical vapor deposition, to achieve a reflectivity to below 1% at the chosen laser wavelength.

In other embodiments, the absorbers may not be attached to the transparent surface, but may be contained in the aqueous film coating the transparent donor substrate. For instance, absorbing structures such as nanospheres, microspheres, nanorods, nanostars, or nanotriangles could be suspended in the aqueous film. The structures may have dimensions on the order of 1 to 10 nm, 10 to 100 nm, 0.1 to 1 µm, or 1 to 10 µm. These structures could be composed of any material designed to absorb at the given laser wavelength, such as metals or metal alloys (Ti, Au, Ag, TiN, etc.), carbon black, or photoabsorbent polymers. In certain embodiments, 20-nm diameter Au nanospheres may be suspended in the aqueous film, or attached to cells cultured on the transparent donor substrate. In another embodiment, 60-nm aggregates of carbon black could be suspended in an aqueous film coating the substrate. The absorbing structures may also be composed of more than one material. In an example embodiment, the absorbing structures may be composed of 50-nm diameter Ag nanospheres coated in a 5-nm thick Au shell. In other embodiments, the absorbing materials may be photoabsorbent molecules suspended in the aqueous film coating the donor substrate, such as phenol red, allura red, or melanin. In an example embodiment, the donor substrate may be coated in a hydrogel containing cargo for intracellular delivery and melanin designed to absorb at the given laser wavelength.

The absorbers in the donor subsystem may transfer optical energy to mechanical energy via the generation of a pressure wave following the expansion and collapse of a bubble, following the vaporization of a material, and/or following the thermal expansion of a material. These processes require >0% absorption at the laser wavelength by the absorbing material. Depending on the application, the desired absorption may be >20%, >40%>60%, or >80%.

The laser source used to initiate LIFT may be continuous wave but is preferably pulsed (to minimize thermal damage to intracellular delivery cargo, in the case of deposition of loaded masks).

In some embodiments, the pulse widths may range from 10 to 100 fs, 0.1 to 1 ps, 1 to 10 ps, 10 to 100 ps, 0.1 to 1 ns, 1 to 10 ns, 10 to 100 ns, 0.1 to 1 µs, or 1 to 10 µs. In certain embodiments, the laser system and wavelength used may be a 532 nm Nd:YAG, 1064 nm Nd:YAG, 650-1100 nm Ti:Sapphire, 980 nm diode, 351-528 nm Argon, 193 nm ArF, 248 nm KrF, 308 nm XeCl, 353 nm XeF, 390-435 nm stilbene, 460-515 nm coumarin, 570-640 nm rhodamine, 510 nm copper vapor, 578 nm copper vapor, 627 nm gold vapor, 1320 nm Nd:YAG, 694 nm ruby, 2940 nm Er:YAG, 2100 nm Ho:YAG, or 700-820 chromium-doped chrysoberyl (alexandrite) laser. The source may be a Q-switched laser. The laser source may be a fiber laser.

Depending on the absorbing material used in the donor substrate and the laser characteristics (wavelength, pulse width, peak intensity, etc.), the fluence, or energy/unit area, used may be within 1 to 10 mJ/cm^2, 10 to 100 mJ/cm^2, 100 to 1000 mJ/cm^2, or 0.1 to 1 J/cm^2.

In some embodiments, the diameter of the laser beam spot may be in the range of 1 to 10 µm, 10 to 100 µm, or >100 µm. The diameter of the laser beam spot may depend on the chosen absorber, and the maximum power output of the laser source.

FIG. 34 shows an overall diagram of a system useful in photolithography embodiments. A cell culture substrate 3401 (such as a culture flask, well plate, or other substrate suitable for adherent cell culture and imaging) carries a cell or tissue culture that is imaged by an imaging system 3402. This image is processed by computing system 3403, which uses parameters from a storage system 3404 to assess cell or tissue culture conditions. Based on these conditions, which may be calculated globally across the substrate, locally in cell colony or per-area, the computing system generates a map for the photolithography course features to be produced as described in the present invention. This may include one or more masks to be applied to the cell culture.

An optical subsystem 3405 produced an optical pattern which serves to define the mask layer over the cells in the culture. This system may include, but is not limited to: scanning laser systems (scanned and projected by means of galvanometric mirrors, acousto-optic modulators, diffractive elements, etc), projection systems using spatial modulators such as digital micro mirror devices (DMDs) or liquid crystal arrays, or other devices which serve to spatially pattern light on the cell-bearing substrate, or optional sacrificial substrate 3407 in close proximity to the cell-bearing substrate.

The projected light may be projected onto the substrate through an optical combining device such as a beamplitter 3406, which serves to allow registered projection and imaging so as to enable cell-level application of masks based on image characteristics, down to the subcellular level.

FIG. 35A through FIG. 35D show an embodiment of the mask-writing system.

FIG. 35A shows that cells 3502 are cultured or deposited on a substrate 3501. An imaging system is used to determine which areas of the cell culture should be masked. Cell media is removed, and a hydrogel precursor 3503 that is photo-crosslinkable is added to the cell culture.

FIG. 35C shows the precursor is selectively exposed using patterned illumination 3504 in order to cure (polymerize) the hydrogel in regions above the cells to be masked (3505) and leave it uncured over regions of cells to be left exposed 3506. The layer thickness may be defined by the amount of precursor added to the cell culture (i.e. the depth of the added liquid), and/or optically, for example where a laser at the curing wavelength is focused such to have a narrow distance range where its intensity is sufficiently high to cure the hydrogel in a given time. After selective curing, the uncured precursor is washed away and replaced with cell media, with some cells left exposed directly to the media 3508, and others covered with a layer of hydrogel 3507 with specific properties. This hydrogel is generally still permeable to compounds necessary for basic cell health, as well as certain small molecules, but may have lower permeability to larger molecules. This mode of the present invention is similar to "negative resist" in semiconductor photolithography processes.

FIG. 36A through FIG. 36D show a "positive resist"-equivalent process of the present invention.

FIG. 36A shows cells 3602 on a substrate 3601 are imaged, and cells to be masked by a hydrogel are identified by a computing system.

FIG. 36B shows a hydrogel layer 3603 is deposited and cured. Selective exposure to light of the appropriate light 3604 by an optical projection system leaves some regions 3605 uncured, while the remainder 3606 are cured. What results is a cell culture with regions of cells that are covered by the hydrogel 3608 and others that are left open to the cell media 3607.

FIG. 37A through FIG. 37C show an embodiment of the mask-forming system described in the present invention. In this embodiment, laser-induced forward transfer (LIFT) of hydrogel is used to form a mask on a cell culture surface. The starting point is a substrate 3701 with a cell culture 3702 present on it.

FIG. 37B shows the deposition of the hydrogel mask. Pulsed laser light 3703 is used to create pulsed heating as it is absorbed on a substrate 3704 which may consist, for example, of a thin metallic layer, such as a 50 nm layer of Titanium. The pulsed light may be pulses on the order of <100 nsec in order to confine the heating temporally. The rapid and highly confined heating leads to an expansion of the absorber layer and/or vaporization of local liquid within the hydrogel layer 3705. The rapid bubble formation causes the ejection of a microdroplet 3707 of hydrogel, off the illuminated area 3706, which then impinges and settles upon the cell culture layer as indicated by 3708. The impact of this layer upon the cell culture surface may additionally cause the temporary poration of cell membranes, allowing delivery of large otherwise membrane-impermeable molecules, as described elsewhere herein.

FIG. 37C shows that the resulting mask covers areas of cells with a hydrogel layer 3710, while leaving other areas exposed as indicated by 3709.

FIG. 38A through FIG. 38D show an embodiment of the present invention, specifically its use in selectively delivering active compounds to cells, in a spatially-patterned manner.

FIG. 38A shows a cell culture that has been partially masked by an optically-determined hydrogel layer. This layer has lower permeability to a cargo 3801 which is added to the cell media. This cargo may be a molecule that can directly enter cells, or a complex (such as a liposome, or exosome) that promotes transport across cell membranes, a virus which transits cell membranes, or a molecule or construct that may pass through the membrane due to an external stimulus such as an electric field or mechanical force (for example ultrasound or pulsed laser cavitation)—but is not limited to these; generally this compound or particle will, under the right conditions, pass through the cell membrane as depicted by 502—but at the same time, does not easily pass through the hydrogel mask formed upon the cell culture by the system described in the present invention, as depicted by 3803.

FIG. 38B shows that, upon removal of the compound/particle/composition 3801 from the cell culture, and the removal of the hydrogel mask, the masked cells 3805 will not have the cargo delivered, while the unmasked cells 3806 will have the compound within their cytoplasm, nucleus, or organelles, or attached to surface receptors.

FIG. 38C shows that the interaction results in a differential effect on cells that were masked or not masked, as indicated by 3805 and 3804.

FIG. 38D shows that ultimately, in this example, this drives different paths of cell differentiation, and therefore results in patterned tissues with heterogenous cells (3808 and 3809).

FIG. 39A through FIG. 39D show another example embodiment, after patterning of hydrogel layers.

FIG. 39A shows that two masks 3901, 3902 of hydrogel have been patterned on the cell culture. In the present invention, multiple masks may be co-deposited, or deposited at different points in a cell culture process. In this case, one mask 3901 that carries a construct to be delivered to a subset of cells is patterned over the target cells. A second mask 3902, which does not carry a cargo, but blocks the prior cargo from being inadvertently delivered to non-target cells, covers those non-target cells. In most cases, as done in semiconductor processes, this mask would be patterned to be slightly larger than the first mask.

FIG. 39B shows entry of the cargo carried in the first gel into the proximate target cells, as well as diffusion of the cargo into the media 3904. The cargo in the media is blocked from entering non-target cells by the second gel 3902. Both gels provide continuous fresh media and small molecules to the underlying cells to promote cell health, proliferation, differentiation. The cell media may contain small molecules for the purpose of directing overall differentiation into a class of tissue, with the cargo that is the subject of the current embodiment specifying cell subtypes in a patterned manner, within the resulting tissue.

FIG. 39C shows the cells after removal or degradation of the aforementioned hydrogels, with (in this case) differentiation-driving cargos delivered only to target cells (in addition to overall factors delivered in cell media before or after patterned delivery, and factors delivered through hydrogel from media during patterned phase).

FIG. 39D shows an example final tissue, where cell type 3907 resulting from the cargo delivery has proliferated and differentiated, and cell type 3908 has proliferated and differentiated into a different cell type (no cargo 3904 being delivered).

FIG. 40A through FIG. 40D show a similar embodiment of the operations. In this embodiment a first temporary hydrogel 4002 mask is patterned onto a cell culture.

FIG. 40A shows that a second temporary hydrogel 4001 which is loaded with cargo to be delivered to selected cells is deposited over the cell culture, including over the first mask. The second layer may be deposited uniformly over the entire cell culture, or also patterned by optical means. The cargo, for example, may be episomal vectors in a delivery vehicle, such as viruses or lipofection complexes.

FIG. 40B shows that the cargo is delivered over a release time into the cells that are exposed to the second gel 4003, while the cells under the first mask 4004 are blocked from delivering the cargo, because the hydrogel is designed to be impermeable (or, sufficiently slow diffusion of) the cargo, but still permeable to supply nutrients to the cells. Subsequently both masks are removed and the cell culture is washed, and the cells progress towards differentiation as described above.

FIG. 41A through FIG. 40D show another embodiment of the present invention. In this embodiment, the selective application of a hydrogel mask 4102 leaves some cells 4101 exposed.

FIG. 41B shows that these cells 4103 are removed from the cell culture. The cell lift-off can be performed in a number of manners known to those versed in the art of cell culture—for example trypsinizing, or using a chemical that breaks up extracellular matrix.

FIG. 41C shows removal of cells from the culture.

FIG. 41D shows collection of cells.

This process may be performed by the present invention for a number of applications: (1) it may be used to remove cells from the ultimate cell culture—cells that are not desired in the final cell culture; or (2) to select out specific cells and collect them, without those covered by the hydrogel mask. In this second application, this can be done for a number reasons. For example, the "selected" (unmasked) cells may be collected for analysis, in order to connect their imaging characteristics within the cell culture to downstream analytical characteristics, such as (but not limited to) RNA expression analysis such as PCR, RNAseq and single-cell RNAseq; proteomic analysis; epigenetic marker analysis. In another example, these cells could be used for further differentiation into ultimate target cells, either in suspension or by re-plating onto another surface. In some cases, where cell differentiation protocols result naturally in a transition from adherent to suspension for properly-differentiating cells, the present invention, in the current embodiment, may be used to "de-select" cells that may not be optimally differentiating by masking them, while letting properly-differentiating cells release form the surface into the cell media, and ultimately into the downstream cell production process.

Figure 42A:
FIG. 42A shows a hydrogel mask.

FIG. 42A through FIG. 42 C show an embodiment of the present invention where a mask is applied both to control delivery of biochemical compounds in a spatially-controlled manner, but also functions as a mechanical template to enhance proper cell differentiation, growth, and polarization.

FIG. 42A shows a hydrogel mask 4201 that is patterned with the aforementioned methods, leaving open channels 4202 over certain target cells. These channels may be cylindrical, trenches, or other patterns depending on the desired tissue patterning and morphology.

Figure 42B:
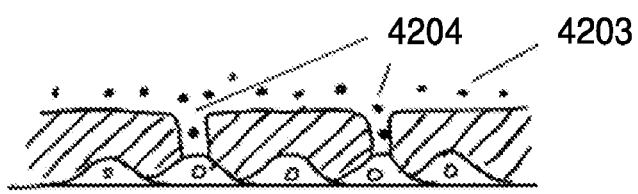
FIG. 42B shows a factor added to the cell media.

FIG. 42B shows that a factor 4203 is added to the cell media that has slow/no diffusion through the hydrogel mask, but travels down the channels as shown by 4204. This factor could directly drive differentiation of the target (exposed) cells, or be a chemoattractant that causes cells to elongate/migrate—or a combination thereof.

Figure 42C:
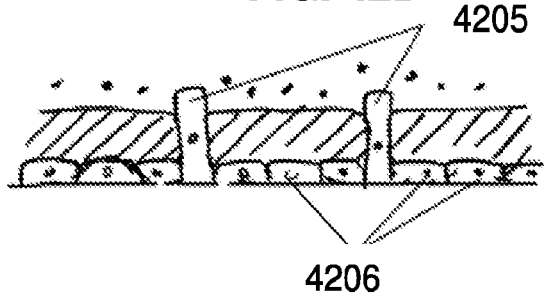
FIG. 42C shows target cells have differentiated.

FIG. 42C shows this process is shown, where the target cells have differentiated/morphed into a shape, defined by the channels and factors.

FIG. 43A through FIG. 43F show operations in another embodiment of the present invention; in this case a composite of two operations performed by the invention. The first operation is a selective removal operation, where an existing set of cells 4301 cultured on a surface is selectively masked by a temporary hydrogel mask 4302 that is patterned optically. Exposed cells are then removed as indicated by 4303 (trypsinized, for example), while cells under the mask remain adhered to the surface. This results in areas that are clear of cells 4305 and areas that are still covered by the temporary mask 4306, where cells remain in place.

FIG. 43D through FIG. 43F show a subsequent, different operating mode of the invention ("Mode 4" or "Lift-Off Mask") combined with the initial operating step indicated in FIG. 43A through FIG. 43C. Here, the residual mask is used for a lift-off operation in order to pattern a new set of cells 4307 that is seeded into the vessel. After seeding, the cells adhere either to the exposed surface as indicated by 4308, or to the temporary hydrogel mask as indicated by 4309. Finally, the temporary mask is removed by means described above; all cells that were adherent to the mask are removed in washing steps associated with the mask removal. What results is a precisely-patterned heterogeneous cell culture, with the second set of cells 4310 in co-culture with the first set of cells 4311 in a manner precisely defined by the two photolithographic steps.

Embodiments of the disclosure use temporal vectors (for cell state transitions) in conjunction with photolithographic systems for cell culture control and measurement. The OCP embodiment uses photolithographic-style methods ("Photolithography") to apply precision spatial operations on cell cultures using the induced episomal vectors ("ieVectors"). The combination allows programming of cell state transitions using ieVectors with cell-level spatial management of this process in order to result in the desired cell types or combination of cell types in a desired pattern for tissue engineering applications.

The combination of the Photolithography with the ieVector provides numerous features.

For example, the combination of the Photolithography with the ieVector provides for direct spatial patterning of cells that have ieVectors delivered to them onto a surface in the vessel, with patterning achieved by optical means, in order to create highly-controlled heterogeneous cell cultures or tissue. The combination of the Photolithography with the ieVector provides for spatially-selective removal of cells from the vessel by optical means, for the purpose of: removing cells that did not have ieVector delivered (determined by imaging fluorescent delivery reporters in the ieVector(s)); removing cells that do not transcribe the ieVectors (determined by imaging fluorescent transcription reporters in the ieVector(s)); removing cells to control local cell density, including removing cells that have been delivered with varying ieVectors in order to adjust local cell ratios or patterning (where "no delivery" is also a type); or removing cells identified to be incorrectly or sub-optimally transitioning cell states, as determined by imaging and computing subsystem comparison to established feature models. The combination of the Photolithography with the ieVector provides for the spatially-selective delivery of ieVectors to cells through optical means that allow spatial selectivity, and therefore enable local patterning of ieVector delivery or non-delivery, for the purpose of controlling cell type ratios and patterning.

The following examples illustrate embodiments of the Photolithography OCP for use with gene-modulating vectors.

Example 1: Photolithographic Masked Delivery of ieVectors into a Cell Culture

As detailed in FIG. 38A through FIG. 38D, the invention can be used in conjunction with ieVectors to image a cell culture, determine areas where the ieVector should be delivered in order to alter cell state, or alter fate in an overall differentiation protocol; by one of the optical+hydrogel techniques shown in any of FIG. 35A through FIG. 37C, a mask is formed that shields some cells from the ieVector or ieVector delivery construct (lipid complex or virus), while leaving others exposed, in order to selectively deliver the ieVector. Multiple iterations of this process may be performed to pattern complex tissue, or to do follow-up deliveries of ieVectors. The ieVectors may be delivered to the exposed cells by means of a carrier construct (such as a lipid complex or virus) that traverse cell membranes, or through physical delivery methods such as electroporation, ultrasonication, laser cavitation, or impact by droplets, for example through a laser forward transfer system.

Example 2: Photolithographic Patterned Delivery of ieVectors from a Hydrogel Layer As detailed in FIG. 39A through FIG. 39D and FIG. 40A through FIG. 40D, the invention can be used in conjunction with ieVectors to image a cell culture, determine areas where the ieVector should be delivered in order to alter cell state, or alter fate in an overall differentiation protocol; by one of the optical+hydrogel techniques shown in FIG. 35A through FIG. 37C, a protective mask is optically formed over non-target cells in order to block vector delivery; a second layer is formed over the target cells only (in FIG. 39A through FIG. 39D) or over the entire surface (embodiment shown in FIG. 40A through FIG. 40D). The layer contains ieVector-carrying constructs that enter into the cells that it is in contact with, thereby altering the differentiation pathway and cell state.

Example 3: Selective Photolithographic-Masked Removal of ieVector-Delivered Cells As shown in FIG. 41A through FIG. 41D, the invention can be used in conjunction with the ieVectors to image a cell culture after cells are adherent, utilize a computing subsystem that compares cell images to those stored in a storage subsystem, and determine which cells (a) did not have the ieVector properly or sufficiently delivered; (b) are not transcribing the gene modulators in the ieVector; (c) are not differentiating or changing cell state as intended; (d) are not creating or completing the desired tissue patterning; or (e) have characteristics of interest where downstream analysis such as RNA sequencing or PCR may elucidate cell state. From this image, a temporary photo-defined hydrogel mask Is formed on the cell culture, and then exposed cells are removed by trypsinization, by use of an enzyme that breaks down extracellular matrices beneath the cells, or other means.

Example 4: Photolithographic Mask Lift-Off Patterning of ieVector-Delivered Cells As shown in FIG. 43A through FIG. 43F, the invention may be used to successively pattern multiple sets of cells that have had ieVectors delivered. In this example, a removal operation is performed on a first set of cells that have had a first ieVector delivered into them. The mask 4306 that is used to define this removal operation is then used in a second operation where a second set of cells that has been transfected or loaded with a second ieVector is plated onto the cell culture. After cell adhesion, as shown in FIG. 43E, the temporary mask layer is removed by the means described herein, and the cells from the second set that settled on the mask are washed away, resulting in a precisely patterned cell culture.

All examples are shown representatively as a cross-section of a 2-dimensional cell culture, but the present invention is entirely applicable to a 3D cell culture where the operations described are performed on the topmost layer of the cell culture. In this manner, complex multilayer cell and tissue structures may be formed with successive photolithographic steps.

V. System for Cell Manipulation Using Laser-Induced Forward Transfer

The disclosure also includes laser-based methods to selectively transfer cargo into individual cells, onto individual cells, or to selectively transfer individual cells onto a target surface ("bioprinting"). Material of interest is dispersed in a film over a planar donor substrate, which is disposed facing a receiving substrate. A laser scans the donor substrate, energizing the film resulting in the material being transferred forward onto the receiving substrate. Computer imaging and control provides for precise spatial modulation with respect to both the donor and receiving substrates. Such systems and methods generally provide for cell manipulation using laser-induced forward transfer.

Cells may be manipulated using a laser-induced forward transfer (LIFT) system. The system may be used for a variety of applications, which generally fall into one of three categories: (1) intracellular delivery of cargoes into cells via temporary stressing of the cell membrane, (2) ejection of selected cells onto a surface (ie to perform bioprinting), and/or (3) ejection of biocompatible materials onto targeted cells. Preferred embodiments of a LIFT system include a donor substrate, a receiving substrate, an imaging system, and a laser scanning subsystem. The imaging system is preferably coupled to an image analysis subsystem for characterizing the cells or materials imaged by the imaging subsystem.

The donor substrate includes: a surface coated in an aqueous film (preferably sufficiently thin to be able to form droplets) and a substrate that is sufficiently transmissive in the visible range (400 to 700 nm wavelengths) to enable imaging, yet can also absorb laser light at a given wavelength and transfer it to the aqueous layer for the purpose of forming droplets. The aqueous film on the donor substrate may contain biocompatible hydrogels, biocompatible liquids (i.e., cell media, PBS, etc), cargo for delivery, cells, or any combination thereof. The receiving substrate preferably presents a surface, positioned a distance d opposite the donor substrate for the purpose of receiving ejected materials. The receiving substrate may be bare or may contain or be coated in a matrix suitable for cell culture, optionally containing cells, solution containing delivery cargo, or a combination of the three.

The laser scanning may include a laser source and optical system for focusing and aligning the laser source onto the donor substrate or material coating the donor substrate.

In the case of cargo delivery, cells that are to receive the delivery cargo may be cultured in a layer on the donor substrate or may be cultured on a receiving substrate. The ejection of droplets from the donor substrate to the receiving substrate generates mechanical stress on cell membranes, resulting in temporary poration and the potential to deliver membrane-impermeable cargoes into the cells. In the case of bioprinting, the transfer of cell-containing droplets from the donor substrate onto the receiving substrate enables the creation of patterned tissues with a high level of precision. In the case of ejecting materials onto cells, material can be ejected from the donor substrate onto cells cultured on the receiving substrate with single-cell level precision.

The LIFT system is spatially-selective and provides for lateral resolution on the order of microns. This is not possible with the vast majority of other intracellular delivery techniques, including but not limited to: viral delivery, lipofection, and electroporation.

The LIFT system is highly cargo efficient, and makes it possible to use only thin films of cargo-carrying liquid. This has not yet been demonstrated in the literature for diffusion-based delivery techniques using laser-activated nanoparticles or laser-activated substrates.

The LIFT system can be used to deliver to the top layer of cells in a 3D tissue. This is likely not possible with techniques using cells cultured directly on top of laser-activated substrates, for which intracellular delivery has only been proven on monolayers of cells.

The LIFT system allows cells to be cultured on standard tissue culture surfaces and does not require laser-activated materials to be in contact with the cells, unlike other delivery techniques in which cells are cultured directly on the laser-activated substrate. This may be particularly beneficial for applications involving stem cells, which are known to differentiate preferentially in response to mechanical cues from their environment, such as substrate stiffness or topography.

The LIFT system does not result in foreign materials being ingested by the cells, as with delivery using laser-activated nanoparticles. While gold nanoparticles are commonly used for laser-activated delivery, the ingestion of these particles by cells has been shown to have toxic effects. The LIFT system has the ability to deliver a diverse range of cargoes, unlike viruses which are limited to carrying genetic material. The LIFT system has high temporal precision, unlike lipofection, for which delivery often occurs over several hours. The LIFT system reduces and localizes the shear stress on cells, especially when compared to microfluidic squeezing.

In the LIFT system cells do not have to be cultured on a laser-activated substrate or in media containing laser-activated particles. This may be a particularly important advantage for stem cells, which are known to differentiate preferentially in response to environmental cues such as substrate stiffness and topology. In addition, the laser-activated materials are not permanently engulfed by the cells, as is the case with nanoparticle-mediated delivery. This is preferable for clinical applications.

Laser-assisted bioprinting of cells using LIFT: The currently-available laser-assisted bioprinting systems are only used for ejecting cells, not for delivering cargoes to cells. The LIFT system can actively engineer cells and tissues, and control cell fate by delivering membrane-impermeable cargoes into cells. In addition, the invention described here includes an imaging system which may be used to selectively target cells for specific treatment.

The LIFT system is oriented such that the donor substrate is positioned above the receiving substrate, and the laser beam is pointing downward (aligned with gravitational force). The LIFT system takes advantage of kinetic energy by using the shear stress generated by the impact of the droplet with the receiving substrate for intracellular delivery.

The LIFT system is achieves single-cell level precision.

By using laser beams that can be tightly focused, in conjunction with an imaging system that can identify single cells, the LIFT system may be used to target cells with single-cell level precision, for cell types such as induced pluripotent stem cells. In contrast to the 0.5-1.2 mm-diameter droplets formed by electrospray, the average droplet radius for laser-based techniques can range from 3.8 to 9.0 µm.

Preferred embodiments of the LIFT system is have donor subsystem configurations that promote energy transfer. In the LIFT system, a donor subsystem is critical for absorbing laser light energy and converting it to mechanical energy. This results in the formation of droplets from a liquid or gel film coating a donor substrate, which are ejected towards a receiving substrate. The donor subsystem must include a material that is at least semi-absorptive at the wavelength of the laser source used to initiate LIFT. Furthermore, to enable imaging, the donor substrate must be at least partially transparent in the wavelength range used for imaging (400 to 700 nm). For instance, the donor substrate may be composed of a transparent material such as glass or polystyrene, coated in an layer of absorbing material.

The transparent material (glass, polystyrene, etc) may have a thickness on the order of 0.1 to 1 mm, or 1 to 10 mm, which would enable transmission of the imaging wavelengths. Depending on the application, the desired transmission may be >20%, >40%>60%, or >80%.

The absorbing surface may simply be an unpatterned continuous thin film of absorbing material that is deposited onto the transparent surface of the substrate. The thin film may have a thickness in the range of 1 to 10 nm, 10 to 100 nm, or 0.1 to 1 µm. The absorbing material may be a biocompatible metal or metal alloy such as Ti, Au, Ag, or TiN. In certain embodiments, the donor substrate may be composed of 0.3 mm of glass topped with a 20-nm thin film of Ti, or a 50-nm thin film of Au. The absorbing surface may also be composed of two metallic layers, with the metal layer between the transparent surface and second metal serving as an adhesive, such as 2 nm of Cr or Ti topped with 10 nm of Au. In some embodiments, other non-metallic absorbing materials could be used such as amorphous silicon, carbon black, indium tin oxide, or photoabsorbent polymer. The absorbing material may be deposited onto the transparent surface by sputtering, thermal evaporation, or electron-beam deposition.

In other embodiments, the absorbing material may be a patterned surface atop the transparent surface, as opposed to an unpatterned continuous thin film. The transparent surface could be covered in an array of absorbing structures, such as pyramids, spheres, discs, squares, rods, cavities, crescents, or pillars. The structures may have dimensions on the order of 1 to 10 nm, 10 to 100 nm, 0.1 to 1 µm, or 1 to 10 µm. The absorbing structures may be joined together by a continuous thin film of absorbing material (e.g. Ti, Au, TiN, Ag, carbon black, indium tin oxide, photoabsorbent polymer etc.) or may be independent structures spaced apart on a transparent substrate. In an example embodiment, the donor substrate could be composed of a 0.3 mm glass substrate topped with an array of 60-nm diameter 15-nm thick Au discs. Another example embodiment could be the negative of such an array—a 0.3 mm glass substrate topped with a continuous 15-nm thin film of Au, punctuated with an array of 60-nm diameter holes.

In certain embodiments, the opposite side of the donor substrate (the side not covered in absorbing material/structures), may be coated with an anti-reflection coating, to reduce reflection to <5% for a given laser wavelength. For instance, in certain embodiments, multiple layers of quarter-wave thick MgF2 coatings may be applied to the non-absorbing side of the donor substrate via physical vapor deposition, to achieve a reflectivity to below 1% at the chosen laser wavelength.

In other embodiments, the absorbers may not be attached to the transparent surface, but may be contained in the aqueous film coating the transparent donor substrate. For instance, absorbing structures such as nanospheres, microspheres, nanorods, nanostars, or nanotriangles could be suspended in the aqueous film. The structures may have dimensions on the order of 1 to 10 nm, 10 to 100 nm, 0.1 to 1 µm, or 1 to 10 µm. These structures could be composed of any material designed to absorb at the given laser wavelength, such as metals or metal alloys (Ti, Au, Ag, TiN, etc.), carbon black, or photoabsorbent polymers. In certain embodiments, 20-nm diameter Au nanospheres may be suspended in the aqueous film, or attached to cells cultured on the transparent donor substrate. In another embodiment, 60-nm aggregates of carbon black could be suspended in an aqueous film coating the substrate. The absorbing structures may also be composed of more than one material. In an example embodiment, the absorbing structures may be composed of 50-nm diameter Ag nanospheres coated in a 5-nm thick Au shell. In other embodiments, the absorbing materials may be photoabsorbent molecules suspended in the aqueous film coating the donor substrate, such as phenol red, allura red, or melanin. In an example embodiment, the donor substrate may be coated in a hydrogel containing cargo for intracellular delivery and melanin designed to absorb at the given laser wavelength.

The absorbers in the donor subsystem may transfer optical energy to mechanical energy via the generation of a pressure wave following the expansion and collapse of a bubble, following the vaporization of a material, and/or following the thermal expansion of a material. These processes require >0% absorption at the laser wavelength by the absorbing material. Depending on the application, the desired absorption may be >20%, >40%>60%, or >80%. Some examples of potential configurations and their associated energy transfers are:

A donor substrate with an unpatterned continuous thin film of absorbing material is coated in a continuous thin aqueous film. A laser is focused tightly on the laser-absorbing material, causing it to partially vaporize and subsequently deform in the illuminated area, breaking the surface tension of the liquid/gel film and generating a droplet.

A donor substrate composed of an unpatterned continuous thin film of a laser-absorbing material is coated in a continuous thin aqeuous film. A laser is focused tightly on the laser-absorbing material, causing it to thermally expand in the illuminated area, breaking the surface tension of the aqueous film and generating a droplet.

A donor substrate composed of an unpatterned continuous thin film of laser-absorbing material is covered by a mask with holes. Within the holes are thin aqueous films, so that the end result is an array of menisci formed by the aqueous material. A laser is focused tightly on the laser-absorbing material, causing it to partially vaporize and subsequently deform or thermally expand in the illuminated area above the menisci, breaking the surface tension of the liquid/gel film and generating a droplet.

A donor substrate is composed of a patterned array of plasmonic metallic nanostructures, which are then coated by an aqueous film. A larger laser beam spot may be used in this case, as the plasmonic nanostructures act to focus the light, creating multiple localized hotspots. These hotspots absorb the laser light energy and transfer the energy to the surrounding environment in such as way as to create bubbles in the nearby aqueous film. The creation of bubbles deforms the aqueous film, resulting in the formation of droplets that are ejected from the film.

A transparent substrate is coated in an aqueous film containing plasmonic nanostructures. The laser light is focused onto the liquid layer containing the plasmonic nanostructures, generating plasma-mediated bubbles that deform the aqueous film, resulting in the formation and ejection of droplets.

A transparent substrate is coated in a continuous film of liquid or gel. A laser wavelength is chosen that is efficiently absorbed by the liquid/gel. The laser is tightly focused in the top region of the liquid/gel, where the energy is absorbed and transferred to the surrounding liquid, generating a bubble that forces droplets below it towards the receiving substrate.

A transparent substrate is coated in a thin film of liquid or gel loaded with a photoabsorbent dye. The laser is tightly focused onto a region of the liquid/gel, causing it to heat up, generating a bubble, which forces droplets below it towards the receiving substrate.

The LIFT system may be characterized in terms of the donor substrate position relative to cells. The cells may be positioned on the donor substrate or receiving substrate, depending on the application.

Figure 44:
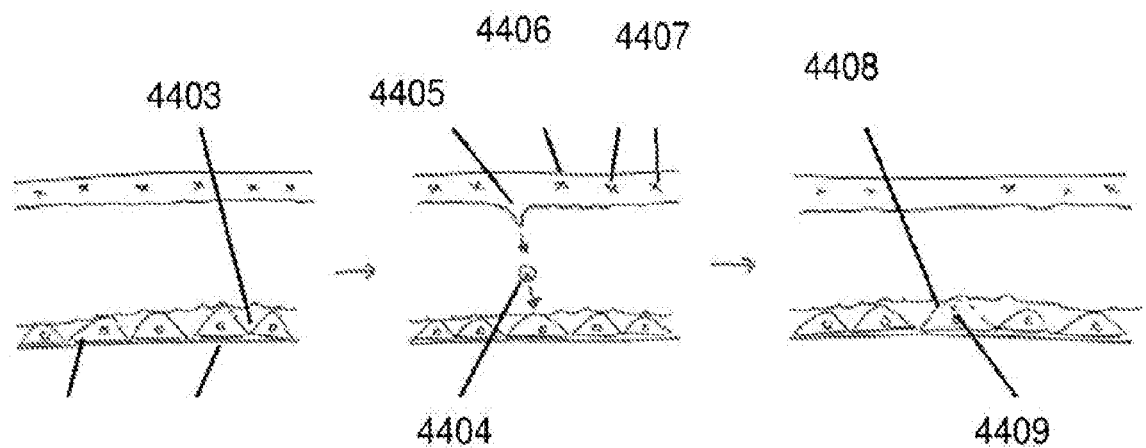
FIG. 44 shows the use of LIFT for intracellular delivery.

FIG. 44 shows the use of LIFT for intracellular delivery. Cells 4401 are cultured on the receiving substrate 4402. The majority of the cell media may be aspirated from the cells on the receiving substrate, leaving behind the monolayer of cells along with trace amounts of liquid 4403. The droplets 4404 ejected from a film 4405 coating the donor substrate 4406 could contain the delivery cargo 107, which is ejected towards the cells.

FIG. 44 shows that upon impact, the cell membrane 4408 is porated and the cargo 4409 is delivered into the cell. We have already demonstrated proof of this technique by using LIFT to eject membrane-impermeable fluorescent dyes from a laser-activated substrates into induced pluripotent stem cells (iPSCs) cultured in a standard tissue culture plates.

Figure 45:
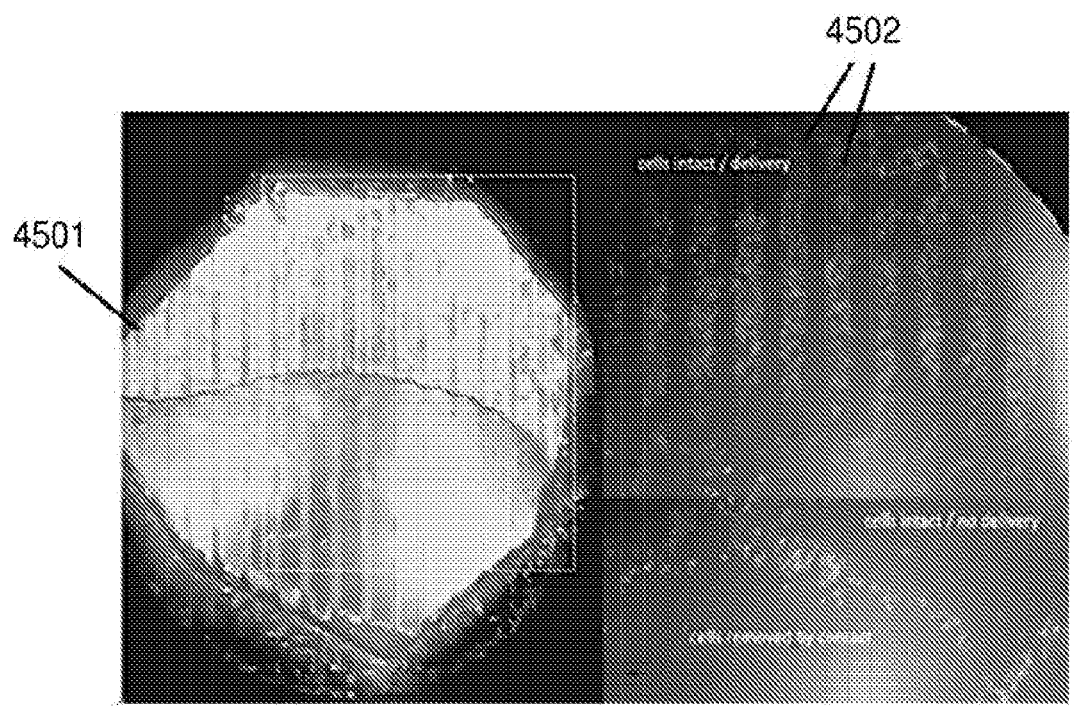
FIG. 45 shows the use of LIFT to deliver membrane-impermeable fluorescent dyes into cells.

FIG. 45 shows the use of LIFT to eject membrane-impermeable fluorescent dyes from a laser-activated substrates into induced pluripotent stem cells (iPSCs) cultured in a standard tissue culture plates. The image on the left shows the laser-activated substrate 4501, which was covered by a thin layer of aqueous solution containing the delivery cargo. The image on the right is a fluorescence image showing successful delivery of the fluorescent dyes to cells; the laser was scanned in stripes, therefore resulting in stripes of delivery 4502.

Figure 46:
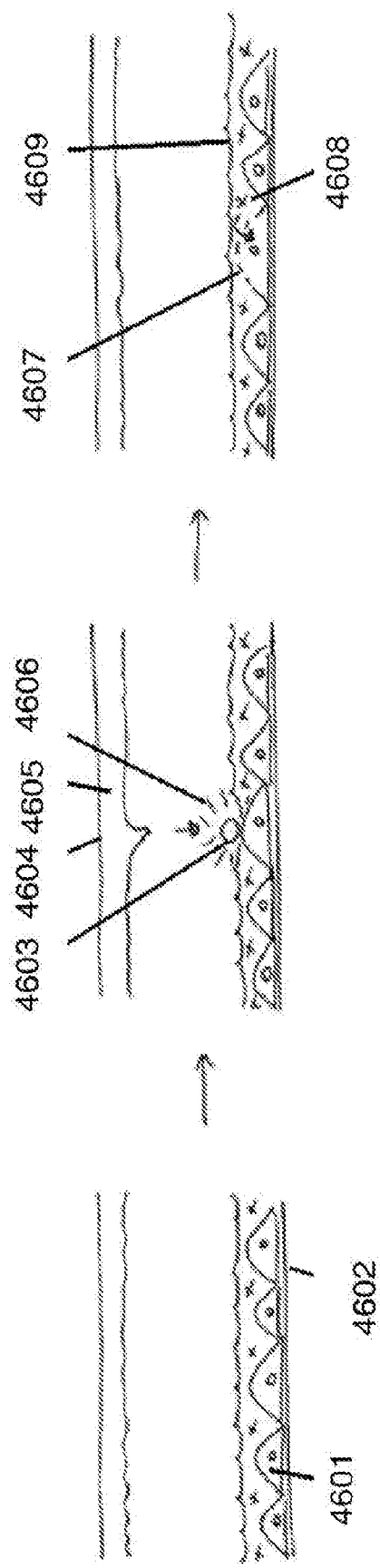
FIG. 46 shows using LIFT-ejection of droplets to porate cells.

FIG. 46 shows using LIFT to kinetically porate cells. The droplets 4603 ejected from the donor substrate 4604 could simply be a "dummy" solution 4605 (e.g. cell media, PBS, a biocompatible hydrogel) that serves only to impact 4606 the cells. This impact results in temporary membrane poration 4607. In the depicted embodiment, the delivery cargo 4608 may be present in a thin film of the media solution 4609 surrounding the cells, and diffuse into the cells upon membrane poration with the dummy solution.

Figure 47:
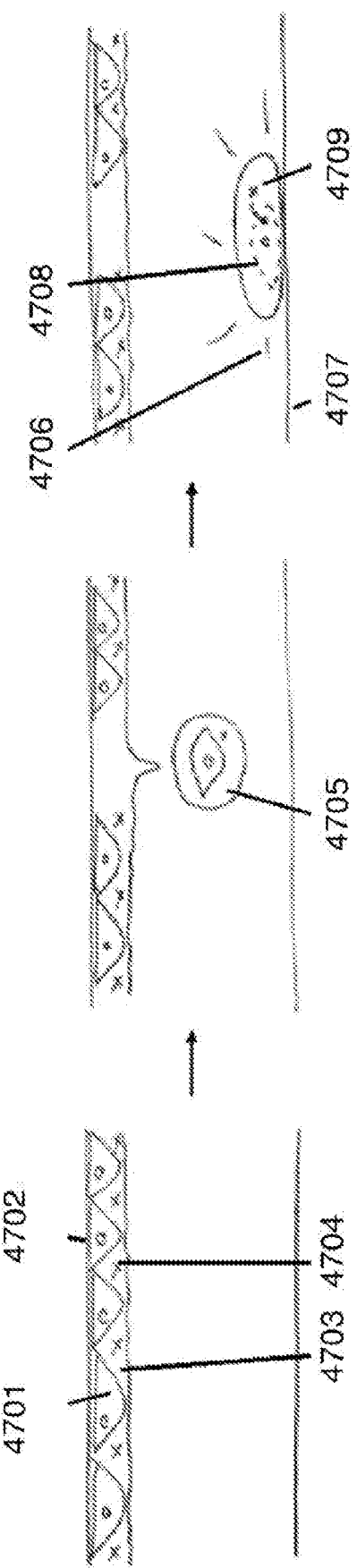
FIG. 47 shows using LIFT-ejection of cells to porate the cell membrane.

FIG. 47 shows an approach in which cells 4701 are positioned on the donor substrate 4702, in a solution 4703 containing the desired delivery cargo 4704. As droplets 4705 containing the cells and delivery cargo are ejected from the donor substrate and impact 4706 the receiving substrate 4707, the shear forces generated from the impact porate the cell membrane 4708, enabling the delivery cargo 4709 to diffuse into the cells.

FIG. 48 shows cells 4801 cultured on the donor substrate 4802 for bioprinting. Desired cells 4803 are then ejected onto the receiving substrate 4804.

FIG. 49 shows cells 4901 positioned on the receiving substrate 4902, tor selectively ejecting biocompatible materials onto cells. The material 4903 to be ejected is coated on the donor substrate 4904 and ejected onto targeted cells 4905 on the receiving substrate.

The LIFT systems may be characterized according to laser system configurations.

The laser source used to initiate LIFT may be continuous wave but is preferably pulsed (to minimize thermal damage to cells and intracellular delivery cargo). In some embodiments, the pulse widths may range from 10 to 100 fs, 0.1 to 1 ps, 1 to 10 ps, 10 to 100 ps, 0.1 to 1 ns, 1 to 10 ns, 10 to 100 ns, 0.1 to 1 μs, or 1 to 10 μs. In certain embodiments, the laser system and wavelength used may be a 532 nm Nd:YAG, 1064 nm Nd:YAG, 650-1100 nm Ti:Sapphire, 980 nm diode, 351-528 nm Argon, 193 nm ArF, 248 nm KrF, 308 nm XeCl, 353 nm XeF, 390-435 nm stilbene, 460-515 nm coumarin, 570-640 nm rhodamine, 510 nm copper vapor, 578 nm copper vapor, 627 nm gold vapor, 1320 nm Nd:YAG, 694 nm ruby, 2940 nm Er:YAG, 2100 nm Ho:YAG, or 700-820 chromium-doped chrysoberyl (alexandrite) laser. The source may be a Q-switched laser. The laser source may be a fiber laser.

Depending on the absorbing material used in the donor substrate and the laser characteristics (wavelength, pulse width, peak intensity, etc.), the fluence, or energy/unit area, used may be within 1 to 10 mJ/cm^2, 10 to 100 mJ/cm^2, 100 to 1000 mJ/cm^2, or 0.1 to 1 J/cm^2. The exact fluence used will also depend on the application (cell poration, cell ejection, cell killing, cargo ejection, etc.) and the distance between the absorber and the cells.

In some embodiments, the diameter of the laser beam spot may be in the range of 1 to 10 μm, 10 to 100 μm, or >100 μm. The diameter of the laser beam spot may depend on the chosen absorber, and the maximum power output of the laser source.

Embodiments of the disclosure provide for image-driven LIFT-based delivery, bioprinting, or ejection of materials onto cells.

An imaging subsystem may be used in conjunction with the laser-scanning subsystem that transfers energy to the material coating the donor substrate. The imaging subsystem may be used to image the receiving substrate or the material coating the receiving substrate for the purpose of: identifying individual cells or groups of cells to deliver cargoes to; identifying individual cells or groups of cells to be destroyed and/or killed; identifying regions of the receiving substrate onto which to eject cells; or identifying individual cells or groups of cells to eject biocompatible material onto for downstream applications. The imaging subsystem may also be used to image the donor substrate or the material coating the donor substrate for the purpose of identifying individual cells or groups of cells to be ejected onto the receiving substrate Embodiments of the lift system use an imaging subsystem positioned relative to the laser scanning subsystem and donor/receiving subsystems.

Figure 50:
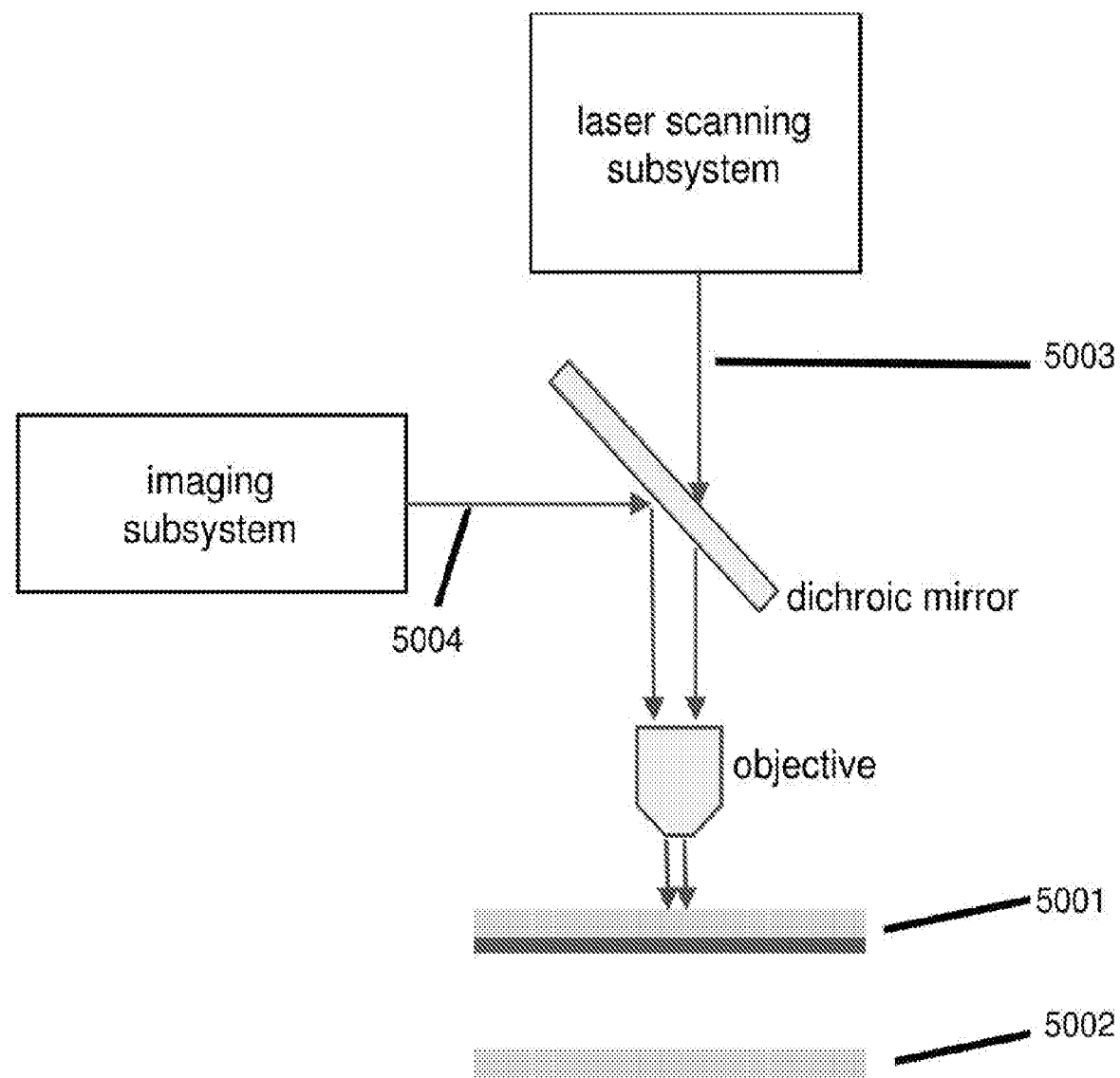
FIG. 50 shows a LIFT embodiment.

FIG. 50 shows an embodiment in which the donor substrate 5001 may be positioned above the receiving substrate 5002, with the laser beam 5003 coming from above or below the donor substrate and focusing onto the donor substrate. The imaging subsystem may also be positioned above the donor substrate (ie on the same side as the laser subsystem), and light used for imaging 5004 may be focused onto the receiving substrate, the material covering the receiving substrate, the donor substrate, or the material covering the donor substrate. In this example, the donor substrate would be at least semi-transparent to wavelengths used for imaging, in order to permit imaging through the substrate, but would also be capable of absorption at the wavelength used by the laser scanning system. For instance, the substrate could be composed of a 0.3-mm layer of glass coated with a 20-nm layer of titanium. This substrate would have approximately 30% transmission across the visible spectrum, and absorb approximately >50% of 532-nm light emitted by a nanosecond-pulsed Nd:YAG laser system.

The donor substrate may be positioned above the receiving substrate, with the laser coming from above or below the donor substrate and focusing onto the donor substrate or the liquid/gel film covering the donor substrate. The imaging subsystem may be positioned below the receiving substrate (ie on the opposite side as the laser subsystem), and may be focused onto the receiving substrate, the material covering the receiving substrate, the donor substrate, or the material covering the donor substrate.

LIFT Example Embodiment

In one embodiment, the donor substrate may be composed of a 0.3-mm thick glass substrate coated on one side with a 20-nm thin layer of thermally evaporated Ti. On the other side, a quarter-wave thick layer of MgF2 is deposited via physical vapor deposition. Induced pluripotent stem cells may be cultured in a monolayer on the Ti-coated side of the donor substrate. Vectors encoding gene modulators and fluorescent reporters are delivered to the iPSCs via conventional means (ie viral vector delivery, electroporation, lipofection, etc). The cell media is aspirated from the cell culture, resulting in an iPSC monolayer with trace amounts of liquid remaining on the Ti-coated substrate. The substrate is then positioned upside-down over a 6-well plate. The 6-well plate functions as a receiving container. The iPSCs are imaged in brightfield and fluorescence through the Ti-coated substrate, which transmits approximately 30% of light in the visible range (400 to 700 nm wavelengths). Image analysis classifies the imaged iPSCs into six distinct populations based on expression levels of the various fluorescent reporters. A 532-nm Nd:YAG laser with 7-ns pulses and a 5 µm diameter beam spot is then focused onto the Ti substrate at a fluence below 100 mJ/cm^2. The Ti surface absorbs approximately 55% of the incoming 532-nm light, transferring the optical energy to the aqueous film and creating bubbles, which separate the targeted iPSCs from the Ti surface and eject them into wells of the 6-well plate.

Example Applications Using Image-Driven LIFT-Based Delivery/Bioprinting/Ejection of Materials onto Cells The invention described here may be used in a number of applications requiring high-precision cell and tissue engineering. Several examples of how image-based analysis can be used to direct cell engineering with single-cell-level precision are described in International Patent Application PCT/US19/4596 (System for Image-Driven Cell Manufacturing), incorporated by reference. Potential uses for the image-driven LIFT-based cell engineering technology are described herein.

Examples of Applications for LIFT-Based Delivery:

Cargoes could be delivered to targeted cells based on cell status, as measured by the imaging system and subsequent image analysis.

Gene modulators, vectors encoding gene modulators, and/or differentiation reagents could be delivered to targeted cells to direct stem cell differentiation. The exact modulators/reagents delivered to specific cells could be determined based on the cell's current phenotype and the desired final cell state. In the case of delivering vectors encoding gene modulators, the vectors could also be designed to encode fluorescent reporters, which would enable successful delivery to be determined via image and image analysis. Cargoes could be delivered to slow down or speed up cell division or growth based on local or global cell density. Cargoes designed to manipulate the cells' position in the cell cycle could be delivered to select cells for the purpose of synchronizing the cell cycle of all cells within a culture. Cell-specific nutrients could be delivered to targeted cells within a heterogenous cell culture. For instance, a cell culture may contain two cell types, but a given nutrient may only be beneficial for one of the cell types and harmful for the other. Cargoes designed to induce apoptosis or necrosis could be delivered to cells expressing an undesired phenotype.

Barcodes or labels could be delivered to cells for the purpose of tagging individual cells for downstream analysis. The results of the downstream analysis (eg single-cell RNAseq, qPCR) could then be connected to the images of the cells for the purpose of developing machine learning algorithms for characterizing cells based on image analysis. The system described here could be used to perform highly cargo-efficient intracellular delivery, by using the imaging subsystem to identify regions of a cell culture with cells (for instance, if the cell culture is not fully confluent) and delivery cargo would only be ejected from the donor substrate onto the regions of the receiving substrate that are known to contain cells.

In cases where the system is used for intracellular delivery, the imaging and image analysis subsystems could be used to confirm delivery to the intended cells. In one embodiment, a machine learning algorithm may be used to identify, via brightfield or phase contrast images, whether a cell was porated. In another embodiment, the delivery cargo may include a vector encoding fluorescent reporters, and expression of the fluorescent reporter is therefore indicative of successful delivery. This information could then be used to determine whether specific cells need to be delivered to again, or whether specific cells need to be removed.

Examples of applications for LIFT-based bioprinting: The system may be used to manufacture highly-patterned tissues in both the x-y and z-directions. For example, the retina is composed of layers of cells—the bottom layer contains retinal pigment epithelial cells (RPEs), the next layer contains photoreceptors (rods and cones), and the following layer contains retinal ganglion cells. A donor substrate containing a population of differentiated RPEs could be imaged to identify the most mature and functional RPEs, which are then ejected onto a receiving substrate to form the first layer of the retina. A donor substrate containing a population of rod cells and a (potentially separate) donor substrate containing a population of cone cells could then both be used to eject rods and cones onto the RPE layer to form the photoreceptor layer. By imaging the receiving substrate and deposited cells, the rods and cones could be deposited relative to each other with highly precise spatial patterning, to mimic the spatial patterning of rods and cones in the human retina, for example. Finally, a donor substrate containing a population of retinal ganglion cells is imaged, and retinal ganglion cells of the desired phenotype and maturity level are ejected onto the photoreceptor cells to form the final layer of the retina.

Examples of Applications for LIFT-Based Ejection of Materials onto Cells:

LIFT could be used to achieve spatially-selective delivery of cargoes that are typically not amenable to poration-based delivery techniques, and typically only delivered via non-spatially-selective techniques. For example, large vectors/plasmids and mRNAs that are often too large to enter through pores and are therefore typically delivered with viruses or lipofection. The imaging and image analysis subsystems could be used to identify cells of interest on the receiving substrate. LIFT could then be used to deposit viral vectors or liposomes containing plasmids for delivery onto the regions of the receiving substrate containing the selected cells.

LIFT could be used to deposit hydrogels containing time-release cargoes, such as small molecules, or larger cargos such as episomal vectors with intracellular delivery vehicles such as liposomes or viruses, onto cells of interest (as identified via imaging). The cargoes would then be locally released into the nearby cells over time.

LIFT could be used to "mask" cells to prevent them from further manipulation in downstream processes. For instance, the imaging and image analysis subsystems may determine that a population of cells needs to be further manipulated to achieve the desired final product. LIFT could then be used to deposit a protective "masking" material onto the remaining cells, so that they are not subjected to further processing. The unmasked cells may then be further engineered by exposure to viral vectors, liposomes, chemicals, or small molecules. The protective "masking" material may consist of any biocompatible polymer. In some embodiments, the biocompatible polymer may be photo-responsive, such as a free-radical chain photopolymerized poly(ethylene glycol)

norbornene hydrogel with degradable metalloproteinase peptide linkers, or a poly(ethylene glycol) diacrylate containing photocleavable linkers. In other embodiments, the biocompatible polymer may be temperature-responsive, such as poly(N-isopropylacrylamide). In other embodiments, the biocompatible polymer may be composed of natural bioinks, such as gelatin, hyaluronic acid, collagen, or methylcellulose.

Other Example LIFT Applications:

The LIFT system may be used to kill and/or destroy cells expressing an undesired phenotype. The cells to be killed could be identified via image-based characteristics, and the system could kill and/or destroy the cells by over-stressing the cell membrane, via LIFT-ejection of liquid or gel material towards the targeted cells. The system described here may be used to porate cells for the purpose of extracting molecules of interest (eg small molecules, proteins, enzymes, etc) from targeted cells for bioproduction or for downstream analysis.

This document describes the integration of the OCP embodiment using laser-induced forward transfer (LIFT) to manipulate cells in an adherent cell culture in conjunction with induced episomal vectors for cell state control. The combination allows programming of cell state transitions using ieVectors with cell-level spatial management of this process in order to result in the desired cell types or combination of cell types in a desired pattern for tissue engineering applications.

The combination of the LIFT system with the temporal vectors provides for direct spatial patterning and spatially selective delivery. Cells that have ieVectors delivered to them may be directly spatially patterned onto a surface in the vessel, with patterning achieved by optical means, in order to create highly-controlled heterogeneous cell cultures or tissue. Temporal vectors may be spatially-selectively delivered to cells through optical means that allow spatial selectivity, and therefore enable local patterning of ieVector delivery or non-delivery, for the purpose of controlling cell type ratios and patterning.

To illustrate the use of the LIFT subsystem with the ieVectors, we include two example embodiments, one for direct spatial patterning of ieVector-carrying cells onto a substrate, and another for spatially-selective delivery of ieVectors into cells in cell culture vessel, both in order to result in patterned tissues upon ieVector-driven differentiation of cells.

Example 1: Spatially-Selective Delivery of ieVector by LIFT

FIG. 51A through FIG. 51D show an example of an OCP based on LIFT used to selectively delivery ieVector constructs.

FIG. 51A shows a starting adherent cell culture 5101 rests in a vessel. A LIFT surface 5102 carries a liquid or gel with ieVector constructs or carriers 5103.

FIG. 51B shows a pulsed laser illumination system 5104 used to eject this liquid as droplets 5105 onto the cell culture in a spatially-specific manner. The impact of the droplets may temporarily porate the cell membranes, allowing the ieVector in the received droplet 5106 to pass into the cytoplasm directly, or an ieVector carrier (lipid particle, virus) may facilitate entry of the ieVector into the cells. The liquid containing the ieVector may be engineered to increase viscosity and therefore localize the delivery of the ieVector (reduce diffusion to other nearby cells). Subsequent to this operation, successful delivery of the vector to target cells 5107 may be confirmed by imaging of the delivery reporter; likewise as chemical cues are added to induce transcription, imaging may be used to confirm proper transcription. When delivery or transcription is not detected, a laser-based system described elsewhere may be used to remove target cells where delivery or transcription are not occurring, or conversely, non-target cells that show signs of inadvertent ieVector delivery. In another embodiment, additional LIFT deliveries may be made to cells that do not show signs of delivery and/or transcription. "Non-target" cells 5108 may be have different ieVectors delivered, or differentiate purely based on small molecules added to cell media.

FIG. 51C shows the target cells 5107 after delivery.

At specified timepoints, or based on image features of the cell culture (to measure progression of differentiation), chemical triggers to induce transcription of gene modulators from episomal vector are added to the cell media; these cause transcription from one or more ieVector types that have been introduced into cells. The process of vector delivery can be repeated multiple times, with the same or different set of vectors, and with the same or different groups/areas of target cells, in order to pattern diverse tissue.

FIG. 51D shows the diverse tissue with first cell type 5109 and second cell type 5110.

Example 2: Direct ieVector-Loaded Cell Patterning with LIFT

FIG. 52A shows an example of the use of LIFT ejection to directly pattern ieVector-laden cells. An existing adherent cell culture 5201 grows on a vessel surface. This first set of cells may have ieVectors active. It may be pre-patterned using laser removal methods described herein, removing areas where a second cell type is to be deposited. A LIFT surface 5202 carried a liquid or gel 5203 with cells (white circles) that have been pre-delivered with an ieVector. They may have been pre-sorted to select for cells with proper delivery of the vectors. A pulsed laser system 5204 illuminates sections of the LIFT substrate in order to eject droplets 5 205 with cells from this second set.

FIG. 52B shows the resulting cells 5207, 5208.

What is claimed is:

1. A system, the system comprising:
    a surface having cells cultured on the surface;
    a laser scanning subsystem positioned to emit coherent light towards the surface;
    an imaging subsystem positioned to receive light from the surface; and
    a computer processor programmed to receive an image of cells from the imaging subsystem and operate the laser scanning subsystem to use the coherent light to selectively remove one or more cells from the surface to manage the cells cultured on the surface, wherein managing the cells comprises at least one of:
        controlling local cell density of the cells cultured on the surface;
        removing cells that are not properly differentiating;
        removing cells based at least in part on predicted functional characteristics; and
        removing cells based at least in part on a ratio of cell types of the cells cultured on the surface.

2. The system of claim 1, wherein the surface is biocompatible.

3. The system of claim 1, further comprising a monolayer of adherent cells cultured on a receiving surface opposed to the surface.

4. The system of claim 3, wherein the receiving surface receives cells ejected from the surface.

5. The system of claim 3, wherein the surface is positioned above the receiving surface along a vertical axis such that gravitational force acts downward from the surface to the receiving surface.

6. The system of claim 3, wherein the surface is positioned above the receiving surface such that cells ejected from the surface fall down to the receiving surface.

7. The system of claim 1, wherein the surface comprises a material that responds to laser stimulation by transferring energy to cells cultured on the surface in a spatially-controllable manner.

8. The system of claim 1, wherein the surface is sufficiently transparent such that cells on the surface can be imaged from the opposite side.

9. The system of claim 1, wherein the surface comprises a material that absorbs laser light and transfers the energy to cells cultured on the surface.

10. The system of claim 1, wherein operation of the system performs (1) intracellular delivery of cargoes into cells via temporary stressing of the cell membrane, (2) ejection of cells from the surface, or (3) ejection of biocompatible materials onto targeted cells.

11. The system of claim 1, wherein the surface includes: a surface that is sufficiently transmissive in the visible range to enable imaging, yet can also absorb laser light at a given wavelength and transfer it to the cells cultured on the surface.

12. The system of claim 1, wherein the laser scanning subsystem includes a laser source and an optical system for focusing and aligning the laser source onto the surface or a material coating the surface.

13. The system of claim 1, wherein the laser scanning subsystem is further configured to selectively eject the cells cultured on the surface.

14. The system of claim 1, wherein the laser scanning subsystem has single-cell-level precision for cell removal.

15. The system of claim 1, wherein the computer processor uses the image of cells to determine cells to be removed from the surface.

16. The system of claim 1, wherein the cells cultured on the surface comprise induced pluripotent stem cells.

17. The system of claim 1, wherein the computer processor is further programmed to characterize cells in the image of the cells.

18. A method, comprising:
culturing cells on a surface;
emitting, using a laser scanning subsystem, coherent light towards the surface;
receiving, using an imaging subsystem, light from the surface;
receiving, using a computer processor, an image of the cells from the imaging subsystem; and
controlling the laser scanning subsystem to use the coherent light to selectively remove one or more cells from the surface to manage the cells cultured on the surface, wherein managing the cells comprises at least one of:
(i) control local cell density of the cells on the surface,
(ii) remove cells that are not properly differentiating,
(iii) remove cells based at least in part on predicted functional characteristics,
(iv) remove cells based at least in part on a ratio of cell types of the cells cultured on the surface, or any combination thereof.

19. The method of claim 18, wherein the surface is biocompatible.

20. The method of claim 18, further comprising culturing a monolayer of adherent cells on a receiving surface opposed to the surface.

21. The method of claim 20, further comprising receiving, using the receiving surface, cells ejected from the surface.

22. The method of claim 20, further comprising positioning the surface above the receiving surface along a vertical axis such that gravitational force acts downward from the surface to the receiving surface.

23. The method of claim 20, further comprising positioning the surface above the receiving surface such that cells ejected from the surface fall down to the receiving surface.

24. The method of claim 18, wherein the surface comprises a material that responds to laser stimulation by transferring energy to cells cultured on the surface in a spatially-controllable manner.

25. The method of claim 18, wherein the surface is sufficiently transparent such that cells on the surface can be imaged from the opposite side.

26. The method of claim 18, wherein the surface comprises a material that absorbs laser light and transfers the energy to cells cultured on the surface.

27. The method of claim 18, further comprising performing (1) intracellular delivery of cargoes into cells via temporary stressing of the cell membrane, (2) ejection of cells from the surface, or (3) ejection of biocompatible materials onto targeted cells.

28. The method of claim 18, wherein the surface includes: a surface that is sufficiently transmissive in the visible range to enable imaging, yet can also absorb laser light at a given wavelength and transfer it to the cells cultured on the surface.

29. The method of claim 18, wherein the laser scanning subsystem includes a laser source and an optical system for focusing and aligning the laser source onto the surface or a material coating the surface.

30. The method of claim 18, further comprising selectively ejecting, using the laser scanning subsystem, the cells cultured on the surface.

31. The method of claim 18, wherein the laser scanning subsystem has single-cell-level precision for cell removal.

32. The method of claim 18, further comprising using the image of the cells to determine one or more cells to be removed from the surface.

33. The method of claim 18, wherein the cells cultured on the surface comprise induced pluripotent stem cells.

34. The method of claim 18, further comprising characterizing cells in the image of the cells.

* * * * *